United States Patent
Subramanian et al.

(10) Patent No.: US 8,609,406 B2
(45) Date of Patent: *Dec. 17, 2013

(54) NON-STATIC SUSPENSION CULTURE OF CELL AGGREGATES

(75) Inventors: Kartik Subramanian, Westborough, MA (US); Wei-Shou Hu, Falcon Heights, MN (US); Catherine M. Verfaillie, Leuven (BE); Yonsil Park, Daejeon (KR)

(73) Assignees: Regents of the University of Minnesota, St. Paul, MN (US); Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,052

(22) Filed: Aug. 24, 2011

(65) Prior Publication Data

US 2012/0052568 A1    Mar. 1, 2012

Related U.S. Application Data

(60) Provisional application No. 61/376,508, filed on Aug. 24, 2010.

(51) Int. Cl.
C12N 5/00    (2006.01)
C12N 5/02    (2006.01)

(52) U.S. Cl.
USPC .......................................... 435/325; 435/383

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. |
| 5,827,735 A | 10/1998 | Young et al. |
| 5,906,934 A | 5/1999 | Grande et al. |
| 6,090,625 A | 7/2000 | Abuljadayel |
| 6,214,369 B1 | 4/2001 | Grande et al. |
| 6,653,134 B2 | 11/2003 | Prockop et al. |
| 6,777,231 B1 | 8/2004 | Katz et al. |
| 7,015,037 B1 | 3/2006 | Furcht et al. |
| 7,045,148 B2 | 5/2006 | Hariri |
| 7,056,738 B2 | 6/2006 | Prockop et al. |
| 7,229,827 B2 | 6/2007 | Kim et al. |
| 7,311,905 B2 | 12/2007 | Hariri |
| 2001/0033834 A1 | 10/2001 | Wilkison et al. |
| 2001/0046489 A1 | 11/2001 | Habener et al. |
| 2002/0061587 A1 | 5/2002 | Anversa |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2004/0033214 A1 | 2/2004 | Young et al. |
| 2004/0235165 A1 | 11/2004 | Prockop et al. |
| 2005/0169896 A1 | 8/2005 | Li et al. |
| 2005/0255588 A1 | 11/2005 | Young et al. |
| 2006/0177925 A1 | 8/2006 | Rosenberg et al. |
| 2010/0239542 A1 | 9/2010 | Young et al. |
| 2010/0239543 A1 | 9/2010 | Young et al. |
| 2011/0064701 A1 | 3/2011 | Young et al. |

FOREIGN PATENT DOCUMENTS

| | | |
|---|---|---|
| WO | WO 96/23870 | 8/1996 |
| WO | WO 99/16863 | 4/1999 |
| WO | WO 99/35243 | 7/1999 |
| WO | WO 01/04268 | 1/2001 |
| WO | WO 01/08691 | 2/2001 |
| WO | WO 01/21766 | 3/2001 |
| WO | WO 01/21767 | 3/2001 |
| WO | WO 01/62901 | 8/2001 |
| WO | WO 02/08388 | 1/2002 |
| WO | WO 02/34890 | 5/2002 |
| WO | WO 2009/092092 | 7/2009 |

OTHER PUBLICATIONS

Kehoe et al. (Oct. 2009) Scalable stirred-suspension bioreactor culture of human pluripotent stem cells. Tissue Engineering Part A 16(2): 405-421.*
Youn et al. (2005) Large-scale expansion of mammary epithelial stem cell aggregates in suspension bioreactors. Biotechnology Progress 21: 984-993.*
Dang et al. (2002) Efficiency of embryoid body formation and hematopoietic development from embryonic stem cells in different culture systems. Biotechnology and Bioengineering 78(4): 442-453.*
Cambrex specimens, "Poietics Human Mesenchymal Stem Cell Systems," Cambrex BioScience Walkersville, Inc. (2005).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).

(Continued)

*Primary Examiner* — Anne-Marie Falk
(74) *Attorney, Agent, or Firm* — Tarolli, Sundheim, Covell & Tummino LLP

(57) ABSTRACT

The invention is directed to compositions of cell aggregates and methods for making and using the cell aggregates where the aggregates comprise cells that are not embryonic stem cells but can differentiate into cell types of at least two of ectodermal, endodermal, and mesodermal embryonic germ layers, e.g., stem cells.

8 Claims, 25 Drawing Sheets

(56) References Cited

OTHER PUBLICATIONS

Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.; 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR- cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, Rox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stomal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone marrow stromal cells differentiate into neural cells in vitro" Exp. Neurol.; 164:247-56 (2000).
Eglitis et al., "Hematopoietic cells differentiate into both microglia and macroglia in the brain of adult mice" Proc. Natl. Acad. Sci. USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).

(56) References Cited

OTHER PUBLICATIONS

Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office, Office Action and 892 dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action and 892 dated Apr. 7, 2008 in related U.S. Appl. No. 11/151,689.
U.S. Patent and Trademark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action and 892 dated Apr. 3, 2007 in related U.S. Appl. No. 11/238,234.
U.S. Patent and Trademark Office, Office Action dated Oct. 7, 2008 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement, Second Communication and PTO/SB/08b, filed Dec. 24, 2008 in related U.S. Appl. No. 11/238,234.
International Search Report for PCT/US11/48972; Jan. 17, 2012.

\* cited by examiner

FIG. 5
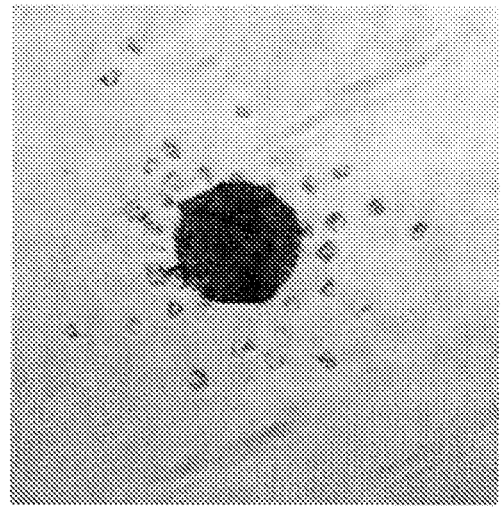
- LOW OCT4 MAPC AGGREGATES WERE FORMED FROM 8000 CELLS AND TOOK 7 DAYS TO FORM.
- SIZE: ~150-200 μm
- DIFFERENTIATED SPONTANEOUSLY TO DIFFERENT CELL TYPES
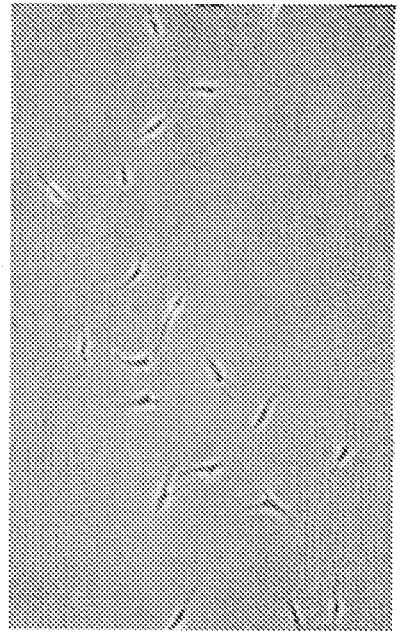
LOW OCT4 MAPC
MAPC MEDIA, 5% O₂
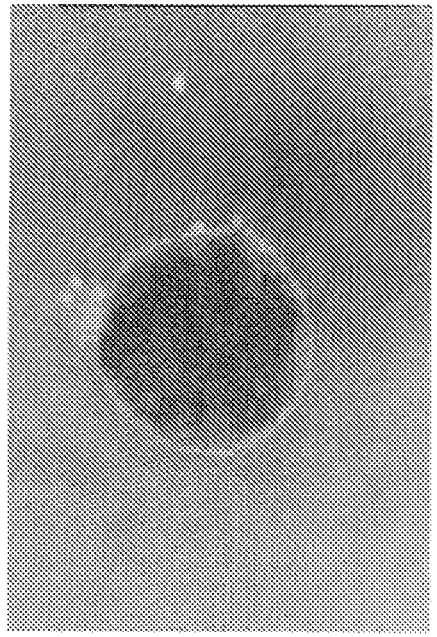
LOW OCT4 MAPC AGGREGATE
DIFF BASAL MEDIA, 21% O₂

NON-STATIC SUSPENSION CULTURE OF CELL AGGREGATES

RELATED APPLICATIONS

This application claims priority to U.S. Provisional Application No. 61/376,508, filed Aug. 24, 2010, which is incorporated herein by reference.

FIELD OF THE INVENTION

The invention is directed to cell culture compositions comprising a high concentration of cell aggregates and methods for making the high concentration of cell aggregates. The aggregates may comprise stem cell cells. Stem cells may include cells that are not embryonic stem cells, germ cells, or embryonic germ cells, and that express one or more markers of pluripotency. The cells may differentiate into cell types of at least two of ectodermal, endodermal, and mesodermal embryonic germ layers.

BACKGROUND OF THE INVENTION

Stem Cell Large Scale Culture

With the growing potential of stem cells for applications in cellular therapy and drug toxicity screening, there is an increasing need for the design of robust bioprocesses for their scalable expansion and differentiation. Thus, to meet the clinical need of ~$10^9$-$10^{10}$ cells per treatment, bioreactors of working volumes in the range of 100 ml to a few liters would be needed.

Suspension culture has been used in the expansion and differentiation of murine and human embryonic stem cells (ESC) by cultivating them as aggregates or on microcarriers (Abranches et al. 2007; Cameron et al. 2006; Cormier et al. 2006; Dang et al. 2004; Fok and Zandstra 2005; Krawetz et al. 2009; Lock and Tzanakakis 2009; Oh et al. 2009; zur Nieden et al. 2007). It is also possible to culture adult stem cells, such as hematopoietic stem and progenitor cells (Li et al. 2006), neural stem cells (Gilbertson et al. 2006) and mesenchymal stem cells (MSCs) (Frauenschuh et al. 2007; Yu et al. 2009) in suspension. Most studies involving MSCs have either been with cells seeded on microcarriers (Frauenschuh et al. 2007) or embedded within 3D polymeric scaffolds (Zhao and Ma 2005). In a recent study, the culture of MSCs as multi-cellular three-dimensional (3D) aggregates was demonstrated as another mode for culture in suspension (Frith et al. 2009). Aside from the benefit of large-scale cell production in a spinner culture system, there is increasing evidence of a significantly better recapitulation of the in-vivo phenotype and biological response in 3D aggregates than in traditional two-dimensional (2D) monolayer culture methods. This is thought to be due to differences in cell-cell and cell-matrix interactions, cell shape, spatial gradients, leading to differences in gene and protein expression. Thus, the potential applications of these 3D systems also extend to developing 'biomemetic' 3D tissues/organoids and as a in-vitro model for studying differentiation, organogenesis, migration, tumor biology, and in high-throughput drug screening (Griffith and Swartz 2006; Keller et al. 2006; Liu et al. 2009; Ong et al. 2009; Pampaloni et al. 2007; Yamada and Cukierman 2007).

SUMMARY OF THE INVENTION

The inventors have discovered that stem cell aggregates, even if formed in static culture, can continue to increase in size when further cultured in non-static conditions, such as stirred suspension. The fact that these starting aggregates can continue to grow under these conditions shows that growth in non-static cell culture is not disruptive to cellular proliferation and growth of the cells as aggregates. The fact that this can be done now allows the production of high density stem cell cultures, such as are practical and desirable for clinical applications. Accordingly, embodiments of the invention include, but are not limited to, those below.

The invention provides a cell culture composition comprising aggregates of stem cells in non-static cell culture wherein the cell density can range from about $5 \times 10^4$ cells/ml to $10^8$ cells/ml.

The high density cultures can be inoculated with aggregates formed from, e.g., embryoid bodies. In these bodies, the maximum dimensions of the aggregates can be about 500 µm. The maximum number of cells/aggregate can be about 25,000.

In the non-static cultures, the inoculated (initial) aggregates can grow up to an average maximum of about 50,000 cells in each aggregate with an average maximum diameter of about 1 mm.

In one embodiment the aggregates formed in the non-static culture range in size from about 10 µm-1 mm.

In one embodiment the density of cells in the non-static cell culture ranges from about $5 \times 10^4$-$10^8$ cells/ml.

In one embodiment, the volume of the non-static cell culture ranges from about 10 ml-20000 L.

In one embodiment, the non-static cell cultures are non-adherent.

Types of non-adherent cell cultures include, but are not limited to, laboratory spinner flasks, shaker flasks and mixing tank bioreactors.

The invention further provides methods for making the above compositions. The methods comprise inoculating aggregates into non-static cell culture conditions, and culture-expanding those aggregates until they reach a desired size (number of cells) and the number of cells/ml is a desired density.

Accordingly, the invention is directed to a method for making a cell culture composition by introducing aggregates of cells into non-static cell culture in which the average number of cells per aggregate increases.

The range of increase can be from about 2 fold up to 5,000 fold. For example, an aggregate with a starting average starting number of 10 cells can grow up to aggregates with an average number of cells of 50,000 or even more.

Accordingly, the highest range would be around 5,000×. In this case, starting with an aggregate of about 10 cells (on average) and increasing to an aggregate of about 50,000 cells (on average) is a 5,000× increase. Starting with an aggregate of about 100 cells and increasing to an aggregate of about 50,000 cells is about a 500× increase. Starting with an aggregate of about 1,000 cells and increasing to an aggregate of about 50,000 cells would be a 50× increase. Starting with an aggregate of about 5,000 cells and increasing to an aggregate of about 50,000 cells is a 10× increase. Thus, one may begin with aggregates of a lower limit of about 10 cells to an upper limit even of about 25,000 cells. One may then take each of these through the upper limit of about 50,000 cells or to aggregates of sizes less than 50,000 cells. The smaller the aggregate that one begins with, the higher the fold increase necessary to obtain aggregates of very large size, such as 25,000 to 50,000 cells. The larger the aggregate that one begins with, the less fold increase would be necessary.

Accordingly, the average cell number in each of the aggregates that remain as intact aggregates in suspension culture can be in the range of (per aggregate) 5,000, 6,000, 7,000, 8,000, 9,000, 10,000, 11,000, 12,000, 13,000, 14,000, 15,000, 16,000, 17,000, 18,000, 19,000, 20,000, about 20,000 to 25,000, about 25,000 to 30,000, about 30,000 to 35,000, about 35,000 to 40,000, about 40,000 to 45,000, about 45,000 to 50,000, and possibly more. Ranges in between are also included (e.g., 21,000, 22,000, etc.). With an initial average cell number of about 1,000, the invention covers a range of fold increases up to about 50 fold (i.e., about 50,000 cells per aggregate), such as 10× to 15×, 15× to 20×, 20× to 25×, 25× to 30×, 30× to 35×, 35× to 40×, 40× to 45×, 45× to 50×, and higher.

In one embodiment the aggregates formed in the non-static culture range in size from 10 um-1 mm.

In one embodiment the density of cells in the non-static cell culture ranges from $5 \times 10^4$-$10^8$ cells/ml.

In one embodiment, the volume of the non-static cell culture ranges from 10 ml-20000 L.

In one embodiment, the non-static cell cultures are non-adherent.

Types of non-adherent cell cultures include, but are not limited to, laboratory culture flasks, spinner flask, shaker flasks and mixing tank bioreactors.

The methods further include making a pharmaceutical composition by admixing a pharmaceutically-acceptable carrier with the aggregates produced in the methods above.

The methods further include making cells derived from aggregates of cells by dis-aggregating the aggregates produced in the methods above.

The methods further include making a cell culture composition by introducing, into a culture medium, cells derived from the aggregates produced in the methods above.

The methods further include making a pharmaceutical composition by admixing a pharmaceutically-acceptable carrier with cells derived from the aggregates produced in the methods above.

The methods further include making a differentiated cell by exposing the aggregates produced in the methods above to conditions producing the differentiated cell.

The methods further include making a pharmaceutical composition by admixing a pharmaceutically-acceptable carrier with a differentiated cell produced by exposing the aggregates produced in the methods above to conditions producing the differentiated cell.

The methods further include making a differentiated cell by exposing a cell derived by dis-aggregating the aggregates produced in the methods above to conditions producing the differentiated cell.

The invention further provides a method for making a pharmaceutical composition by admixing a differentiated cell with a pharmaceutically-acceptable carrier, the cell having been produced by exposing cells derived by dis-aggregating the aggregates produced in the methods above to conditions producing the differentiated cell.

The methods further include administering to a subject aggregates produced in the methods above.

The methods further include administering to a subject a pharmaceutical composition comprising a pharmaceutically-acceptable carrier and aggregates produced in the methods above.

The methods further include administering to a subject cells derived by dis-aggregating the aggregates produced in the methods above.

The methods further include administering to a subject a pharmaceutical composition comprising a pharmaceutically-acceptable carrier and cells derived by dis-aggregating the aggregates produced in the methods above.

The methods further include administering to a subject a differentiated cell produced by exposing the aggregates produced in the methods above to conditions producing the differentiated cell.

The methods further include administering to a subject a pharmaceutical composition comprising a pharmaceutically-acceptable carrier and a differentiated cell, the differentiated cell produced by exposing the aggregates produced in the methods above to conditions producing the differentiated cell.

The methods further include administering to a subject a differentiated cell produced by exposing cells derived by dis-aggregating the aggregates produced in the methods above to conditions producing the differentiated cell.

The methods further include administering to a subject a pharmaceutical composition comprising a pharmaceutically-acceptable carrier and a differentiated cell, the differentiated cell produced by exposing cells derived by dis-aggregating the aggregates produced in the methods above to conditions producing the differentiated cell.

The methods further include identifying an active agent by contacting the aggregates produced in the methods above with an agent and detecting the effect of the agent on the cells in the aggregates.

The invention further provides a method of identifying an active agent by contacting cells derived by dis-aggregating the aggregates produced in the methods above with an agent and detecting the effect of the agent on the cells derived from the aggregates.

The methods further include a method of treating a disorder in a subject in need of treatment by administering a therapeutically effective amount of the aggregates produced in the methods above.

The methods further include a method of treating a disorder in a subject in need of treatment by administering a therapeutically effective amount of a pharmaceutical composition comprising a pharmaceutically-acceptable carrier and the aggregates produced in the methods above.

The methods further include a method of treating a disorder in a subject in need of treatment by administering a therapeutically effective amount of cells derived by dis-aggregating the aggregates produced in the methods above.

The methods further include a method of treating a disorder in a subject in need of treatment by administering a therapeutically effective amount of a pharmaceutical composition comprised of a pharmaceutically-acceptable carrier and cells derived by dis-aggregating the aggregates produced in the methods above.

The methods further include a method of treating a disorder in a subject in need of treatment by administering a therapeutically effective amount of a differentiated cell produced by exposing the aggregates produced in the methods above to conditions producing the differentiated cell.

The methods further include a method of treating a disorder in a subject in need of treatment by administering a therapeutically effective amount of a pharmaceutical composition comprising a pharmaceutically-acceptable carrier and a differentiated cell, said differentiated cell produced by exposing the aggregates produced in the methods above to conditions producing the differentiated cell.

The methods further include a method of treating a disorder in a subject in need of treatment by administering a therapeutically effective amount of a differentiated cell produced by exposing cells derived by dis-aggregating the aggregates produced in the methods above to conditions producing the differentiated cell.

The methods further include a method of treating a disorder in a subject in need of treatment by administering a therapeutically effective amount of a pharmaceutical composition comprising a pharmaceutically-acceptable carrier and a differentiated cell produced by exposing cells derived by dis-aggregating the aggregates produced in the methods above to conditions producing the differentiated cell.

According to the statements above, the aggregate of cells may comprise cells that are not embryonic stem cells, embryonic germ cells, or germ cells, can differentiate into cell types of at least two of the endodermal, ectodermal and mesodermal embryonic lineages, and/or express one or more pluripotency markers.

The cells to which the invention is directed may express pluripotency markers, such as oct4. They may also express markers associated with extended replicative capacity, such as telomerase. Other characteristics of pluripotency can include the ability to differentiate into cell types of more than one germ layer, such as two or three of ectodermal, endodermal, and mesodermal embryonic germ layers. Such cells may or may not be immortalized or transformed in culture. The cells may be highly expanded without being transformed and also maintain a normal karyotype. For example, in one embodiment, the non-embryonic stem, non-germ cells may have undergone at least 10-40 cell doublings in culture, such as 50, 60, or more, wherein the cells are not transformed and have a normal karyotype. The cells may differentiate into at least one cell type of each of two of the endodermal, ectodermal, and mesodermal embryonic lineages and may include differentiation into all three. Further, the cells may not be tumorigenic, such as not producing teratomas. If cells are transformed or tumorigenic, and it is desirable to use them for infusion, such cells may be disabled so they cannot form tumors in vivo, as by treatment that prevents cell proliferation into tumors. Such treatments are well known in the art.

Cells include, but are not limited to, the following numbered embodiments:

1. Isolated expanded non-embryonic stem, non-germ cells, the cells having undergone at least 10-40 cell doublings in culture, wherein the cells express oct4, are not transformed, and have a normal karyotype.

2. The non-embryonic stem, non-germ cells of 1 above that further express one or more of telomerase, rex-1, rox-1, or sox-2.

3. The non-embryonic stem, non-germ cells of 1 above that can differentiate into at least one cell type of at least two of the endodermal, ectodermal, and mesodermal embryonic lineages.

4. The non-embryonic stem, non-germ cells of 3 above that further express one or more of telomerase, rex-1, rox-1, or sox-2.

5. The non-embryonic stem, non-germ cells of 3 above that can differentiate into at least one cell type of each of the endodermal, ectodermal, and mesodermal embryonic lineages.

6. The non-embryonic stem, non-germ cells of 5 above that further express one or more of telomerase, rex-1, rox-1, or sox-2.

7. Isolated expanded non-embryonic stem, non-germ cells that are obtained by culture of non-embryonic, non-germ tissue, the cells having undergone at least 40 cell doublings in culture, wherein the cells are not transformed and have a normal karyotype.

8. The non-embryonic stem, non-germ cells of 7 above that express one or more of oct4, telomerase, rex-1, rox-1, or sox-2.

9. The non-embryonic stem, non-germ cells of 7 above that can differentiate into at least one cell type of at least two of the endodermal, ectodermal, and mesodermal embryonic lineages.

10. The non-embryonic stem, non-germ cells of 9 above that express one or more of oct4, telomerase, rex-1, rox-1, or sox-2.

11. The non-embryonic stem, non-germ cells of 9 above that can differentiate into at least one cell type of each of the endodermal, ectodermal, and mesodermal embryonic lineages.

12. The non-embryonic stem, non-germ cells of 11 above that express one or more of oct4, telomerase, rex-1, rox-1, or sox-2.

13. Isolated expanded non-embryonic stem, non-germ cells, the cells having undergone at least 10-40 cell doublings in culture, wherein the cells express telomerase, are not transformed, and have a normal karyotype.

14. The non-embryonic stem, non-germ cells of 13 above that further express one or more of oct4, rex-1, rox-1, or sox-2.

15. The non-embryonic stem, non-germ cells of 13 above that can differentiate into at least one cell type of at least two of the endodermal, ectodermal, and mesodermal embryonic lineages.

16. The non-embryonic stem, non-germ cells of 15 above that further express one or more of oct4, rex-1, rox-1, or sox-2.

17. The non-embryonic stem, non-germ cells of 15 above that can differentiate into at least one cell type of each of the endodermal, ectodermal, and mesodermal embryonic lineages.

18. The non-embryonic stem, non-germ cells of 17 above that further express one or more of oct4, rex-1, rox-1, or sox-2.

19. Isolated expanded non-embryonic stem, non-germ cells that can differentiate into at least one cell type of at least two of the endodermal, ectodermal, and mesodermal embryonic lineages, said cells having undergone at least 10-40 cell doublings in culture.

20. The non-embryonic stem, non-germ cells of 19 above that express one or more of oct4, telomerase, rex-1, rox-1, or sox-2.

21. The non-embryonic stem, non-germ cells of 19 above that can differentiate into at least one cell type of each of the endodermal, ectodermal, and mesodermal embryonic lineages.

22. The non-embryonic stem, non-germ cells of 21 above that express one or more of oct4, telomerase, rex-1, rox-1, or sox-2.

The cells described above can be prepared from any desirable tissue source, including, but not limited to, bone marrow, umbilical cord blood, umbilical cord matrix, peripheral blood, placenta, placental blood, muscle, brain, kidney, and other solid organs. They can also be derived from excreted fluids, such as urine and menstrual blood.

In one embodiment, the cells are derived from human tissue.

39. In one embodiment, the cells in the aggregate and cells derived from the aggregate express one or more of oct3/4, telomerase, rex-1, rox-1, nanog, GATA6 and sox-2.

40. In one embodiment, the cells in the aggregate and cells derived from the aggregate can differentiate into cell types of all three of the endodermal, ectodermal, and mesodermal embryonic lineages.

41. In one embodiment, the differentiated cell, produced by differentiating the aggregate or cells derived from the aggregate, expresses an endodermal differentiation marker.

42. In one embodiment, the differentiated cell, produced by differentiating the aggregate or cells derived from the aggregate, expresses an ectodermal differentiation marker.

43. In one embodiment, the differentiated cell, produced by differentiating the aggregate or cells derived from the aggregate, expresses a mesodermal differentiation marker.

44. In one embodiment, the differentiated cell phenotype, produced by differentiating the aggregate or cells derived from the aggregate, is characteristic of cells selected from the group consisting of hepatocytes, beta islet cells, and neurons.

45. In one embodiment, the aggregates are about 100 um-800 um and are at a density in culture of $10^5$-$10^8$ cells/ml.

46. The invention further provides the compositions herein, wherein starting cells are aggregated by the hanging drop method or forced aggregation method.

47. The invention further provides the methods herein, wherein the disorder is a liver disease or disorder, GVHD, myocardial infarction, congestive heart failure, diabetes, hematopoietic transplant, traumatic brain injury, spinal cord injury or stroke.

48. The invention further provides the methods herein, wherein the disorder involves damaged tissue and the tissue is one or more of cardiac, neuronal, ocular, cartilage, bone, skeletal muscle, smooth muscle, bone marrow, spleen, liver, lung, brain, immune system, connective, blood vessel, pancreas, CNS, PNS and kidney tissue.

In the above statements of the invention, cells derived from the aggregate may retain the differentiation capacity and/or express the pluripotency markers (e.g., as listed above) of the aggregated cells.

There is little expression of early endoderm markers HNF3b and Goosecoid (Gsc) and no expression of mature endoderm markers like AFP, albumin, Alpha-1-Antitrypsin (AAT) and Tyrosine amino transferase (TAT) in 3D MAPC aggregates similar to MAPCs 2D.

FIG. 5 shows low oct3/4 MAPC aggregates formed from low oct3/4 MAPCs in 2D culture in MAPC medium and 5% oxygen in 7 days. Upon spontaneous differentiation in differentiation basal media and 21% oxygen, aggregates differentiated to cells that appeared like adipocytes and fibroblasts by morphology.

Figure 1:
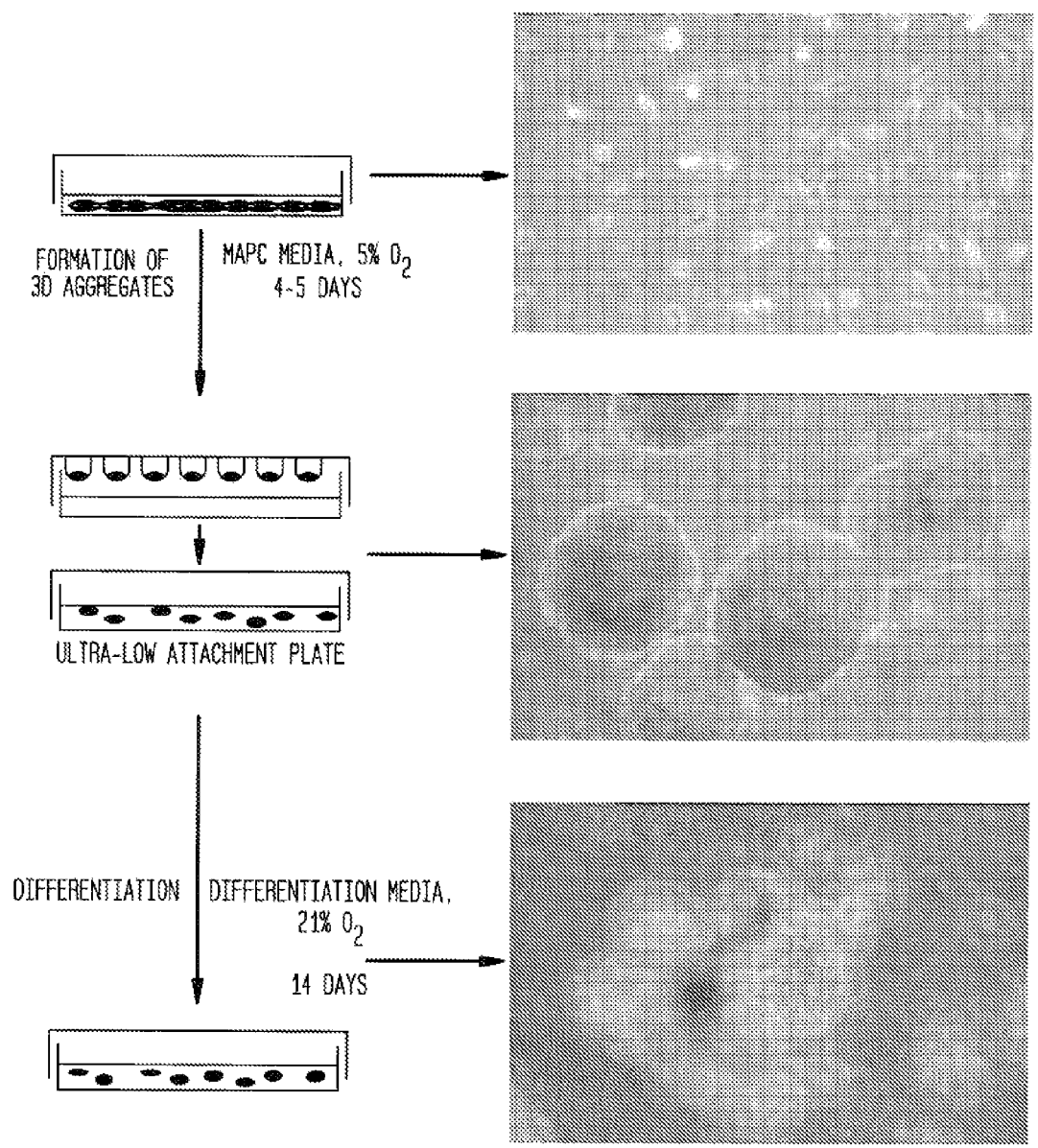
FIG. 1 shows the hanging drop method for forming aggregates from rat MAPCs in monolayer (2D) culture and subsequent differentiation. After 4-5 days of aggregate formation in the hanging drop in MAPC media and 5% oxygen, cell aggregates are transferred to the ultra-low attachment plate for differentiation in corresponding differentiation media. The right panel illustrates the morphology of the cells in 2D monolayer, undifferentiated cell aggregates, and then differentiated cell aggregates.
Figure 2:
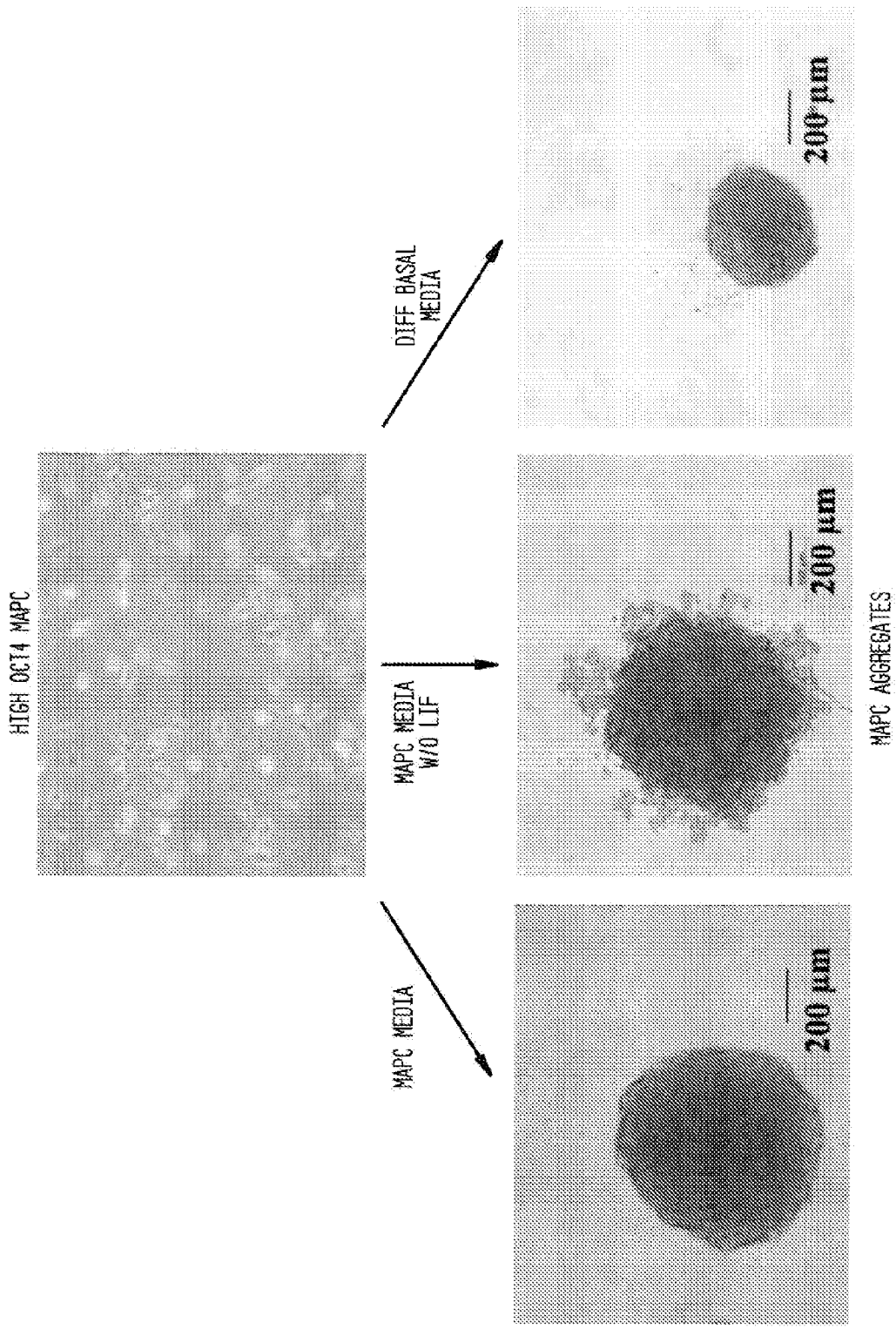
FIG. 2 shows aggregates formed from rat MAPC under different media conditions. Under optimum MAPC media conditions, the aggregates grow up into spherical clusters with well defined boundary. Withdrawal of LIF from MAPC media induces formation of aggregates with irregular boundary corresponding to early signs of differentiation. In differentiation basal media, the cell aggregates are much smaller due to non-optimal growth conditions.
Figure 3:
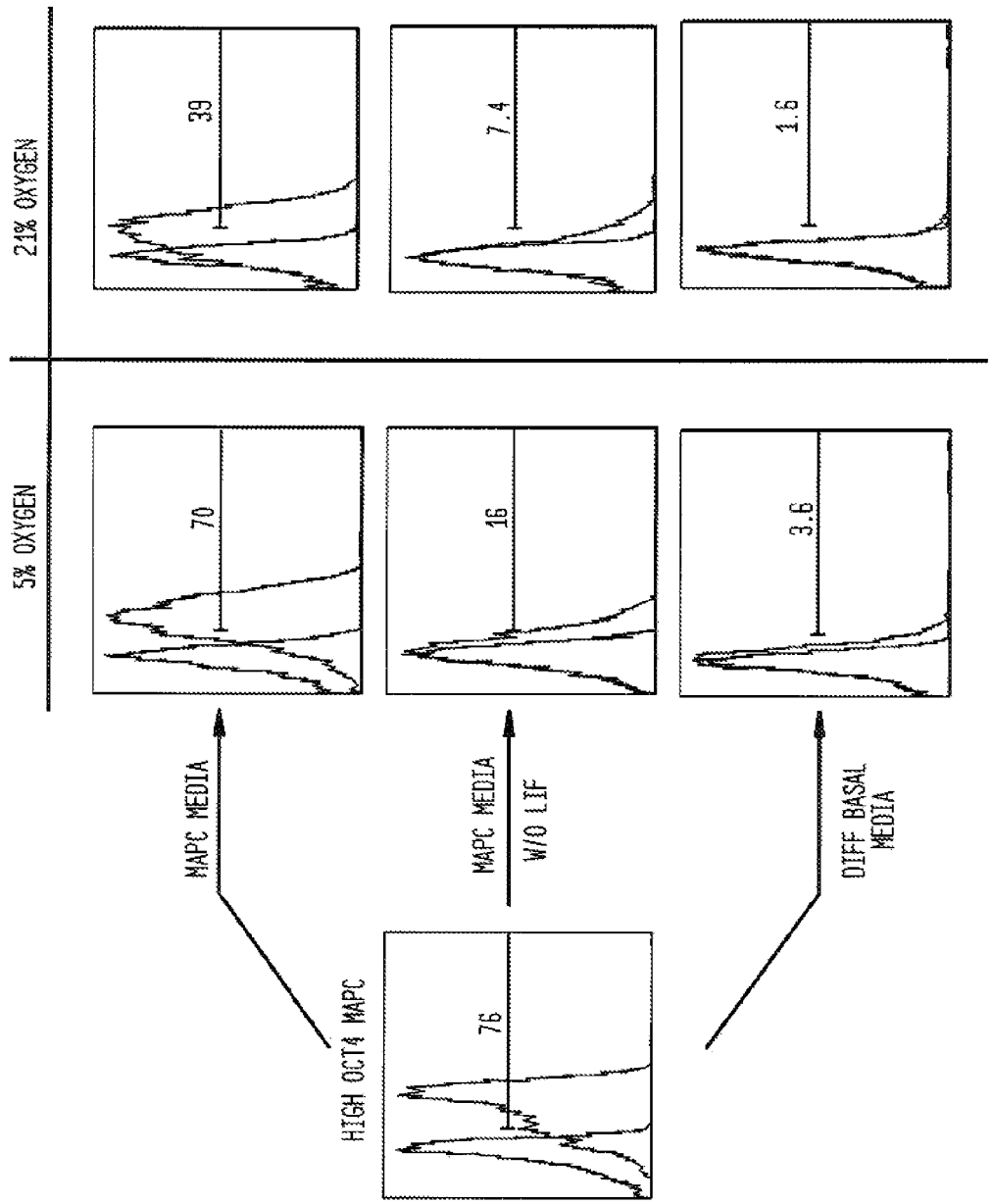
FIG. 3 shows the percentage of cells expressing oct3/4 (transcription factor associated with the undifferentiated status of MAPCs). Out of the 76% of cells that expressed oct3/4 in 2D monolayer, 70% still retained the expression of oct3/4 in the MAPC aggregates when they were formed in MAPC media and 5% oxygen. Other conditions were different media compositions: —MAPC media without LIF, differentiation basal media, and choice of oxygen levels—5% (hypoxic) or 21% (normoxic).
Figure 4:
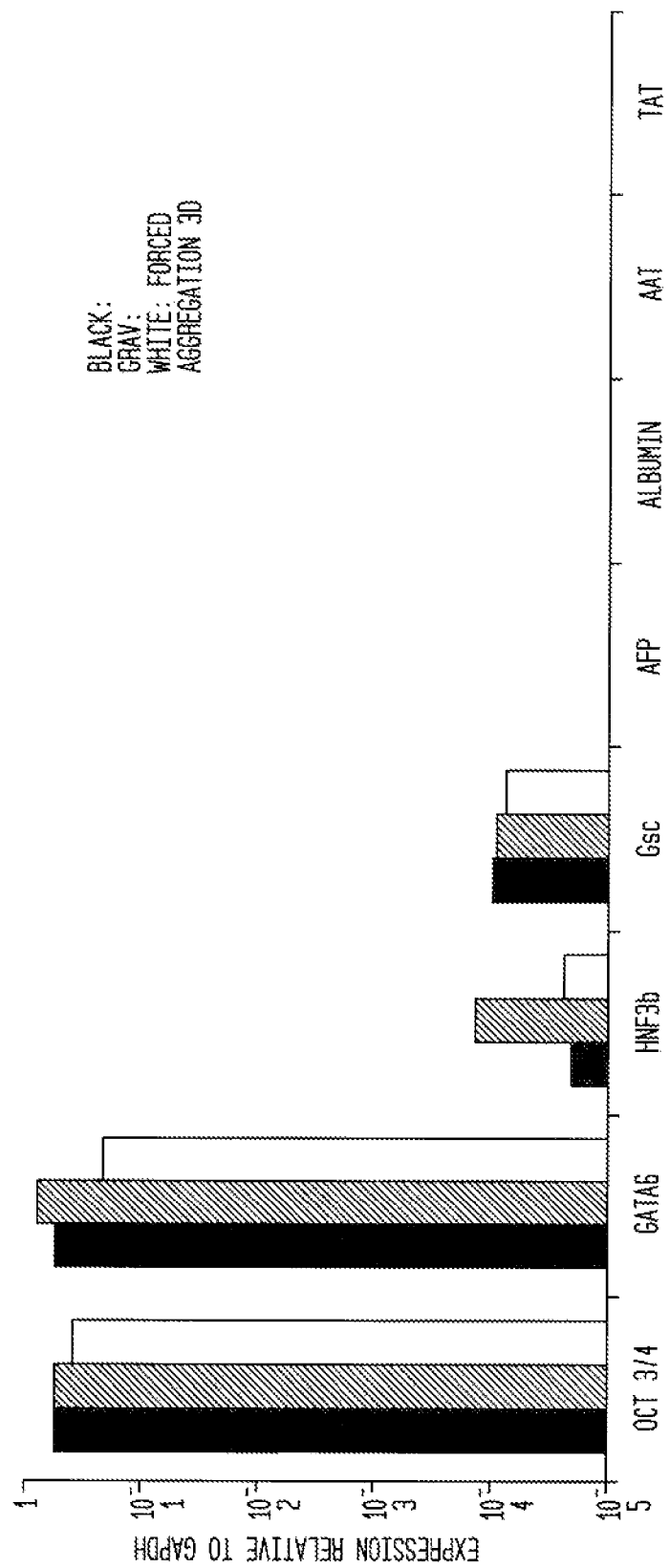
FIG. 4 shows a QRT-PCR comparison of expression of several undifferentiated and differentiated markers in MAPC 2D and 3D cultures formed by the hanging drop method and forced aggregation method. The expression of oct3/4 and GATA6 are both comparable between 2D MAPCs and 3D MAPC aggregates irrespective of the method of formation.
Figure 6:
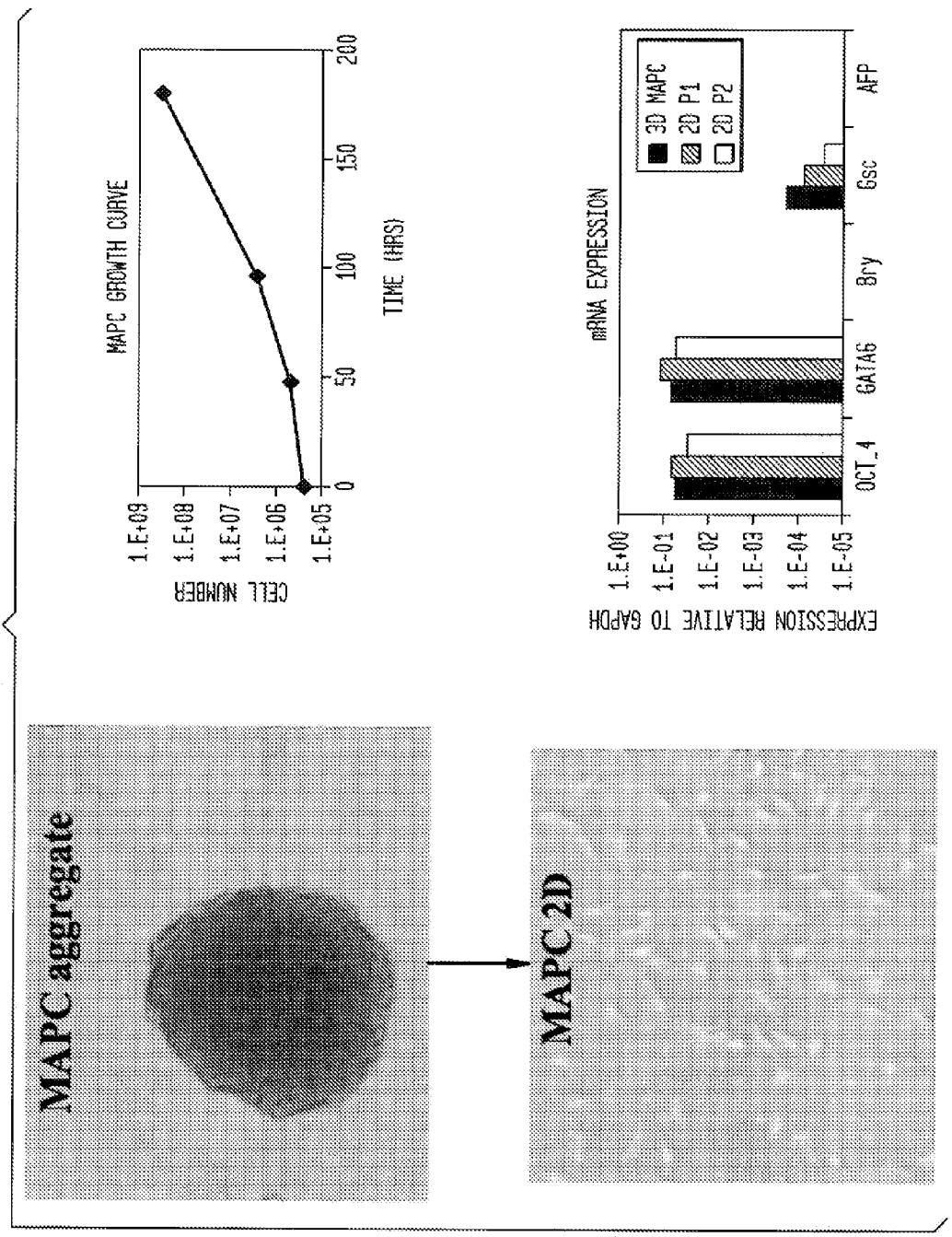

FIG. 6 shows high oct3/4 MAPC aggregates trypsinized and replated onto fibronectin-coated dishes in MAPC medium and 5% oxygen. The morphology of cells are typical of MAPCs, they are capable of undergoing expansion illustrated by the increase in cell number with time and retain the expression of MAPC markers oct3/4 and GATA6 at passage 1 (2D P1) and passage 2 (2D P2) after replating at levels expressed by MAPCs aggregates they came from. There is little or no expression of early differentiated markers like Goosecoid (Gsc) or Brachyury (Bry) and no expression of more mature markers like Alpha-fetoprotein (AFP).

Figure 7:
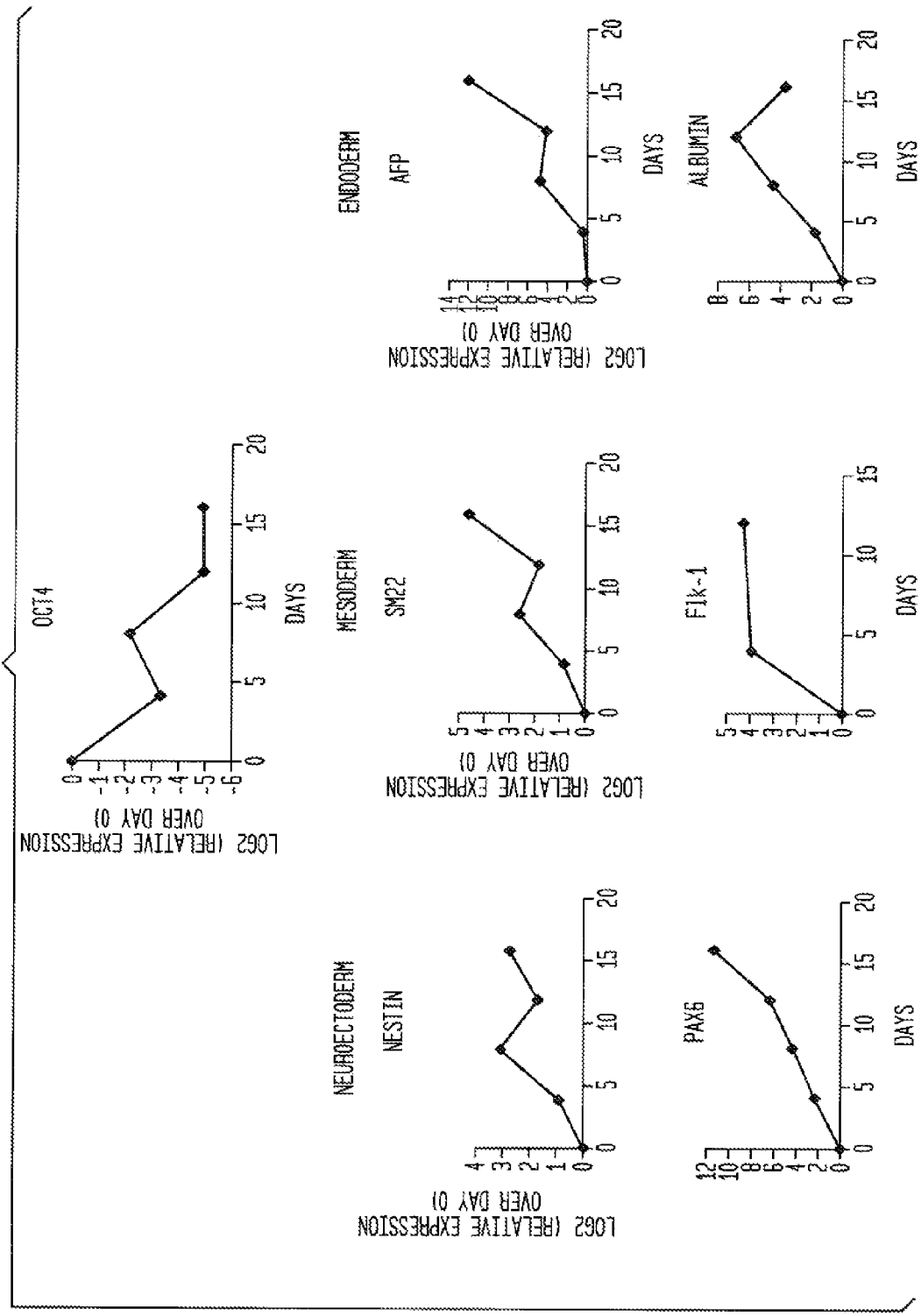

FIG. 7 shows spontaneous multi-lineage differentiation of MAPC aggregates in differentiation basal medium with 2% serum. The levels of oct3/4 goes down corresponding to differentiation and increase in expression of markers of the three germ layers are observed-Nestin, Pax6 (neuroectoderm), SM22, Flk-1 (mesoderm), AFP, Albumin (endoderm).

Figure 8:
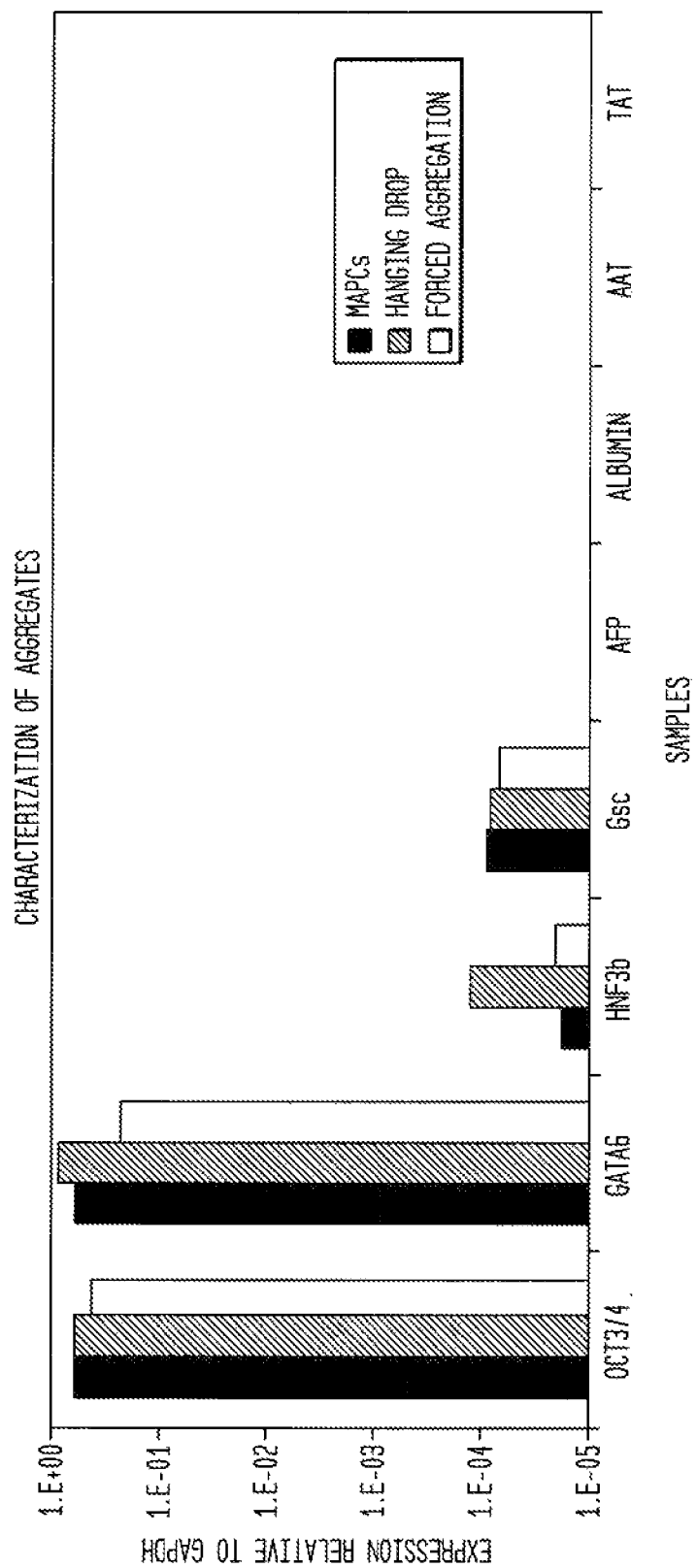

FIG. 8 shows characterization of MAPC aggregates using QRT-PCR.

Figure 9:
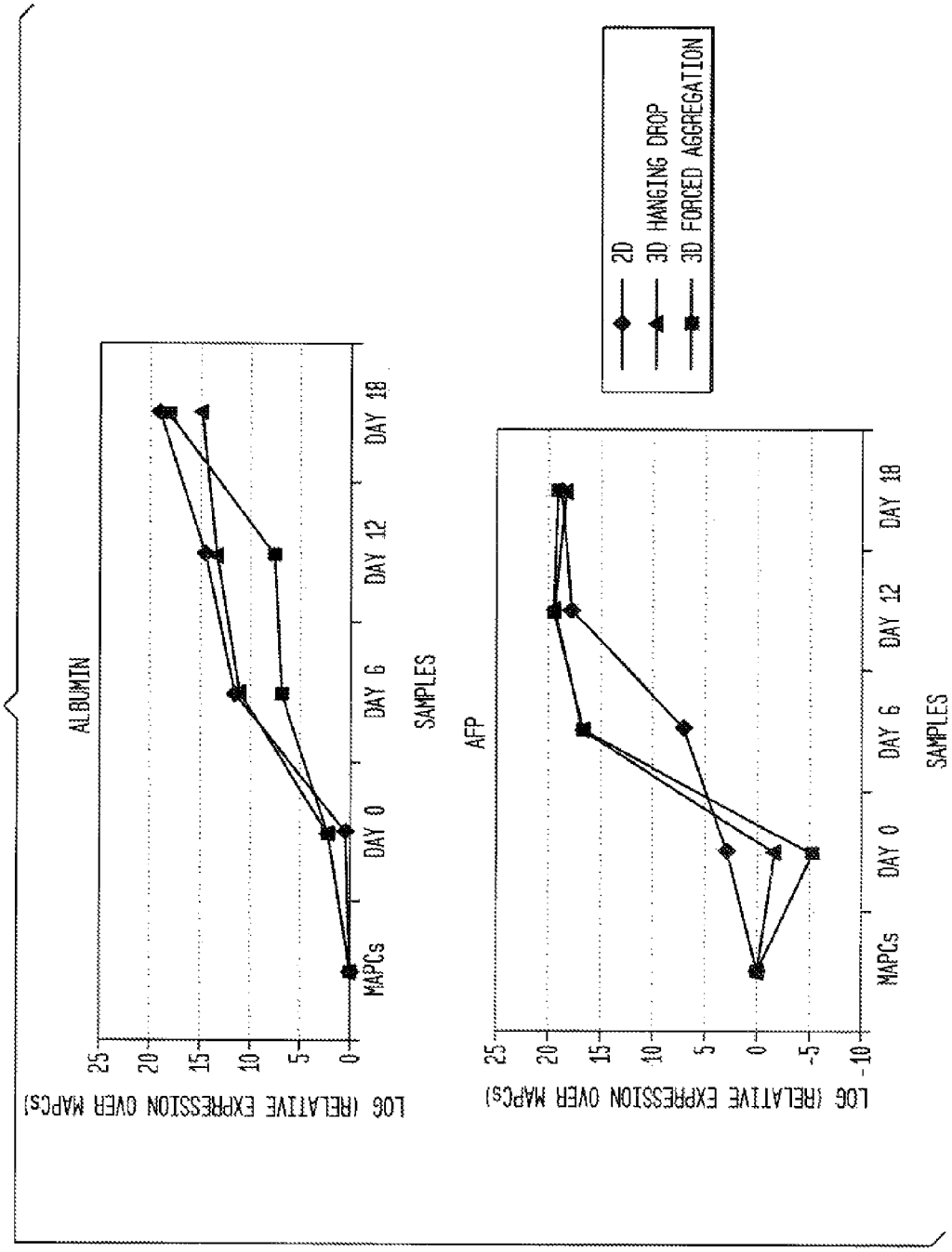

FIG. 9 shows results of differentiation using a multi-step protocol.

Figure 10:
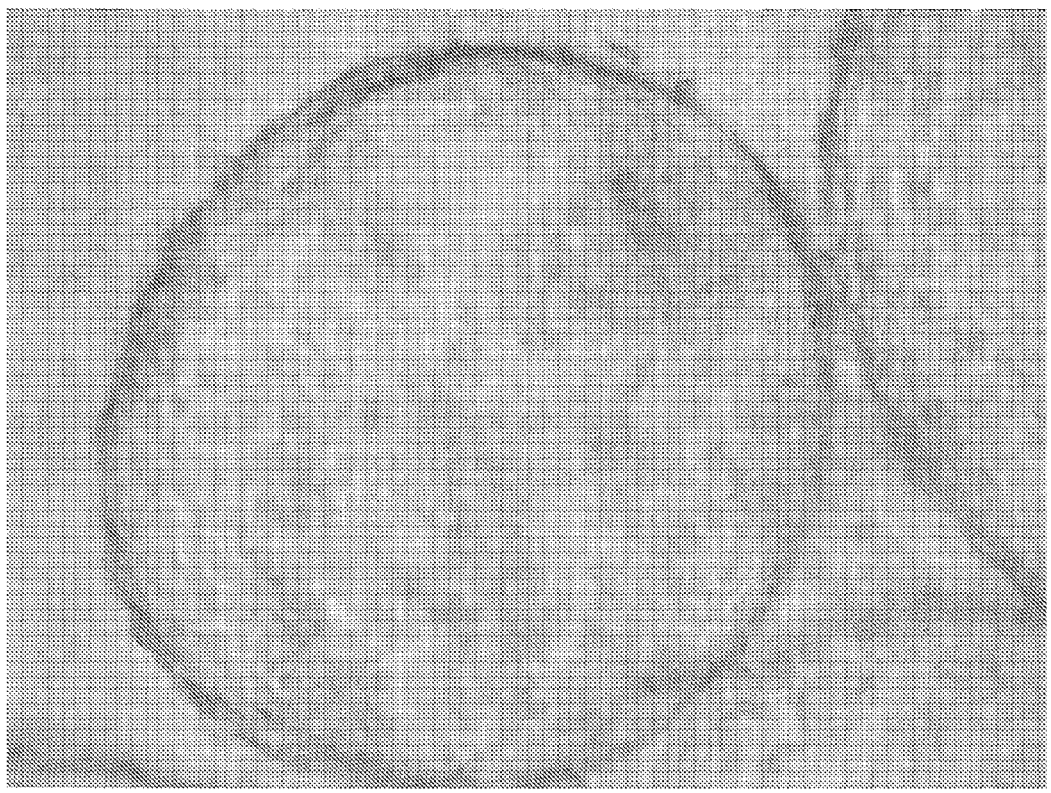

FIG. 10 shows morphology of aggregates after 21 days of differentiation (10×).

Figure 11A:
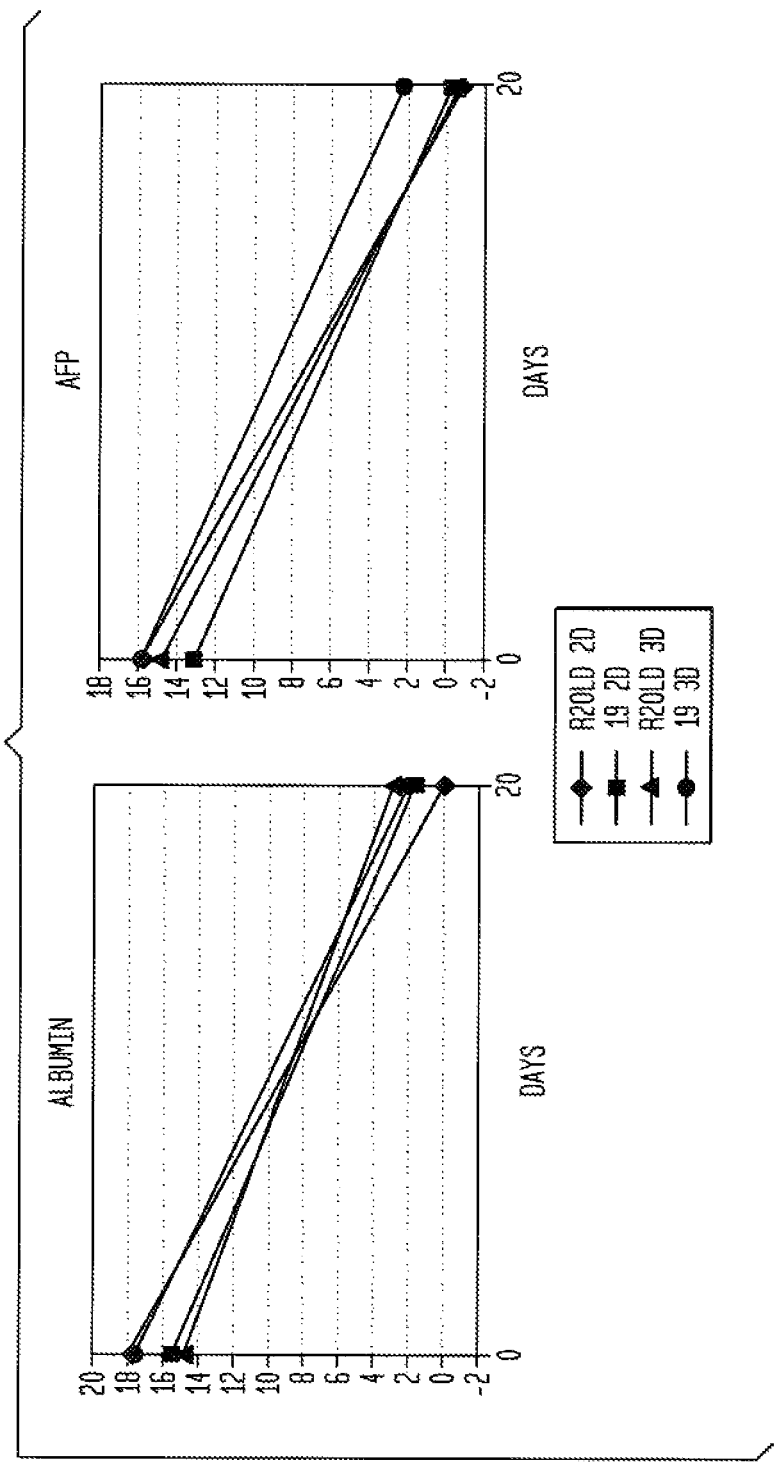
Figure 11B:
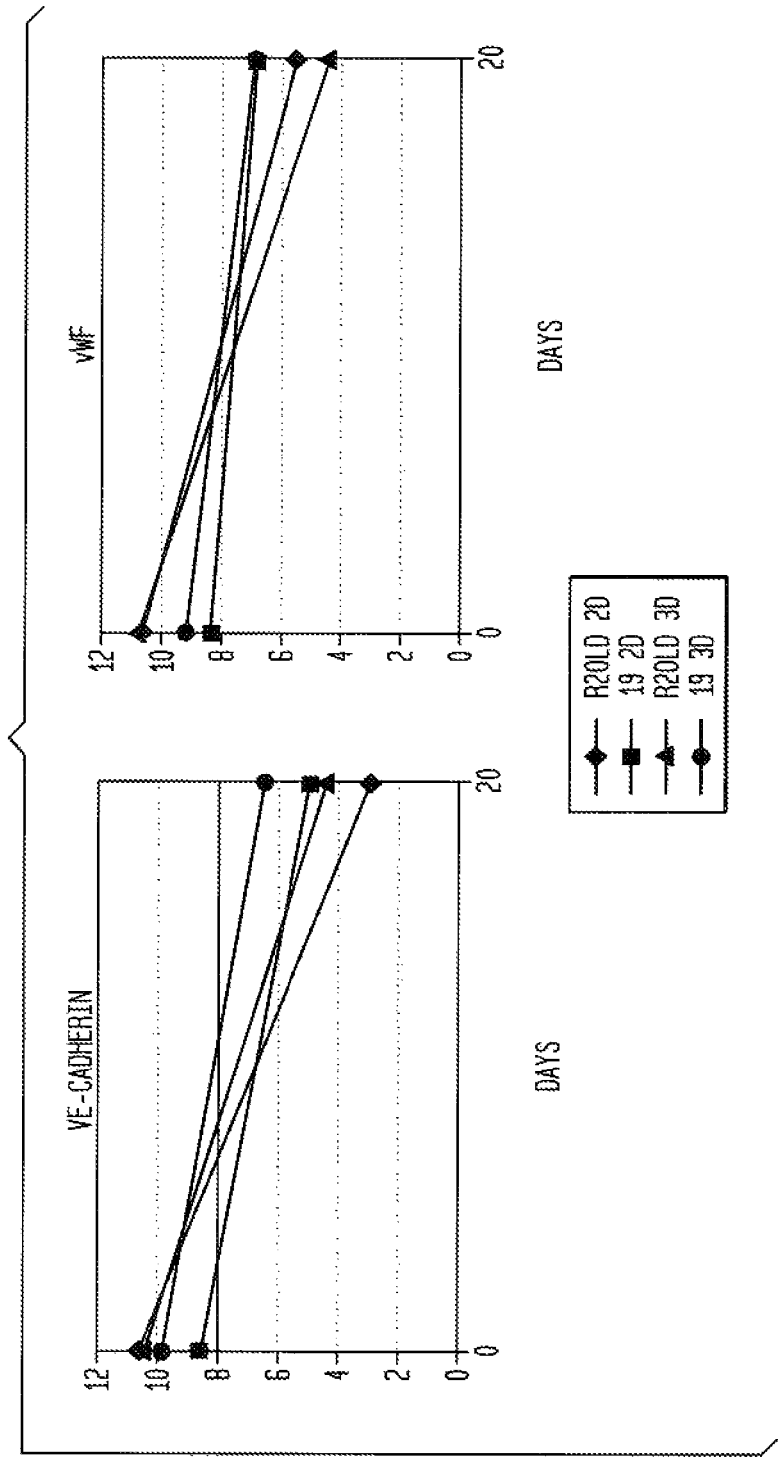
Figure 11C:
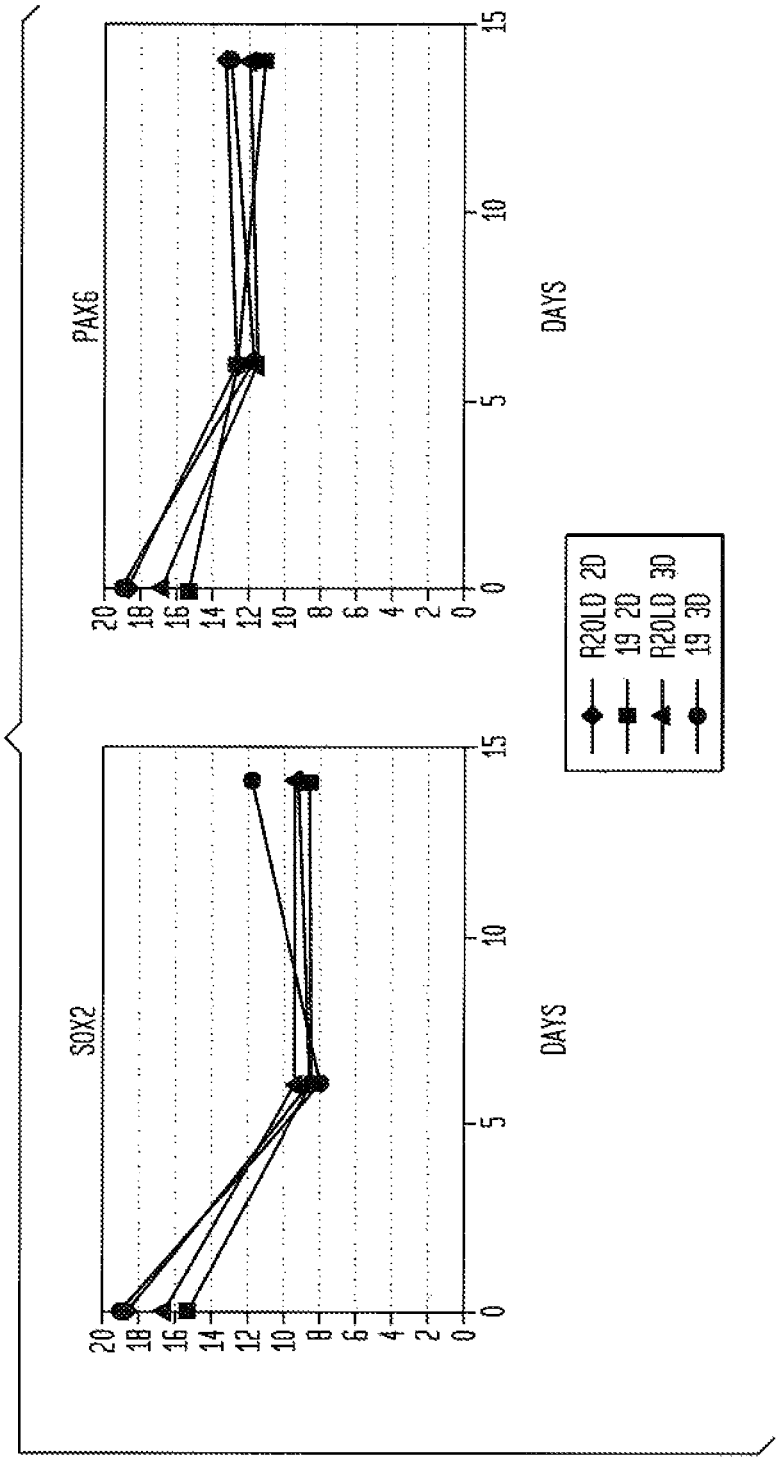

FIG. 11 shows directed differentiation to hepatocytes (A), endothelial cells (B), and neural precursors (C), starting from rat MAPC lines R2old and 19 maintained undifferentiated in 2D vs. 3D conditions.

FIG. 12 shows aggregates retain MAPC phenotype. (a) Transcript level of pluripotency, primitive endoderm and differentiation markers of surface cultured (□/✿) and aggregates (Day 4, ▨/■) of MAPC (Data of 2 lines are shown for each). (b) Flow cytometric measurement of Oct4 protein in aggregates and surface cultured MAPC (negative isotype control and Oct4 antibody treated samples are shown in both cases) (c) Transcript level of Oct4 (▨) and AFP (■), and (d) Flow cytometric measurement of Oct4 in aggregates formed in 21% oxygen or in differentiation inducing conditions (negative isotype control and Oct4 antibody treated samples are shown in red and blue respectively).

FIG. 13 shows characterization of MAPC aggregates. a) Morphology of MAPC aggregates (Day 4), (scale bar 200 μm) (b) Change in aggregate size during the first 48 hr of aggregate formation (c) Cell proliferation during aggregate formation e) TEM section of MAPC aggregate (d) E-cadherin staining.

FIG. 14 shows static culture of MAPC aggregates. Change of (a) Oct4 and (b) AFP transcript levels in 16 day culture of (■/□) aggregate culture; (▲/△) aggregate in differentiation medium. Black and white symbols represent the different MAPC lines (c), (d) Flow cytometric measurement of Oct4 in MAPC aggregates on Day 16 in the two rat MAPC lines (negative isotype control and Oct4 antibody treated samples are shown in red and blue respectively).

FIG. 15 shows directed differentiation of aggregate derived MAPC (Day 16). (a) Transcript levels of neural progenitor markers Sox2, Nestin, Pax6 in neural differentiation (b) Transcript levels of endothelial markers Flk-1, Ve-Cadherin, vWF, enos in endothelial differentiation (c) Transcript expression of hepatocyte markers AFP, Albumin, AAT, TAT in hepatocyte differentiation (☐/▩): surface culture (▩/■): day 16 aggregate derived cells (Data from two different cell lines are shown for each, mean of n=3 differentiations)

FIG. 16 shows expansion of MAPC cell aggregates in spinner flasks. (a) Cell proliferation profile (b) Vital stain of MAPC aggregates (Day 4) (c) Transcript level of MAPC markers (■) Oct4; (▲) Rex1; (x) CD31; (●) Sall4; (♦) AFP (average of three spinner flask runs) (d) Flow cytometric measurement of Oct4 in MAPC aggregates at the end of spinner culture (day 4) and in control 2D culture (day 4) (negative isotype control and Oct4 antibody treated samples are shown in red and blue respectively) (e) Transcript level of hepatocyte markers in hepatocyte differentiation conditions in static culture starting from (☐): Day 0; (▩): Day 2; (■): Day 4 cells of spinner expansion culture.

Figure 17:
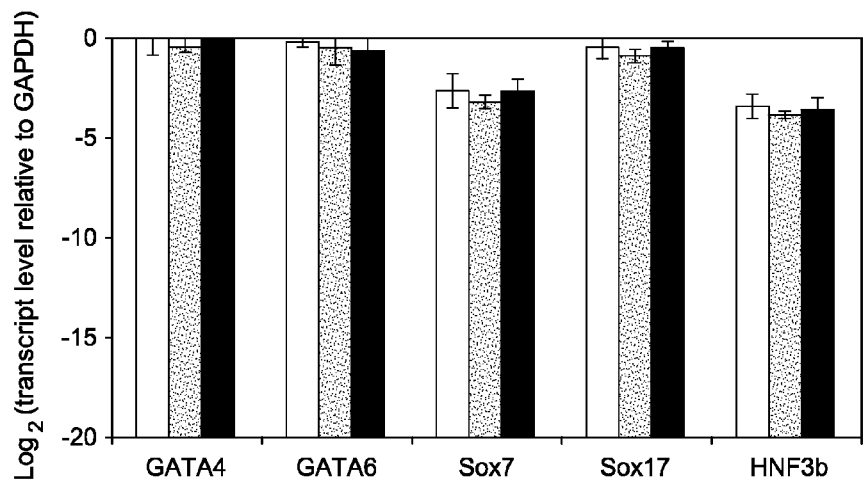

FIG. 17 shows transcript level of MAPC/primitive endoderm markers (☐): surface culture (▩): MAPC cell aggregate in static culture and (■): MAPC cell aggregate in suspension culture.

Figure 18A:
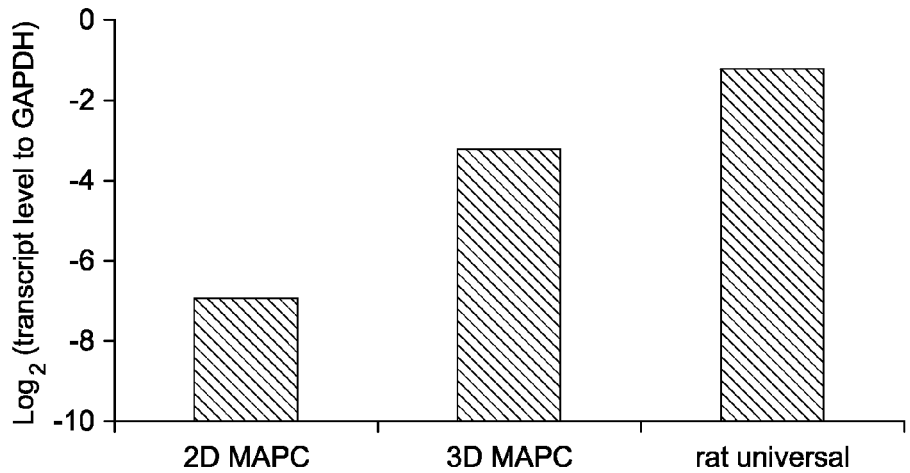
Figure 18B:
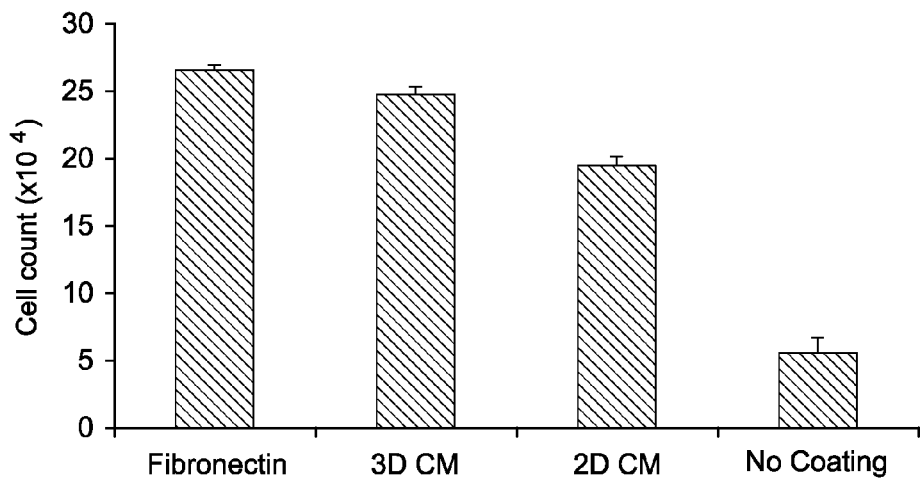

FIG. 18 shows (a) transcript level of fibronectin in surface culture (2D MAPCs), cell aggregate (3D MAPCs) and rat universal mRNA, and (b) growth of MAPCs on fibronectin or aggregate culture conditioned medium (3D CM) or surface culture conditioned medium (2D CM) coated plates or without coating.

Figure 19A:
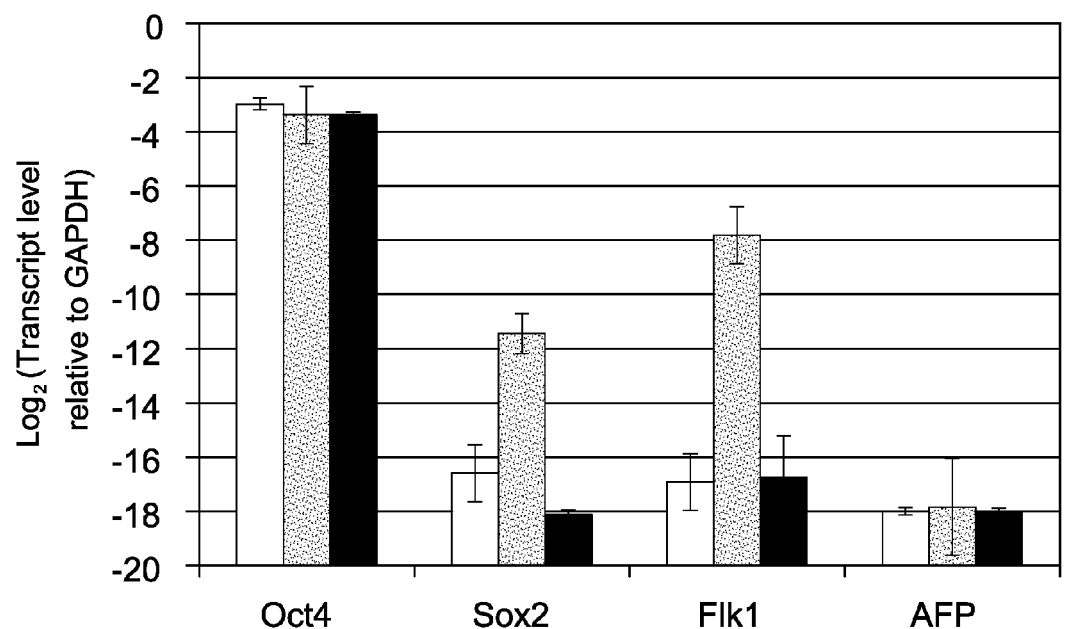
Figure 19B:
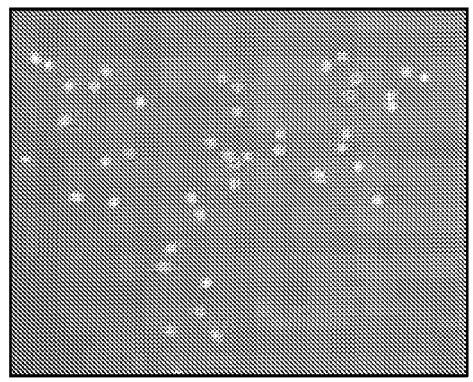
Figure 19C:
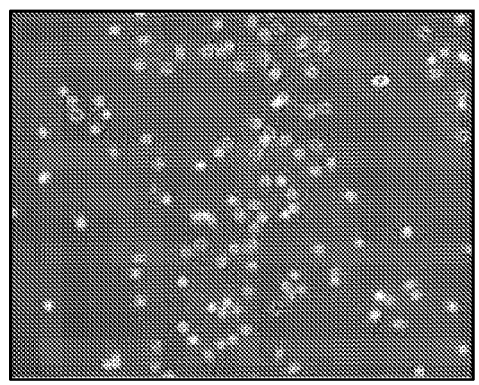

FIG. 19 shows replating of MAPC aggregates (A) transcript level of pluripotency and differentiation markers in surface cultured (☐), aggregates (Day 4, ■) and replated surface culture of aggregate derived cells (passage 2, ■) of MAPCs, (B) morphology of surface cultured MAPCs, and (C) morphology of replated surface culture of aggregate derived cells.

Figure 20:
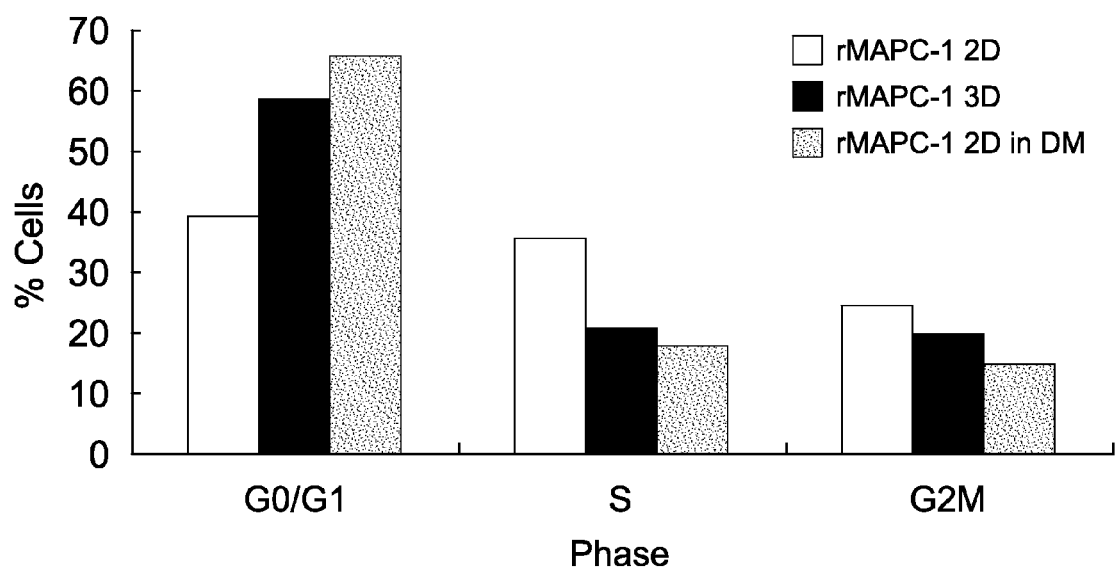

FIG. 20 shows cell cycle distribution in surface culture of MAPCs (☐) and MAPC aggregates (Day 4, ■) in maintenance medium, surface culture of MAPCs in differentiation medium (DM, ■).

Figure 21:
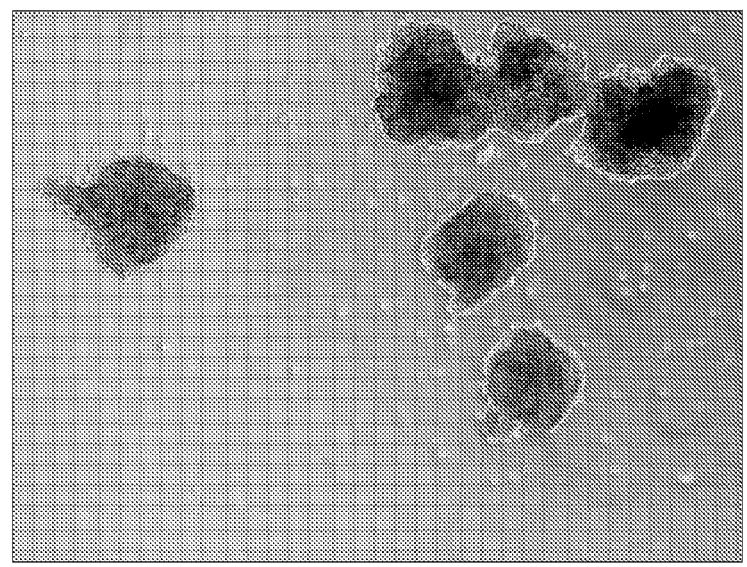

FIG. 21 shows morphology of MAPC aggregates on day 10 of static culture to demonstrate the beginning of budding of a small group of cells from each cell aggregate.

FIG. 22 shows expansion of MAPC aggregates in spinner flask for another rat MAPC line (a) cell proliferation profile for two expansion runs, (b) Transcript level of MAPC markers on MAPC aggregates (Day 0, ☐; Day 4 Run 1, ■; Day 4 Run 2, ■), and (c) flow cytometric measurement of Oct4 in MAPC aggregates on Day 4 (negative isotype control and Oct4 antibody treated samples are shown in red and blue respectively).

DETAILED DESCRIPTION OF THE INVENTION

It should be understood that this invention is not limited to the particular methodology, protocols, and reagents, etc., described herein and, as such, may vary. The terminology used herein is for the purpose of describing particular embodiments only, and is not intended to limit the scope of the disclosed invention, which is defined solely by the claims.

The section headings are used herein for organizational purposes only and are not to be construed as in any way limiting the subject matter described.

The methods and techniques of the present application are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 3rd ed., Cold Spring Harbor Laboratory Press, Cold Spring Harbor, N.Y. (2001) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990).

Definitions

As used herein, the terms below are defined by the following meanings.

"2D" refers to cell culture where cells grow by attaching (adhering) to a substrate. Such cells form monolayers or colonies where the cells are each attached to a substrate (where the substrate is other than the cells themselves).

"3D" refers to cell culture where cells grow as an aggregate through association of the cells with each other and not through association with a substrate other than the cells themselves. In the art, "3D" may refer to growth of cells that adhere to a scaffold or matrix. But, as used herein, 3D is used as above.

In one embodiment, cells can be initially grown on a substrate where some cells associate with (adhere to) the substrate but further growth forms cell-cell associations (aggregation) that do not depend on association (adherence) of the further-grown cells with the substrate. A cellular feeder layer is also considered a substrate. So attachment of cells to a feeder layer is also a form of adherent culture (not an aggregate) since attachment of the cells is not to each other but to the cells in the feeder layer.

"A" or "an" means herein one or more than one; at least one. Where the plural form is used herein, it generally includes the singular.

"Aggregate" refers to an association of cells in which the association is caused by cell-cell interaction rather than adherence to a substrate. In 2D monolayer culture, cells are "associated" with each other but by means of attachment to a substrate material, such as plastic or surface coating. In an aggregate, two or more cells associate with each other by biologic attachments to one another. This can be through surface proteins, such as extracellular matrix proteins.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may already be stored in a pharmaceutically-acceptable excipient so they may be directly administered or they may be mixed with an appropriate excipient when they are released from storage. Cells may be frozen or otherwise stored in a form to preserve viability. In one embodiment of the invention, cell banks are created in which the cells have been selected for a desired property. Following release from storage, and prior to administration to the subject, it may be preferable to again assay the cells for retention of the property. Then cells having the desired property can be administered to the subject for treatment. Banks can be made using cells derived from the individual to be treated (from their pre-natal tissues such as placenta, umbilical cord blood, or umbilical cord matrix or expanded from the individual at any time after birth) (autologous). Or banks can contain cells for allogeneic uses. A master cell bank is a reservoir of cells to provide an aliquot of cells that can be further expanded to provide doses for administration to a subject.

A "clinically-relevant" number of cells refers to a number of cells that is sufficient to effect a clinical response; that is, a prevention, reduction, amelioration, etc. of an undesirable pathological condition in a subject. A particular embodiment pertains to a number of cells that is sufficient to create a master cell bank.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" is a synonym of "comprising" (see above).

"Conditioned cell culture medium" is a term well-known in the art and refers to medium in which cells have been grown. Herein this means that the cells are grown for a sufficient time to secrete the factors that are effective to achieve a desired effect.

Conditioned cell culture medium refers to medium in which cells have been cultured so as to secrete factors into the medium. Cells can be grown through a sufficient number of cell divisions so as to produce effective amounts of such factors so that the medium has the effects. Cells are removed from the medium by any of the known methods in the art, including, but not limited to, centrifugation, filtration, immunodepletion (e.g., via tagged antibodies and magnetic columns), and FACS sorting.

"Dispersion" refers to cells derived from the aggregates and which retain the function of the cells in aggregate form in that they can still differentiate into cell types of more than one embryonic germ layer and/or express pluripotency markers as disclosed herein.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

An "effective dose" generally means an amount which provides the desired local or systemic effect, such as enhanced performance. For example, an effective dose is an amount sufficient to effect a beneficial or desired clinical result. The dose could be administered in one or more administrations and could include any preselected amount of cells. The precise determination of what would be considered an effective dose may be based on factors individual to each subject, including their size, age, injury and/or disease or injury being treated and amount of time since the injury occurred or the disease began. One skilled in the art, specifically a physician, would be able to determine the number of cells that would constitute an effective dose.

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

"Embryonic Stem Cells (ESC)" are well known in the art and have been prepared from many different mammalian species. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta. Some cells similar to ESCs may be produced by nuclear transfer of a somatic cell nucleus into an enucleated fertilized egg.

ES (and EG) cells can be identified by positive staining with antibodies to SSEA1 (mouse) and SSEA4 (human). At the molecular level, ES and EG cells express a number of transcription factors specific for these undifferentiated cells. These include oct3/4 and rex-1. Also found are the LIF-R (in mouse) and the transcription factors sox-2 and rox-1. Rox-1 and sox-2 are also expressed in non-ES cells. A hallmark of ES cells is telomerase enzyme activity, which provides these cells with an unlimited self-renewal potential in vitro. See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701; 6,500,668; 6,703,279; 6,875,607; 7,029,913; 7,112,437; 7,145,057; 7,153,684; and 7,294,508, each of which is incorporated by reference for teaching ES cells and methods of making them. ES cells have been grown in aggregate form. They are able to form embryoid bodies when grown without attachment to a substrate.

Oct3/4 (oct3 in humans) is a transcription factor expressed in the pre-gastrulation embryo, early cleavage stage embryo, cells of the inner cell mass of the blastocyst, and in embryonic carcinoma (EC) cells (Nichols et al., *Cell* 95:379-91 (1998)), and is down-regulated when cells are induced to differentiate. Expression of oct3/4 plays an important role in determining early steps in embryogenesis and differentiation. Oct3/4, in combination with rox-1, causes transcriptional activation of the Zn-finger protein rex-1, also required for maintaining undifferentiated ES cells (Rosfjord and Rizzino, *Biochem Biophys Res Commun* 203:1795-802 (1997); Ben-Shushan et al., *Mol Cell Biol* 18:1866-78 (1998)). In addition, sox-2, expressed in ESC/EC, but also in other more differentiated cells, is needed together with oct3/4 to retain the undifferentiated state (Uwanogho et al., *Mech Dev* 49:23-36 (1995)). Maintenance of murine ES cells and primordial germ cells requires the presence of LIF. The oct3/4 gene is transcribed into at least two splice variants in humans, oct3A and oct3B. The oct3B splice variant is found in many differentiated cells whereas the oct3A splice variant (also previously designated oct3/4) is reported to be specific for the undifferentiated ES cell. See Shimozaki et al. *Development* 130:2505-12 (2003).

"Expansion" refers to the proliferation of a cell without differentiation.

Use of the term "includes" is not intended to be limiting. For example, stating that stem cells "include" IPS cells does not mean that other stem cells are excluded.

"Increase" or "increasing" means to induce entirely where there was no pre-existing presence or to increase the degree of.

"Induced pluripotent stem cells (IPSC or IPS cells)" are somatic cells that have been reprogrammed, for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861 (2008); Jaenisch et al., *Cell*, 132:567-582 (2008); Hanna et al., *Cell*, 133:250-264 (2008); and Brambrink et al., *Cell Stem Cell*, 2:151-159 (2008). These references are incorporated by reference for teaching IPSCs and methods for producing them. It is also possible that such cells can be created by specific culture conditions (exposure to specific agents).

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only stem cells. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (e.g., bone marrow, peripheral blood, adipose tissue, etc.).

"MAPC" is an acronym for "multipotent adult progenitor cell." It refers to a cell that is not an embryonic stem cell or germ cell but has some characteristics of these. MAPC can be characterized in a number of alternative descriptions, each of which conferred novelty to the cells when they were discovered. They can, therefore, be characterized by one or more of those descriptions. First, they have extended replicative capacity in culture without being transformed (tumorigenic) and with a normal karyotype. Second, they may give rise to cell progeny of more than one germ layer, such as two or all three germ layers (i.e., endoderm, mesoderm and ectoderm) upon differentiation. Third, although they are not embryonic stem cells or germ cells, they may express markers of these primitive cell types so that MAPCs may express one or more of Oct 3/4 (i.e., Oct 3A), rex-1, and rox-1. They may also express one or more of sox-2 and SSEA-4. Fourth, like a stem cell, they may self-renew, that is, have an extended replication capacity without being transformed. This means that these cells express telomerase (i.e., have telomerase activity). Accordingly, the cell type that was designated "MAPC" may be characterized by alternative basic characteristics that describe the cell via some of its novel properties.

The term "adult" in MAPC is non-restrictive. It refers to a non-embryonic somatic cell. MAPCs are karyotypically normal and do not form teratomas in vivo. This acronym was first used in U.S. Pat. No. 7,015,037 to describe a pluripotent cell isolated from bone marrow. However, cells with expression of pluripotent markers and/or differentiation potential have been discovered subsequently and, for purposes of this invention, may be equivalent to those cells first designated "MAPC." Essential descriptions of the MAPC type of cell are provided in the Summary of the Invention above.

"Multipotent," with respect to the term in "MAPC," refers to the ability to give rise to cell lineages of more than one primitive germ layer (i.e., endoderm, mesoderm and ectoderm) upon differentiation, such as all three. This term is not used consistently in the literature.

MAPC represents a more primitive progenitor cell population than MSC (Verfullie, C. M., *Trends Cell Biol* 12:502-8 (2002), Jahagirdar, B. N., et al., *Exp Hematol*, 29:543-56 (2001); Reyes, M. and C. M. Verfullie, *Ann N Y Acad Sci*, 938:231-233 (2001); Jiang, Y. et al., *Exp Hematol*, 30896-904 (2002); and (Jiang, Y. et al., *Nature*, 418:41-9. (2002)).

The term "MultiStem®" is the trade name for a cell preparation based on the MAPCs of U.S. Pat. No. 7,015,037, i.e., a non-embryonic stem, non-germ cell as described above. MultiStem® is prepared according to cell culture methods disclosed in this patent application, particularly, lower oxygen and higher serum.

"Non-static culture conditions" include those in which the liquid cell culture is in motion. This can be done by any means that agitates the medium. Examples include Spinner flasks (stirred suspension), roller bottles, perfusion, aeration, stirred, or rotated, such as in a rotating wall vessel or rotary cell culture system.

"Pharmaceutically-acceptable carrier" is any pharmaceutically-acceptable medium for the cells used in the present invention. Such a medium may retain isotonicity, cell metabolism, pH, and the like. It is compatible with administration to a subject in vivo, and can be used, therefore, for cell delivery and treatment.

The term "potency" refers to the ability of the cells to achieve a desired effect.

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally-differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage. A progenitor cell can form a progeny cell that is more highly differentiated than the progenitor cell.

The term "reduce" as used herein means to prevent as well as decrease. In the context of treatment, to "reduce" is to either prevent or ameliorate one or more clinical symptoms. A clinical symptom is one (or more) that has or will have, if left untreated, a negative impact on the quality of life (health) of the subject. This also applies to the underlying biological effects as well.

"Selecting" a cell with a desired level of potency can mean identifying (as by assay), isolating, and expanding a cell. This could create a population that has a higher potency than the parent cell population from which the cell was isolated.

To select a cell that achieves the desired effect would include both an assay to determine if the cells achieve the desired effect and would also include obtaining those cells. The cell may naturally achieve the desired effects in that the cell was not incubated with or exposed to an agent that induces the effect. The cell may not be known to achieve the desired effect prior to conducting the assay. As an effect could depend on gene expression and/or secretion, one could also select on the basis of one or more of the genes that cause the effect.

Selection could be from cells in a tissue. For example, in this case, cells would be isolated from a desired tissue, expanded in culture, selected for achieving the desired effect, and the selected cells further expanded.

Selection could also be from cells ex vivo, such as cells in culture. In this case, one or more of the cells in culture would be assayed for achieving the desired effect and the cells obtained that achieve the desired effect could be further expanded.

Cells could also be selected for enhanced ability to achieve the desired effect. In this case, the cell population from which the enhanced cell is obtained already has the desired effect. Enhanced effect means a higher average amount per cell than in the parent population.

The parent population from which the enhanced cell is selected may be substantially homogeneous (the same cell type). One way to obtain such an enhanced cell from this population is to create single cells or cell pools and assay those cells or cell pools to obtain clones that naturally have the effect (as opposed to treating the cells with a modulator that induces or increases the effect) and then expanding those cells that are naturally enhanced.

However, cells may be treated with one or more agents with a modulator that induces or increases the effect. Thus, substantially homogeneous populations may be treated to enhance modulation.

If the population is not substantially homogeneous, then, it is preferable that the parental cell population to be treated contains at least 100 of the desired cell type in which enhanced effect is sought, more preferably at least 1,000 of the cells, and still more preferably, at least 10,000 of the cells. Following treatment, this sub-population can be recovered from the heterogeneous population by known cell selection techniques and further expanded if desired.

Thus, desired levels of effect may be those that are higher than the levels in a given preceding population. For example, cells that are put into primary culture from a tissue and expanded and isolated by culture conditions that are not specifically designed to produce the effect may provide a parent population. Such a parent population can be treated to enhance the effect per cell or screened for a cell or cells within the population that express greater degrees of effect without deliberate treatment. Such cells can be expanded then to provide a population with a higher (desired) expression.

"Self-renewal" refers to the ability to produce replicate daughter stem cells having differentiation potential that is identical to those from which they arose. A similar term used in this context is "proliferation."

"Serum-free medium" refers to medium in which serum is not present or, if present, is at levels at which the components of the serum have no effect on the growth or variability of the cells (i.e., are not actually necessary, such as residual or trace amounts).

"Static culture conditions" include those in which the liquid cell culture is not in motion. This means that there is no external force applied that agitates or mixes the medium.

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has de-differentiated, for example, by nuclear transfer, by fusion with a more primitive stem cell, by introduction of specific transcription factors, or by culture under specific conditions. See, for example, Wilmut et al., *Nature,* 385:810-813 (1997); Ying et al., *Nature,* 416:545-548 (2002); Gum et al., *Nature,* 440:1199-1203 (2006); Takahashi et al., *Cell,* 126:663-676 (2006); Okita et al., *Nature,* 448:313-317 (2007); and Takahashi et al., *Cell,* 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass). Stem cells may also be produced by introducing genes associated with stem cell function into a non-stem cell, such as an induced pluripotent stem cell.

A "subject" is a vertebrate, preferably a mammal, more preferably a human. Mammals include, but are not limited to, humans, farm animals, sport animals, and pets. Subjects in need of treatment by methods of the present invention include those suffering from a loss of function as a result of physical or disease-related damage.

The term "therapeutically effective amount" refers to the amount determined to produce any therapeutic response in a mammal. For example, effective amounts of the therapeutic cells or cell-associated agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Validate" means to confirm. One confirms that a cell is an expressor with a desired potency. This is so that one can then use that cell (in treatment, banking, drug screening, etc.) with a reasonable expectation of efficacy. Accordingly, to validate means to confirm that the cells, having been originally found to have/established as having the desired effects, in fact, retain that ability. Thus, validation is a verification event in a two-event process involving the original determination and the follow-up determination. The second event is referred to herein as "validation."

Forming the Initial Aggregate

WO 2009/092092, also from the inventors, disclosed that non-embryonic stem cells can successfully form aggregates in which the cells retain the undifferentiated phenotype of the single non-embryonic stem cells. Therefore, the aggregates are capable of producing progeny with a more differentiated phenotype. This application is incorporated herein by reference for teaching the formation of aggregates from single cells.

The cells that were useful included cells that are not transformed or tumorigenic and that may have a normal karyotype. For example, some, such as MAPC, are known not to form teratomas in vivo and to have a normal karyotype in culture.

The aggregate could be formed by using any method for non-adherent growth, such as, any of the known methods in the art. These included the hanging drop method (Kurosawa and Hopfl, cited below), the forced aggregation method (centrifugation) (Ng, cited below), methods wherein the cells are cultured on non-adherent plastic, suspension culture (static or stirred), bioreactor expansion platforms, and non-attachment or special coating e.g., temperature-sensitive polymer-based plates, microcontact printing of wells to control size of colonies, and microfluidic devices.

Many different basal media are known in the art. Such media may be used with or without serum (or at varying serum concentrations, e.g., 0.5%-20% or more). When serum is absent or reduced, the person of ordinary skill would know to use growth factors to complement the basal medium, including, but not limited to, EGF and/or PDGF. Oxygen concentrations may be reduced from atmospheric to ranges of 1-5, 5-10, 10-15, 15-20% and numbers between.

The stem cells can be derived from various tissues, such as bone marrow, placenta, peripheral blood, umbilical cord blood and tissue, skin, and fat. Cells designated "MAPC" in the literature are exemplified in this application. But the invention further contemplates any non-embryonic stem cell that forms cell types of more than one embryonic germ layer. See, for example, U.S. Pat. No. 7,311,905; 2003/0059414; 2002/0164794, all incorporated by reference for teaching these cells and methods for making them.

In addition, less differentiated stem cells may be derived by various manipulations, such as, by transfecting and expressing certain genes in differentiated cells to genetically reprogram the undifferentiated state, nuclear transfer of somatic cells into an environment that creates gene expression corresponding to a less differentiated phenotype than was present in the somatic cell, growth in media and culture conditions sufficient to maintain pluripotency (for example, "MAPC media" and expansion protocols), nuclear reprogramming by fusion of somatic cells with embryonic stem cells, culture-induced reprogramming-cell explantation, and treatment of somatic nuclei with cell extract from oocytes or pluripotent cells (Hochedlinger and Jaenisch, *Nature* 441: 1061-1067 (2006)).

The invention pertains to stem cells from any species and, particularly, mammalian species and, more particularly, to humans. Within a species, uses (e.g., administration of cells to a subject) can be of allogeneic cells. Across species, uses can be of xenogeneic cells. In a subject, cells can be autologous.

An aggregate, with respect to the invention, is defined as at least ten cells. But ranges include aggregates that are not so large that the inner cells become necrotic. This can include aggregates of 100-300µ and numbers in between, such as 150-250µ. The skilled person would recognize any useful number in that range. A useful number of aggregates would be greater than 50 for clinical applications. Cell numbers are variable and range from hundreds to tens of thousands or greater, e.g., 100-1000 (about 200, 300, 400, 500, 600, 700, 800, 900 cells), 1000-10,000, (about 2000, 3000, 4000, 5000, 6000, 7000, 8000, 9000 cells), 10,000-50,000 (about 20,000; 30,000; 40,000 cells) or more, etc.

The density of the aggregates in culture can range from about $10^4$-$10^8$ cells/ml. Accordingly, densities (per ml) of about $10^5$, $10^6$, and $10^7$ are also contemplated. Ranges in between are also contemplated, such as about $2\times10^4$, $3\times10^4$, $4\times10^4$, $5\times10^4$, $6\times10^4$, $7\times10^4$, $8\times10^4$, $9\times10^4$, $2\times10^5$, $3\times10^5$, $4\times10^5$, $5\times10^5$, $6\times10^5$, $7\times10^5$, $8\times10^5$, $9\times10^5$, $2\times10^6$, $3\times10^6$, $4\times10^6$, $5\times10^6$, $6\times10^6$, $7\times10^6$, $8\times10^6$, $9\times10^6$, $2\times10^7$, $3\times10^7$, $4\times10^7$, $5\times10^7$, $6\times10^7$, $7\times10^7$, $8\times10^7$, $9\times10^7$. Further sub-ranges within these densities are also contemplated.

The average number of cells in an aggregate that is formed under the non-static conditions can occur over a broad range, such as from about 1,000 to 50,000 or greater (per aggregate). Ranges in between are also contemplated, such as about 10,000, 20,000, 30,000, and 40,000. Sub-ranges within these ranges are also contemplated, such as 2,000, 3,000, 4,000, 5,000, 6,000, 7,000, 8,000, 9,000, 10,000-20,000, 20,000-30,000, 30,000-40,000, 40,000-50,000, and sub-ranges in between these.

The average number of cells in the starting aggregate (i.e., the aggregates that are used to inoculate the culture) may occur over a broad range, such as from about 10 cells to about 25,000 cells. Ranges in between are also contemplated, such as 10-100, 200, 300, 400, 500, 600, 700, 800, 900, and 1,000-10,000, 10,000-15,000, 15,000-20,000, 20,000-25,000, and also sub-ranges in between these numbers, such as 2,000, 3,000, 4,000, 5,000, 6,000, 7,000, 8,000, 9,000, 11,000, 12,000, 13,000, 14,000 (i.e., increments of 1000 up to 25,000) or even in between these ranges.

Thus, the average fold increase in the cell number per aggregate includes a range from 2× (25,000→50,000 cells per aggregate) to 5,000× (10→50,000). The fold increase depends on the number of cells in the initial and the expanded aggregate. The fold increase can be calculated from any of the numbers given above.

In specific embodiments, the starting aggregates contain, on the average, 1,000-5,000 cells.

The examples provided in this application utilize a cell that has been designated multipotent adult progenitor cell ("MAPC"). But the invention pertains to any and all stem cells that are not embryonic cells but can differentiate into all types of more than one germ layer (e.g., two or three) and/or express pluripotency markers.

Another parameter in forming aggregates is the purity of the isolated stem cell population used to form aggregates. Accordingly, in the present invention, aggregates may be formed of a desired stem cell that is present in a population containing other cells as well. Bone marrow cells, for example, comprise mixed populations of cells, which can be purified to a degree sufficient to produce a desired effect. Those skilled in the art can readily determine the percentage of a desired stem cell in a population using various well-known methods, such as fluorescence activated cell sorting (FACS). Purity of a given stem cell can also be determined according to the gene expression profile within a population.

Ranges of purity in populations comprising a given stem cell are about 50-55%, 55-60%, and 65-70%. Other ranges include purity of about 70-75%, 75-80%, 80-85%. Still other ranges include purity of about 85-90%, 90-95%, and 95-100%. However, populations with lower purity can also be useful, such as about 25-30%, 30-35%, 35-40%, 40-45% and 45-50%.

In the aggregates, the non-embryonic cells, such as MAPC, may be substantially homogeneous or be found in less than substantially homogeneous form. Purity, therefore, in the aggregate can vary as above. Furthermore, other cell types can be mixed in when forming the aggregates.

In methods in which the aggregate is subjected to differentiation conditions to produce some of the differentiated cell types discussed in this application, many, if not most of those conditions are available to those of ordinary skill in the art. See for example, Mays et al., *Expert Opinion Biol Ther* 2:173-184 (2007) and links therein to differentiation protocols; hepatocytes (*J Clin Invest* 109:1291-302; hematopoietic (*J Exp Med* 204:129-39), smooth muscle (*J Clin Invest* 116: 3139-3149 (2006)). These differentiation conditions are incorporated herein by reference. Many differentiation conditions are in U.S. Pat. No. 7,015,037 and Mays et al. (above), incorporated by reference for these protocols.

One protocol for forming the aggregates is using DMEM-low glucose, MCDB, 2% Fetal Calf Serum, PDGF-BB, EGF, LIF, BSA, insulin-selenium-transferrin (ITS), linoleic acid and lipid mixture and 5% Oxygen. It may be preferable to use conditions that enhance expression of oct3/4 transcription factor, for example, at the levels expressed in MAPCs in 2D (adherent) cultures.

Initial Aggregation Methods

There are at least two methods to form the aggregates: (a) hanging drop (surface tension based method); and (b) forced aggregation (physically centrifuging cells at 1500 rpm, 4 minutes onto the bottom of 96 well Ultra-low attachment U bottom plate (Corning). Although both methods are usable to form aggregates, the hanging drop method is more cost-effective to produce large number of aggregates. Other ways include stirred suspension or growth in a non-attachment plate/flask. Other potential methods of forming controlled-size aggregates would be methods such as microcontact printing.

These methods are illustrated below in the following citations, which are hereby incorporated by reference for teaching various non-adherent cell culture methods.

Dang et al., "Efficiency of embryoid body formation and hematopoietic development from embryonic stem cells in different culture systems" *Biotechnology and Bioengineering* 78: 442-453 (2002).

Konno et al., "Formation of embryoid bodies by mouse embryonic stem cells on plastic surfaces" *Journal of Bioscience and Bioengineering* 100:88-93 (2005).

Ng et al., "Forced aggregation of defined numbers of human embryonic stem cells into embryoid bodies fosters robust, reproducible hematopoietic differentiation. Commentary" *Blood* 106:1601-1603 (2005) [Forced aggregation method].

Kurosawa et al., "A simple method for forming embryoid body from mouse embryonic stem cells" *Journal of Bioscience and Bioengineering* 96: 409-411 (2003).

Magyar et al., "Mass production of embryoid bodies in microbeads" *Annals of the New York Academy of Sciences* 944: 135-143 (2001). [Scalable production of cell aggregates as microbeads].

Hopfl et al., "Differentiating embryonic stem cells into embryoid bodies" *Methods Mol Biol* 254:79-98 (2004) [Hanging drop method].

Cameron et al., "Improved development of human embryonic stem cell-derived embryoid bodies by stirred vessel cultivation" *Biotechnol Bioeng* 94:938-948 (2006) [Stirred-suspension culture system].

Wang et al., "Scalable producing embryoid bodies by rotary cell culture system and constructing engineered cardiac tissue with ES-derived cardiomyocytes in vitro" *Biotechnol Prog* 22:811-818 (2006) [Rotary suspension systems].

Yang et al., *Biomacromolecules* 8, 9, 2746-2752 (2007) [Use of temperature sensitive hydrogel].

Torisawa et al., "Lab on a Chip" 7:770-776 (2007) [Use of microfluidics for efficient EB size formation].

The aggregates can be formed with a starting (single) cell number greater than 100. A maximum of 4000 cells have been used to form a single aggregate over 4 days of Hanging drop/Forced aggregation method. Starting from 1000 cells, the aggregates had an approximate number of 6600 cells/aggregate (counted by trypan blue exclusion method) after 4 days of hanging drop culture. Therefore, a useful starting range could be 100-4000 for each aggregate with the most optimum being between 400-2000.

Stem Cells

The present invention can be practiced, preferably, using stem cells of vertebrate species, such as humans, non-human primates, domestic animals, livestock, and other non-human mammals.

Non-Embryonic

Non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269; umbilical cord matrix (Mitchell et al., *Stem Cells,* 21:50-60, 2003), small embryonic-like stem cells (Kucia et al., *J Physiol Pharmaco,* 57 Suppl 5:5-18, 2006), amniotic fluid stem cells (Atala, A., *J Tissue Regen Med* 1:83-96, 2007), skin-derived precursors (Toma et al., *Nat Cell Biol* 3:778-784, 2001), adipose tissue (U.S. 2005/0153442), gastrointestinal stem cells, epidermal stem cells, and hepatic stem cells, which also have been termed "oval cells" (Potten et al., *Trans R Soc Lund B Biol Sci* 353:821-830 (1998); Watt, F., *Trans R Soc Lond B Biol Sci* 353:831 (1997); Alison et al., *Hepatology* 29:678-683 (1998), and bone marrow (see U.S. Publication Nos. 2003/0059414 and 2006/0147246), each of which is incorporated by reference herein for teaching these cells.

Strategies of Reprogramming Somatic Cells

Several different strategies, such as nuclear transplantation, cellular fusion, and culture induced reprogramming, have been employed to induce the conversion of differentiated cells into an embryonic state. The references cited below are incorporated by reference for teaching how to make these cells and describing them.

Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature* 441:1061-1067 (2006) and Yamanaka, S., *Cell Stem Cell* 1:39-49 (2007)).

Nuclear Transfer

Nuclear transplantation (NT), also referred to as somatic cell nuclear transfer (SCNT), denotes the introduction of a nucleus from a donor somatic cell into an enucleated oocyte to generate a cloned animal (Wilmut et al., *Nature* 385:810-813 (1997). The generation of live animals by NT demonstrated that the epigenetic state of somatic cells, including that of terminally differentiated cells, can be reprogrammed to an embryonic state.

Fusion of Somatic Cells and Embryonic Stem Cells

Epigenetic reprogramming of somatic nuclei to an undifferentiated state has been demonstrated by fusion of embryonic cells with somatic cells. Hybrids between various somatic cells and embryonic carcinoma cells (Bolter, D., *Nat Rev Genet.* 7:319-327 (2006), embryonic germ (EG), or ES cells (Zwaka and Thomson, *Development* 132:227-233 (2005)) share many features with the parental embryonic cells, indicating that the pluripotent phenotype is dominant in such fusion products. As with mouse (Tada et al., *Curr Biol*

11:1553-1558 (2001)), human ES cells have the potential to reprogram somatic nuclei after fusion (Cowan et al., *Science* 309:1369-1373 (2005)); Yu et al., *Science* 318:1917-1920 (2006)). Activation of silent pluripotency markers, such as oct4, may occur (Do and Scholer, *Stem Cells* 22:941-949 (2004)). Forced overexpression of Nanog in ES cells promotes pluripotency when fused with neural stem cells (Silva et al., *Nature* 441:997-1001 (2006)).

Culture-Induced Reprogramming

Pluripotent cells have been derived from embryonic sources, such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol* 7:881-884 (1997)); embryonic stem cells have been derived from blastomeres (Wakayama et al., *Stem Cells* 25:986-993 (2007)); inner cell mass cells (source not applicable) (Eggan et al., *Nature* 428:44-49 (2004)); embryonic germ and embryonal carcinoma cells have been derived from primordial germ cells (Matsui et al., *Cell,* 70:841-847 (1992)); GMCS, maSSC, and MASC have been derived from spermatogonial stem cells (Guan et al., *Nature,* 440:1199-1203 (2006); Kanatsu-Shinohara et al., *Cell* 119:1001-1012 (2004); and Seandel et al., *Nature* 449: 346-350 (2007)); EpiSC cells are derived from epiblasts (Brons et al., *Nature* 448:191-195 (2007); Tesar et al., *Nature,* 448:196-199 (2007)); parthogenetic ES cells have been derived from human oocytes (Cibelli et al., *Science* 295L819 (2002); Revazova et al., *Cloning Stem Cells* 9:432-449 (2007)); human ES cells have been derived from human blastocysts (Thomson et al., *Science* 282:1145-1147 (1998)); MAPC have been derived from bone marrow (Jiang et al., *Nature,* 418:41-49 (2002); Phinney and Prockop, *Stem Cells* 25:2896-2902 (2007)); cord blood cells (derived from cord blood) (van de Ven et al., *Exp Hematol* 35:1753-1765 (2007)); neurosphere derived cells derived from neural cell (Clarke et al., *Science,* 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell,* 119: 1001-1012 (2004) or maGSCs (Guan et al., *Nature* 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline Recently, multipotent adult spermatogonial stem cells (MAPCs) were derived from testicular spermatogonial stem cells of adult mice, and these cells had an expression profile different from that of ES cells (Seandel et al., *Nature* 449:346-350 (2007)) but similar to EpiSC cells, which were derived from the epiblast of postimplantation mouse embryos (Brons et al., *Nature* 448:191-195 (2007); Tesar et al., *Nature* 448:196-199 (2007)).

Reprogramming by Defined Transcription Factors

Somatic cells can be reprogrammed to an ES-like state (Takahashi and Yamanaka, *Cell* 126:663-676 (2006)). Mouse embryonic fibroblasts (MEFs) and adult fibroblasts were programmed to pluripotent ES-like cells by transduction of oct4, sox2, c-myc, and Klf4. Cells were called iPS (induced pluripotent stem) cells. While genetic experiments had established that Oct4 and Sox2 are essential for pluripotency (Chambers and Smith, *Oncogene* 23:7150-7160 (2004); Ivanona et al., *Nature* 442:5330538 (2006); Masui et al., *Nat Cell Biol* 9:625-635 (2007)), c-myc and Klf4 may be dispensable (Nakagawa et al., *Nat Biotechnol* 26:191-106 (2008); Werning et al., *Nature* 448:318-324 (2008); Yu et al., *Science* 318: 1917-1920 (2007)).

MAPC

An exemplary cell of the present invention has been designated "MAPC." MAPC is an acronym for "multipotent adult progenitor cell" (non-ES, non-EG, non-germ) that has the capacity to differentiate into cell types of all three primitive germ layers (ectoderm, mesoderm, and endoderm). Genes found in ES cells also have been found in MAPCs (e.g., telomerase, Oct 3/4, rex-1, rox-1, sox-2). Oct 3/4 (Oct 3A in humans) appears to be specific for ES and germ cells. MAPC represents a more primitive progenitor cell population than MSC and demonstrates differentiation capability encompassing the epithelial, endothelial, neural, myogenic, hematopoietic, osteogenic, hepatogenic, chondrogenic and adipogenic lineages (Verfullie, C. M., *Trends Cell Biol* 12:502-8, 2002, Jahagirdar et al., *Exp Hematol* 29:543-56, 2001; Reyes and Verfullie, *Ann N Y Acad Sci* 938:231-233, 2001; Jiang et al., *Exp Hematol* 30896-904, 2002; and Jiang et al., *Nature* 418: 41-9, 2002). MAPCs thus emulate the broad biological plasticity characteristic of ES cells, while maintaining the other characteristics that make non-embryonic stem cells appealing (e.g., normal karyotype and does not form teratomas).

Human MAPCs are described in U.S. Pat. No. 7,015,037 and application Ser. No. 10/467,963, the contents of which are incorporated herein by reference for their description of MAPCs. MAPCs have been identified in other mammals. MAPCs can be isolated from multiple sources, including, but not limited to, bone marrow, placenta, umbilical cord and cord blood, muscle, brain, liver, spinal cord, blood and skin.

Isolation and Growth of MAPCs

Prior to forming aggregates, MAPCs can be isolated and cultured using methods disclosed herein and in U.S. Pat. No. 7,015,037, which is incorporated by reference herein for these methods.

Methods of MAPC isolation are known in the art. See, for example, U.S. Pat. No. 7,015,037, and these methods, along with the characterization (phenotype) of MAPCs, are incorporated herein by reference. MAPCs can be isolated from multiple sources, including, but not limited to, bone marrow, placenta, umbilical cord and cord blood, muscle, brain, liver, spinal cord, blood or skin. It is, therefore, possible to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

MAPCs have also been obtained by modified methods described in Breyer et al., *Experimental Hematology,* 34:1596-1601 (2006) and Subramanian et al., Cellular Programming and Reprogramming: Methods and Protocols; S. Ding (ed.), *Methods in Molecular Biology,* 636:55-78 (2010), incorporated by reference for these methods.

MAPCs from Human Bone Marrow as Described in U.S. Pat. No. 7,015,037

MAPCs do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of CD45$^+$ and Gly-A$^+$ cells, and the remaining approximately 0.1% of marrow mononuclear cells were then recovered. Cells could also be plated in fibronectin-coated wells and cultured as described below for 2-4 weeks to deplete the cells of $CD45^+$ and $Gly-A^+$ cells. In cultures of adherent bone marrow cells, many adherent stromal cells undergo replicative senescence around cell doubling 30 and a more homogeneous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Cells may be cultured in low-serum or serum-free culture medium. Serum-free medium used to culture MAPCs is described in U.S. Pat. No. 7,015,037. Commonly-used growth factors include but are not limited to platelet-derived growth factor and epidermal growth factor. See, for example, U.S. Pat. Nos. 7,169,610; 7,109,032; 7,037,721; 6,617,161; 6,617,159; 6,372,210;6,224,860; 6,037,174; 5,908,782; 5,766,951; 5,397,706; and 4,657,866; all incorporated by reference for teaching growing cells in serum-free medium.

Additional Culture Methods

In additional experiments the density at which MAPCs are cultured can vary from about 100 cells/$cm^2$ or about 150 cells/$cm^2$ to about 10,000 cells/$cm^2$, including about 200 cells/$cm^2$ to about 1500 cells/$cm^2$ to about 2000 cells/$cm^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 1-5% and, especially, 3-5%, can be used at any time during the isolation, growth and differentiation of MAPCs in culture.

Cells may be cultured under various serum concentrations, e.g., about 2-20%. Fetal bovine serum may be used. Higher serum may be used in combination with lower oxygen tensions, for example, about 15-20%. Cells need not be selected prior to adherence to culture dishes. For example, after a Ficoll gradient, cells can be directly plated, e.g., 250,000-500,000/$cm^2$. Adherent colonies can be picked, possibly pooled, and expanded.

In one embodiment, used in the experimental procedures in the Examples, high serum (around 15-20%) and low oxygen (around 3-5%) conditions were used for the cell culture. Specifically, adherent cells from colonies were plated and passaged at densities of about 1700-2300 cells/$cm^2$ in 18% serum and 3% oxygen (with PDGF and EGF).

In an embodiment specific for MAPCs, supplements are cellular factors or components that allow MAPCs to retain the ability to differentiate into cell types of more than one embryonic lineage, such as all three lineages. This may be indicated by the expression of specific markers of the undifferentiated state, such as Oct 3/4 (Oct 3A) and/or markers of high expansion capacity, such as telomerase.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional up-regulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads and combinations thereof. One embodiment of the present invention contemplates the use of FACS to identify and separate cells based on cell-surface antigen expression.

Pharmaceutical Formulations

U.S. Pat. No. 7,015,037 is incorporated by reference for teaching pharmaceutical formulations. In certain embodiments, the cell populations are present within a composition adapted for and suitable for delivery, i.e., physiologically compatible.

In some embodiments the purity of the cells (or conditioned medium) for administration to a subject is about 100% (substantially homogeneous). In other embodiments it is 95% to 100%. In some embodiments it is 85% to 95%. Particularly, in the case of admixtures with other cells, the percentage can be about 10%-45%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The choice of formulation for administering the cells for a given application will depend on a variety of factors. Prominent among these will be the species of subject, the nature of the condition being treated, its state and distribution in the subject, the nature of other therapies and agents that are being administered, the optimum route for administration, survivability via the route, the dosing regimen, and other factors that will be apparent to those skilled in the art. For instance, the choice of suitable carriers and other additives will depend on the exact route of administration and the nature of the particular dosage form.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

In some embodiments, cells/medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells appropriate to be used in accordance with various embodiments of the invention will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells to be effective; and such characteristics of the site such as accessibility to cells and/or engraftment of cells. Additional parameters include co-administration with other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

The optimal dose of cells for some embodiments will be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5\times10^5$ to $5\times10^6$ cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells may be administered in an initial dose, and thereafter maintained by further administration. Cells may be administered by one method initially, and thereafter administered by the same method or one or more different methods. The levels can be maintained by the ongoing administration of the cells. Various embodiments administer the cells either initially or to maintain their level in the subject or both by intravenous injection. In a variety of embodiments, other forms of administration are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments cells are administered to a subject in one dose. In others cells are administered to a subject in a series of two or more doses in succession. In some other embodiments wherein cells are administered in a single dose, in two doses, and/or more than two doses, the doses may be the same or different, and they are administered with equal or with unequal intervals between them.

Cells may be administered in many frequencies over a wide range of times. In some embodiments, they are administered over a period of less than one day. In other embodiment they are administered over two, three, four, five, or six days. In some embodiments they are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Uses

Useful cells are in aggregate form or in cells derived from the aggregate. Large numbers of cells can be produced by aggregation methods but the cells that are further used can be removed, e.g., dis-aggregated or dispersed from the aggregate. So, for example, pharmaceutical compositions can comprise the cells in aggregate form or derived from the aggregate (e.g., by dispersion). Likewise, differentiation factors can be applied to the cells in aggregate form or to cells derived from the aggregate. Pharmaceutical compositions can, therefore, be made with differentiated cells formed by applying differentiation conditions to the aggregate or to cells derived from the aggregate. Further, clinical uses described below pertain to the in vivo use of the undifferentiated aggregates and undifferentiated cells derived from the aggregates as well as differentiated progeny of the aggregates and differentiated progeny of cells derived from the aggregates. Undifferentiated cells are useful, like their differentiated progeny, because they may give rise to those progeny in vivo. (Undifferentiated cells may be useful even when they do not differentiate, for other beneficial purposes, such as angiogenic, immunomodulatory, cytogenic, trophic, etc.).

The aggregated cells or cells derived from the aggregates may have the capacity to be induced to differentiate to form at least one differentiated cell type of mesodermal, neurectodermal and endodermal origin. For example, the cells may have the capacity to be induced to differentiate to form cells of at least osteoblast, chondrocyte, adipocyte, fibroblast, marrow stroma, skeletal muscle, smooth muscle, cardiac muscle, endothelial, epithelial, hematopoietic, glial, neuronal or oligodendrocyte cell type.

The invention further provides differentiated cells obtained from the cells described above, wherein the progeny cell may be a bone, cartilage, adipocyte, fibroblast, marrow stroma, skeletal muscle, smooth muscle, cardiac muscle, endothelial, epithelial, endocrine, exocrine, hematopoietic, glial, neuronal or oligodendrocyte cell. The differentiated progeny cell may be a skin epithelial cell, liver epithelial cell, pancreas epithelial cell, pancreas endocrine cell or islet cell, pancreas exocrine cell, gut epithelium cell, kidney epithelium cell, or an epidermal associated structure.

The cells or their differentiated progeny can be used to correct a genetic disease, degenerative disease, cardiovascular disease, metabolic storage disease, neural, or cancer disease process. They can be used to produce gingiva-like material for treatment of periodontal disease. They can be used to develop skin epithelial tissue derived from the cells that can be utilized for skin grafting and plastic surgery. They can be used to enhance muscle, such as in the penis or heart. They can be used to produce blood ex vivo for therapeutic use, or to produce human hematopoietic cells and/or blood in prenatal or post natal animals for human use. They can be used as a therapeutic to aid for example in the recovery of a patient from chemotherapy or radiation therapy in treatment of cancer, in the treatment of autoimmune disease, to induce tolerance in the recipient. They can be used to treat AIDS or other infectious diseases.

Neuroretinal cells can be used to treat blindness caused by among other things but not limited to neuroretinal disease caused by among other things macular degeneration, diabetic retinopathy, glaucoma, retinitis pigmentosa.

The cells or cardiomyocytes derived from the cells can be used to treat cardiac diseases including, but not limited to, myocarditis, cardiomyopathy, heart failure, damage caused by heart attacks, hypertension, atherosclerosis, and heart valve dysfunction. They also can be used to treat a disease involving CNS deficits or damage. Further the stem cell, or its neuronally differentiated progeny cell, can be used to treat a disease involving neural deficits or degeneration including, but not limited to, stroke, Alzheimer's disease, Parkinson's disease, Huntington's disease, AIDS-associated dementia, spinal cord injury, and metabolic diseases affecting the brain or other nervous tissue.

Cells or their differentiated progeny, such as stromal cells, can be used to support the growth and differentiation of other cell types in vivo or in vitro, including, but not limited to, hematopoietic cells, pancreatic islet or beta cells, hepatocytes, and the like. The cells or differentiated cartilage progeny, can be used to treat a disease of the joints or cartilage, including, but not limited to, cartilage tears, cartilage thinning, and osteoarthritis. Moreover, the cells or their differentiated osteoblast progeny can be used to ameliorate a process having deleterious effects on bone including, but not limited to, bone fractures, non-healing fractures, osteoarthritis, "holes" in bones cause by tumors spreading to bone such as prostate, breast, multiple myeloma, and the like.

Using appropriate growth factors, chemokines, and cytokines, cells can be induced to differentiate to form a number of lineages, including, for example, a variety of cells of mesodermal phenotype, cells of neuroectodermal phenotype (glial cells, oligodendrocytes, and neurons), and cells of endodermal phenotype. These include osteoblasts, chondroblasts, adipocyte, cartilage and bone, skeletal muscle, smooth muscle, cardiac muscle, endothelial cells, hematopoietic cells, stromal cells, neuronal cells, and epithelial cells.

Osteoblasts: Cells that have been induced to differentiate to form bone cells can be used as cell therapy or for tissue regeneration in osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.

Chondrocytes: Cells that have been induced to differentiate to form cartilage cells can be used for cell therapy or tissue regeneration in age-related diseases or injuries, in sports-related injuries, or in specific diseases, such as rheumatoid arthritis, psoriasis arthritis, Reiter's arthritis, ulcerative colitis, Crohn's disease, ankylosing spondylitis, osteoarthritis, reconstructive surgery of the outer ear, reconstructive surgery of the nose, and reconstructive surgery of the cricoid cartilage.

Adipocytes: Cells that have been induced to differentiate to form adipocytes can be used in resculpting for reconstructive or cosmetic surgery, including but not limited to, breast reconstruction after mastectomy, reshaping tissue lost as a result of other surgery, such as tumor removal from the face or hand, breast augmentation, and reduction of wrinkles. Treatment of Type II diabetes is also applicable. Adipocytes thus derived can also provide an effective in vitro model system for the study of fat regulation.

Fibroblasts: Fibroblasts derived from the cells can be used for cell therapy or tissue repair to promote wound healing or to provide connective tissue support, such as scaffolding for cosmetic surgery.

Skeletal muscle: Cells that have been be induced to differentiate to form skeletal muscle cells can be used for cell therapy or tissue repair in the treatment of Duchenne muscular dystrophy, Becker muscular dystrophy, myotonic dystrophy, skeletal myopathy, and reconstructive surgery to repair skeletal muscle damage.

Smooth muscle: Cells that have been induced to differentiate to form smooth muscle cells can be used for cell therapy or tissue repair in the treatment of developmental abnormalities of the gastrointestinal system, such as oesophageal atresia, intestinal atresia, and intussusception, and replacement of tissues after surgery for bowel infarction or colostomy. Smooth muscle cells can also be used for bladder or uterine reconstruction, neovascularization, repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues.

Cardiomyocytes: Cardiomyocytes can be used for cell therapy or tissue repair for treating heart tissue damaged following myocardial infarction, in conjunction with congestive heart failure, during valve replacement, by congenital heart anomalies, or resulting from cardiomyopathies or endocarditis.

Microglial cells: Microglial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, and for regeneration after spinal cord injury.

Stromal cells: Stromal cells can be used as transplant cells for post-chemotherapy bone marrow replacement and bone marrow transplantation.

Endothelial cells: Endothelial cells can be used in the treatment of Factor VIII deficiency and to produce angiogenesis for neovascularization. Endothelial cells can also provide an in vitro model for tumor suppression using angiogenic inhibitors, as well as an in vitro model for vasculitis, hypersensitivity and coagulation disorders.

Hematopoietic cells: Hematopoietic cells can be used to repopulate the bone marrow after high-dose chemotherapy. Hematopoietic cells derived from the cells of the aggregate can be further differentiated to form blood cells to be stored in blood banks, alleviating the problem of a limited supply of blood for transfusions.

Neuroectodermal cells: Microglial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. Cells induced to form oligodendrocytes and astrocytes, for example, can be used for transplant into demyelinated tissues, especially spinal cord, where they function to myelinate the surrounding nervous tissues. The cells also can be used in cell replacement therapy and/or gene therapy to treat congenital neurodegenerative disorders or storage disorders such as, for instance, mucopolysaccharidosis, leukodystrophies (globoid-cell leukodystrophy, Canavan's disease), fucosidosis, GM2 gangliosidosis, Niemann-Pick, Sanfilippo syndrome, Wolman's disease, and Tay Sachs. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

Ectodermal epithelial cells: Cells can be used in cell replacement therapy and/or gene therapy to treat or alleviate symptoms of skin disorders such as alopecia, skin defects such as burn wounds, and albinism.

Endodermal epithelial cells: Epithelial cells can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders, such as inborn errors of the urea-cycle, for instance ornithine decarboxylase deficiency, citrullinemia, and arginosuccinic aciduria; inborn errors of amino acids and organic acids, such as phenylketonuria, hereditary tyrosinemia, and alpha1-antitrypsin deficiency; and coagulation disorders such as factor VIII and IX deficiency. The cells can also be used to treat acquired liver disorders that result from viral infections. The cells can also be used in ex vivo applications, such as to generate an artificial liver, to produce coagulation factors and to produce proteins or enzymes generated by liver epithelium. The epithelial cells can also be used in cell replacement therapy and/or gene therapy to treat or alleviate symptoms of biliary disorders, such as biliary cirrhosis and biliary atresia. The epithelial cells can also be used in cell replacement therapy and/or gene therapy to treat or alleviate symptoms of pancreatic disorders, such as pancreatic atresia, pancreas inflammation, and alpha1-antitrypsin deficiency. Further, as pancreatic epithelium, and as neural cells can be made, beta-cells can be generated. These cells can be used for the therapy of diabetes (subcutaneous implantation or intra-pancreas or intra-liver implantation. Further, the epithelial cells can also be used in cell replacement therapy and/or gene therapy to treat or alleviate symptoms of gut epithelium disorders such as gut atresia, inflammatory bowel disorders, bowel infarcts, and bowel resection.

Cells Are Useful For Tissue Repair: Cells can also be used for tissue repair. Cells can be implanted into bone to enhance the repair process, to reinforce weakened bone, or to resurface joints. Chondrocytes can be injected into joints to resurface joint cartilage. Caplan et al. (U.S. Pat. No. 5,855,619) describe a biomatrix implant including a contracted gel matrix into which mesenchymal stem cells have been incorporated. The implant is designed for repair of a tissue defect, especially for injury to tendon, ligament, meniscus, or muscle. Cartilage, for example, can be formed by the addition of chondrocytes in the immediate area around a porous, 3-dimensional scaffold made, for example, of collagen, synthetic polyglycolic acid fibers, or synthetic polylactic fibers. The inventors have shown that cells of the present invention differentiate to form chondrocytes, for example, which can be deposited in and around a collagen, synthetic polyglycolic, or synthetic polylactic or other scaffold material to provide an implant to facilitate tissue repair.

Cells can be used to produce tissues or organs for transplantation. Oberpenning et al. (*Nature Biotechnology* 17:149-155 (1999)) reported the formation of a working bladder by culturing muscle cells from the exterior canine bladder and lining cells from the interior of the canine bladder, preparing sheets of tissue from these cultures, and coating a small polymer sphere with muscle cells on the outside and lining cells on the inside. The sphere was then inserted into a dog's urinary system, where it began to function as a bladder. Nicklason et al. (*Science* 284: 489-493 (1999)), reported the production of lengths of vascular graft material from cultured smooth muscle and endothelial cells. Other methods for forming tissue layers from cultured cells are known to those of skill in the art (see, for example, Vacanti et al., U.S. Pat. No. 5,855,610).

For the purposes described herein, autologous, allogeneic, or xenogeneic cells can be administered to a patient, either in differentiated or undifferentiated form, genetically altered or unaltered, by direct injection to a tissue site, systemically, on or around the surface of an acceptable matrix, or in combination with a pharmaceutically-acceptable carrier.

Model System for Studying Differentiation Pathways

The invention provides a method of using the aggregates or cells derived from the aggregates to characterize cellular responses to biologic or pharmacologic agents involving contacting the cells with one or more biologic or pharmacologic agents and identifying one or more cellular responses to the one or more biologic or pharmacologic agents. Such agents may have various activities. They could affect differentiation, metabolism, gene expression, viability, and the like. The cells are useful, therefore, for e.g., toxicity testing and identifying differentiation factors.

Cells of the present invention are useful for further research into developmental processes, as well. Ruley et al. (WO 98/40468), for example, have described vectors and methods for inhibiting expression of specific genes, as well as obtaining the DNA sequences of those inhibited genes. Cells of the present invention can be treated with the vectors such as those described by Ruley, which inhibit the expression of genes that can be identified by DNA sequence analysis. The cells can then be induced to differentiate and the effects of the altered genotype/phenotype can be characterized.

Hahn et al. (*Nature* 400: 464-468 (1999)) demonstrated, for example, that normal human epithelial fibroblast cells can be induced to undergo tumorigenic conversion when a combination of genes, previously correlated with cancer, were introduced into the cells.

Control of gene expression using vectors containing inducible expression elements provides a method for studying the effects of certain gene products upon cell differentiation. Inducible expression systems are known to those of skill in the art. One such system is the ecdysone-inducible system described by No et al. (*Proc. Natl. Acad. Sci. USA* 93:3346-3351 (1996).

Cells can be used to study the effects of specific genetic alterations, toxic substances, chemotherapeutic agents, or other agents on the developmental pathways. Tissue culture techniques known to those of skill in the art allow mass culture of hundreds of thousands of cell samples from different individuals, providing an opportunity to perform rapid screening of compounds suspected to be, for example, teratogenic or mutagenic.

For studying developmental pathways, cells can be treated with specific growth factors, cytokines, or other agents, including suspected teratogenic chemicals. Cells can also be genetically modified using methods and vectors known in the art. Furthermore, cells can be altered using antisense technology or treatment with proteins introduced into the cell to alter expression of native gene sequences. Signal peptide sequences, for example, can be used to introduce desired peptides or polypeptides into the cells. A particularly effective technique for introducing polypeptides and proteins into the cell has been described by Rojas, et al., in *Nature Biotechnology* 16:370-375 (1998). This method produces a polypeptide or protein product that can be introduced into the culture media and translocated across the cell membrane to the interior of the cell. Any number of proteins can be used in this manner to determine the effect of the target protein upon the differentiation of the cell. Alternately, the technique described by Phelan et al. (*Nature Biotech.* 16:440-443 (1998)) can be used to link the herpes virus protein VP22 to a functional protein for import into the cell.

Cells can also be genetically engineered, by the introduction of foreign DNA or by silencing or excising genomic DNA, to produce differentiated cells with a defective phenotype in order to test the effectiveness of potential chemotherapeutic agents or gene therapy vectors.

Kits

Cells can be provided in kits, with appropriate packaging material. For example, cells can be provided as frozen stocks, accompanied by separately packaged appropriate factors and media, as previously described herein, for culture in normal monolayer and/or as aggregates in the undifferentiated state. Additionally, separately packaged factors for induction of differentiation can also be provided.

The invention will be further described by reference to the following detailed examples.

EXAMPLES

Example 1

Self-Assembly of Multipotent Adult Progenitor Cells (MAPCs)

Several stem or progenitor cells have been identified from bone marrow, peripheral blood, cord blood, fetal and adult liver, and embryonic stem cells with the potential to proliferate and differentiate into 'hepatocyte-like' cells in vitro or in vivo. Multipotent Adult Progenitor Cells (MAPCs) isolated from postnatal rat, mouse and human bone marrow can be expanded in vitro without senescence, differentiate in vitro and in vivo, at the single cell level, into different cell types of the three germ layer lineages. MAPCs have the advantage of not forming teratomas when transplanted and can be selected from autologous bone marrow without the need for immunosuppression.

The inventors investigated the ability of MAPCs to self-assemble into 3D aggregates. MAPCs were successfully induced into 3D aggregates that exhibited good viability, morphology, and undifferentiated phenotype in terms of expression of high levels of oct3/4 and lack of expression of differentiated markers when formed under "MAPC media" and 5% oxygen. The aggregates retained the ability to undergo spontaneous multi-lineage differentiation. Other than the advantage of obtaining more functionally mature differentiated cells, 3D culture provides a unique model system for studying nascent 3D development and can potentially help in the design of scalable culture systems that can be monitored and controlled to enhance differentiation.

Accordingly, the inventors identified conditions for optimal growth of undifferentiated MAPCs in 3D spherical clusters and assessed their differentiation potential to several cell types, specifically of the endodermal lineage. They found that undifferentiated MAPCs form 3D aggregates in culture and that the 3D aggregates retain the capacity to differentiate.

Experiment

Rat MAPC clones expressing high levels of oct3/4 were used for formation of MAPC aggregates using either the hanging drop method (surface tension driven) or the forced aggregation method (centrifugation) over a period of 4 days using MAPC media, MAPC media without LIF (leukemia inhibitory factor), or differentiation basal media in both low and high oxygen conditions. The starting cell number between 400-4000 cells/well was used in both the methods.

Upon characterization of the MAPC aggregates formed using flow cytometry and quantitative real time polymerase chain reaction (QRT-PCR), MAPC media with LIF and low oxygen condition was optimum as oct3/4 mRNA expression levels was equivalent between MAPCs before and after aggregate formation and almost 90% of the number of cells expressing in MAPCs (~79%) before aggregate formation expressed oct3/4 at the protein level after formation of aggregates (~69%). Further, the oct3/4 mRNA levels were comparable between aggregates formed using the hanging drop method or the forced aggregation method. The aggregates also expressed GATA6, HNF3b and Goosecoid at levels that are comparable to expression levels in MAPCs and did not show any expression of differentiation markers like AFP, albumin, AAT and TAT. Upon spontaneous differentiation in differentiation basal media (upon removal of LIF, PDGF and EGF), the cell aggregates underwent spontaneous differentiation to express Nestin and Pax6 corresponding to neuroectoderm, Flk-1 and SM22 corresponding to mesoderm and AFP and Albumin corresponding to the endoderm germ layer. Although all of the above work was using rat high-oct3/4 expressing MAPCs, low-oct3/4 rat MAPCs also formed aggregates with the ability to undergo differentiation to several cell types. There is also evidence of 3D aggregates from mouse MAPC clones that also retained the expression of oct3/4 in the aggregates and subsequently underwent spontaneous differentiation upon transfer to differentiation basal media.

Upon differentiation of rat high oct3/4 MAPC aggregates using the protocol optimized earlier for hepatocyte differentiation, the outcome of differentiation was comparable to high density 2D differentiation that was performed at the same time based on expression of hepatic markers like albumin, AFP, TTR, AAT and TAT. Therefore, it is apparent that the 3D aggregates are capable of undergoing significant levels of differentiation to the hepatic lineage starting from a 'MAPC-like' phenotype.

Functional and structural properties of the differentiated aggregates: albumin ELISA for estimating albumin secretion rates, PAS staining for glycogen storage, immunostaining investigating the polarization into basal, apical and lateral domains and elucidating the ultra-structural characteristics using transmission electron microscopy (TEM). In addition, the use of these oct3/4 expressing MAPC aggregates as a potential method for scalable expansion of MAPCs also was explored.

Materials and Methods
"MAPC Media"

MAPC media contained 60% (v/v) low glucose Dulbecco's Modified Eagle Media (DMEM) (11885, Gibco BRL, Carlsbad, Calif., USA), 40% (v/v) MCDB-201 (M6770, Sigma), 1% (v/v) 1× insulin-transferrin-selenium (ITS; Sigma), 1% (v/v) 1× linoleic acid bovine serum albumin (LA-BSA; Sigma), $5 \times 10^{-8}$ M dexamethasone (Sigma), $10^{-4}$ M ascorbic acid 3-phosphate (Sigma), 100 units of penicillin, 1000 units of streptomycin, 2% (v/v) fetal bovine serum (FBS; Hyclone, Logan, Utah, USA), 10 ng/ml mouse epidermal growth factor (Sigma), 10 ng/ml human platelet derived growth factor (R&D systems, Minneapolis, Minn., USA), 0.54% 1×β-mercaptoethanol and 1000 units/ml mouse leukemia inhibitory factor. Media was sterilized using a 22-1 μm filter (Millipore, Billerica, Mass., USA) and was kept at 4° C. for a maximum of 3-4 weeks.

Formation of MAPC Aggregates

MAPC aggregates were formed by using either the Hanging drop method or the forced aggregation method. In the Hanging drop method; MAPCs were seeded at 100-4000 cells/well of a 60-well microtitre plate (Nunc) in 20 μl of MAPC medium/well. The plates were then inverted and placed in 5% oxygen 37 C incubator for 4-5 days for the aggregates to form. In the forced aggregation method, 100-4000 MAPCs/well of a 96 well U bottom Ultra-low attachment plate (Corning) were centrifuged at 1500 rpm, 4 minutes and the cells were allowed to aggregate in a 5% oxygen 37 C incubator over the next 4-5 days.

Differentiation of MAPC Aggregates

There recently was developed a four-step, 21-day differentiation protocol optimized for medium components, oxygen levels and extra-cellular matrix for efficient differentiation to cells with morphological, phenotypic and functional characteristics of hepatocytes from MAPCs. The four-step protocol consisted of the following: (1) culturing MAPCs with 50 ng/ml Wnt3a and 100 ng/ml Activin A for six days; (2) then culturing the cells from step (1) with 10 ng/ml bFGF and 50 ng/ml BMP4 for four days; (3) then culturing the cells from step (2) with 50 ng/ml aFGF, 10 ng/ml FGF4 and 25 ng/ml FGF8b for four days; and (4) then culturing the cells from step (3) with 20 ng/ml HGF and 100 ng/ml Follistatin for seven days. In order to discriminate between hepatocyte- or biliary-like cells, Activin was inhibited by Follistatin. Prior to differentiation of the cells, undifferentiated MAPCs were expanded at large scale until several million cells were obtained. Cells then were plated at 50,000-60,000 cells/cm$^2$ in Matrigel (2%) coated wells. Initially, cells were cultured in expansion medium until they reached 80-90% confluency 16 hours later. Then, cells were washed twice with PBS and the medium was switched to differentiation medium. To verify whether the addition of the cytokines had a real hepatocyte inducing effect, differentiation was performed using basal differentiation medium only. All cells were cultured in low oxygen (5%) conditions in the basal differentiation medium, which consisted of DMEM (60%), MCDB (40%), ascorbic acid (1×), penicillin/streptomycin (1×), beta-mercaptoethanol, insulin-transferrin-selenium (ITS) (0.25×), LA-BSA (0.25×) and dexamethasone ($10^{-6}$M). A high concentration of dexamethasone was used because some hepatocyte specific genes (i.e., tyrosine aminotransferase, MRP2 and tryptophan 2,3 dioxygenase) are upregulated by glucocorticoids, as they contain a glucocorticoid response element. In the complete absence of serum, cell death occurred. However, using Wnt3a, differentiation was induced in serum-free conditions. If no cytokines were added to the basal differentiating medium, 2% serum was added until day 12 and then stopped. Because high concentrations of dexamethasone, together with insulin, can induce adipogenesis, a lower amount of insulin was used.

Example 2

Comparison of Differentiation of Rat MAPC Lines R2old and 19 Under 2D and 3D Conditions The goal of this study was to demonstrate the multi-lineage differentiation capability of MAPCs when grown and cultured as 3D aggregates. Two lines of rat MAPCs: R2old and 19, were used and were maintained for a period of 16 days as 3D aggregates in MAPC maintenance conditions: MAPC media with 5% oxygen. At the end of the 16 day period, 3D aggregates were dissociated and replated onto fibronectin-coated dishes, similar to standard 2D monolayer maintenance of rat MAPCs. Subsequently, growth factor mediated differentiation to hepatocytes, endothelial cells and neural precursor cells were performed and the differentiations were compared to differentiations of rat MAPCs that were maintained in 2D monolayer culture during the same time period. The data in FIGS. 11 (A), (B) and (C) indicate the expression of markers corresponding to the different cell types, by Quantitative-real time (QRT)-PCR. From the data, it appeared that the cells maintained as 3D aggregates retained the potential to undergo multi-lineage differentiation at levels comparable to cells maintained in 2D culture. Thus, MAPCs could be maintained in 3D culture without loss of quality, thus making it amenable to scale-up in bioreactors.

Example 3

Materials and Methods

Establishment and Maintenance of Rat MAPC Lines

Two rat MAPC lines were used in this study. The isolation of rat MAPC lines has been previously described (Breyer et al. 2006; Ulloa-Montoya et al. 2007). Briefly, rat MAPC lines were isolated from the tibia and femur of 4 week old female rat (Fischer). Cells were plated on 6 well tissue culture plates in MAPC medium at $6 \times 10^6$/well and cultured in a humidified incubator at 37° C. with 5% oxygen and 5.5% $CO_2$. After 4 weeks of culture, hematopoeitic cells were removed using magnetic microbeads against CD 45 and Ter 119 (Miltenyi Biotec) and the remaining cells were seeded into 96 well plates at 5 cells/well. Cells with small size and spindle shaped morphology that appear in the wells were subsequently picked and screened for MAPC phenotype (expression of Oct4, Rex1 and CD31) and tri-lineage differentiation potential (Breyer et al. 2006). The established MAPC cell lines were maintained in MAPC medium at 37° C. in a 5% oxygen and 5-6% $CO_2$ incubator at a starting cell density of 300 cells/cm$^2$ and passaged using 0.05% (w/v) Trypsin-EDTA (5 mg/l Cellgro) every two days (Breyer et al. 2006).

MAPC Media

MAPC medium consisted of a basal medium that was a 60/40 (v/v) mixture of low glucose Dulbecco's Modified Eagle media (DMEM) (Gibco, USA) and MCDB-201 (Sigma) supplemented with 0.026 µg/ml ascorbic acid 3-phosphate (Sigma), linoleic acid bovine serum albumin (LA-BSA, Sigma)) (final concentrations of $10^3$ µg/ml BSA and 8.13 µg/ml linoleic acid), insulin-transferrin-selenium (ITS, Sigma) (final concentration 10 µg/ml insulin, 5.5 µg/ml transferrin, 0.005 µg/ml sodium selenite), 0.02 µg/ml dexamethasone (Sigma), 4.3 µg/ml (3-mercaptoethanol and 2% (v/v) qualified fetal bovine serum (Hyclone). Complete MAPC medium also contained three growth factors: human platelet derived growth factor (PDGF-BB, R&D) (10 ng/ml), mouse epidermal growth factor (EGF, Sigma) (10 ng/ml) and mouse leukemia inhibitory factor (LIF) ($10^3$ Units/ml) (Chemicon, ESGRO). All media used were also supplemented with 100 IU/ml penicillin and 100 µg/ml streptomycin (Gibco).

Static Plate Culture of MAPC Aggregates

MAPC aggregates were formed from single cells of MAPCs using the hanging drop method (Kurosawa et al. 2003) or the forced aggregation method (Ng et al. 2005). Briefly, in the hanging drop method 300-3000 single cells were suspended in a single drop of medium hanging on an inverted plastic surface (Nunc) containing 60 small drops of cells and medium and each were allowed to agglomerate into individual aggregates. In the forced aggregation method, cells in suspension were placed in a well of an ultra-low attachment round bottomed 96 well plate (Corning) and centrifuged for 4 min at 1500 rpm, to allow cells to settle to the bottom of the well. Unless otherwise specified the settled cells were grown in a 37° C. incubator at 5% oxygen to allow for aggregates to form over time.

For static plate culture, MAPC aggregates were formed using either of the two methods. When formed by the hanging drop method, the MAPC aggregates from day 4 were cultured in ultra-low attachment 24 well plates (Corning) with 10 aggregates/wells. Forced aggregation method aggregates were formed and cultured for the entire culture period in 96 well plates. In both cases, MAPC medium and 5% oxygen conditions were used with 50% medium changes every two days. MAPC aggregates were also plated in differentiation conditions (MAPC medium without LIF, PDGF and EGF and 21% oxygen) for the same time period as maintenance cultures.

Suspension Flask Culture of MAPC Aggregates

Prior to suspension culture, MAPC aggregates were formed using the forced aggregation method in static culture for two days. Aggregates were then transferred to a 250 ml spinner flask at an initial cell concentration of 50,000 cells/ml and the culture was stirred at 70 rpm and kept inside a 37° C. incubator with 5% oxygen control.

Dissociation of MAPC Aggregates

To dissociate the MAPC aggregates into single cells, the aggregates were washed once with PBS and suspended in pre-warmed 0.05% (w/v) Trypsin-EDTA for 15-20 min in a 37° C. water bath. The aggregates-cell suspension was pipetted a few times and subsequently incubated for an additional 5 min in the water bath until the aggregates were dissociated into single cells, as observed under the microscope.

RNA Isolation and Quantitative Real Time Polymerase Chain Reaction (RT-qPCR)

Total RNA was isolated from rMAPC cell lysates using RNAeasy microkit (Qiagen) according to instructions provided in the kit. cDNA was synthesized from the extracted RNA using the Superscript III reverse transcriptase (Invitrogen) method. The PCR reaction mix consisted of cDNA samples, SYBR Green Mix PCR reaction buffer (Applied Biosystems) and primers (5 µM stocks, sequences listed in table 1). The RT-qPCR reaction was run on a Realplex mastercycler (Eppendorf) using the following program: 50° C. for 2 min, 95° C. for 10 min, and 40 cycles at 95° C. for 15 sec and 60° C. for 1 min followed by a dissociation protocol to obtain a melting curve. Transcript abundance relative to GAPDH was expressed as $\log_2$(Transcript expression relative to GAPDH) and calculated as $\Delta$Ct which is Ct(gene of interest)-Ct(GAPDH) and Transcript abundance in sample relative to day 0 was expressed as the $\log_2$(Transcript expression level relative to day 0) and calculated as $\Delta$Ct (day 0)-$\Delta$Ct(day of sample). Student's t-test with a p-value cut off of 0.05 was used to call for any significant difference in expression between the different samples.

Intracellular Staining for Oct4 by Flow Cytometry

Cells harvested by trypsinization were washed with and suspended in PBS with 3% (v/v) serum at 100,000 cells per FACS tube. After fixing with 4% paraformaldehyde for 15-20 min, and blocking for 1 hr in SAP buffer (PBS with 0.1% (w/v) saponin and 0.05% (w/v) sodium azide) supplemented with 10% donkey serum, cells were incubated for 1 hr with 1 µg/ml Oct3/4 antibody (Santa-Cruz, N19) or Goat IgG isotype control (Jackson Immunoresearch) diluted in SAP buffer before incubating with Cy5 labeled anti-goat IgG (Jackson Immunoresearch, 1:500 in SAP buffer) for 30 min Finally, cells were washed, filtered and re-suspended in 500 µl PBS for flow cytometry analysis using FACS Calibur (Becton Dickinson).

In-Vitro Directed Differentiation for Evaluating Maintenance of Differentiation Potency of MAPC Neuroectodermal Differentiation rMAPC were cultured at 1500 cells/cm2 on 0.1% gelatin coated T75 flasks in neural differentiation medium that consisted of 50% (v/v) DMEM/F12 (Invitrogen) and 50% (v/v) neurobasal A medium (Invitrogen) supplemented with N2 plus supplement (R&D systems), B27 (Invitrogen), 4.3 µg/ml β-mercaptoethanol, 0.3 mg/ml glutamine (Invitrogen) for 2 days. On Day 2, the medium was completely replaced with Euromed-N medium (Annovum/Euroclone) supplemented with 0.3 mg/ml glutamine, N2 plus supplement, 4.3 µg/ml β-mercaptoethanol and growth factors: basic fibroblast growth factor (R&D, bFGF) (10 ng/ml) and EGF (Sigma) (10 ng/ml). On Day 6, cells were trypsinized and re-plated in 0.1% gelatin coated T25 flasks in neural differentiation medium supplemented with bFGF (10 ng/ml) and EGF (10 ng/ml). Differentiations were continued for fourteen days in 5% oxygen conditions with media change every two days.

Endothelial Differentiation rMAPC were cultured on fibronectin (100 ng/ml) coated 24 well plates at a cell density of 45,000 cells/cm$^2$ in MAPC media. After about 16 hr, the medium was completely replaced with endothelial differentiation medium whose composition was the same as MAPC medium except that the three growth factors were absent, dexamethasone was at 0.4 µg/ml, and that 10 ng/ml recombinant human VEGF (R&D) was added. Differentiations were continued for twenty days in 21% oxygen conditions with 50% media change every two days.

Hepatocyte Differentiation rMAPC were cultured on matrigel (2%, BD) coated wells of a 24 well plate at a starting cell density of 50,000 cells/cm$^2$ in MAPC medium until a confluence of 80-90% is reached. Subsequently, the expansion medium was completely replaced with differentiation basal medium whose composition was the same as MAPC medium except that ITS and LA-BSA were at 25% of the amount in MAPC medium, dexamethasone was at 0.4 µg/ml and the three protein factors and serum were absent. Furthermore, additional protein factors were added as described below. The cytokines and growth factor supplements were added as follows: (i) Day 0: Activin A at 100 ng/ml and Wnt3a at 50 ng/ml (ii) Day 6: bFGF at 10 ng/ml and BMP4 at 50 ng/ml (iii) Day 10: FGF8b at 25 ng/ml, aFGF at 50 ng/ml and FGF4 at 10 ng/ml (iv) Day 14: HGF at 20 ng/ml and Follistatin at 100 ng/ml. Differentiations were carried out for twenty days in 21% oxygen conditions with 50% media change, corresponding to the differentiation stage, every two days. On days 0, 6, 10, and 14, complete medium was replaced with fresh medium with supplements for the ensuing differentiation stage.

Time Lapse Microscopy

MAPCs were seeded at 1000 cells/well in ultra-low attachment round bottom 96 well plates (Corning). The initial aggregation of the cells was observed by microscope (Leica) located in an incubation system of 37° C., 5% CO2, and 5% or 21% O2 for 48 hours. Images of cells undergoing aggregation were taken every 4 min over 48 hr. The size of aggregates was determined from an average of three or more wells each containing a single aggregate.

Transmission Electron Microscopy

Cells aggregates were washed thrice with 0.1 M cacodylate buffer and fixed in 2.5% glutaraldehyde and 0.1 M sodium cacodylate buffer (pH 7.2) for 40 min After post-fixation in 1% osmium tetroxide and 0.1 M of cacodylate buffer, the samples were dehydrated in graded series of ethanol followed by propylene oxide treatment, and embedded in epoxy resin. Ultrathin sections were cut, stained with uranyl acetate and lead citrate, and examined using a JEOL 1200 EXII electron microscope at the Characterization facility at University of Minnesota.

E-Cadherin Staining

Cells aggregates were fixed in 4% paraformaldehyde for 30 min and washed with PBS. The samples were incubated in 5% sucrose in PBS overnight and supercooled with isopentane before freezing in OCT and obtaining sections. $H_2O_2$ was used to inhibit endogenous peroxidase and incubated with fetal bovine serum (FBS) to reduce non-specific binding. Cells were then incubated with anti-E-cadherin (BD) antibody or with isotype-matched negative control antibodies (mouse IgG2a) and then subsequently visualized using EnVision-Peroxidase with DAB substrate (Dako).

Cell Viability Staining

The "live/dead viability/cytotoxicity kit" (Invitrogen) was used to stain cells in the aggregates with calcein and ethidium. Component B was added first to DPBS (1:1000) and then component A was added to DPBS with component B (1:2000). Cells were incubated with the staining solution for 15-30 min at 37° C. Cells were washed once with PBS and observed under inverted fluorescent microscope (Axiovert 200, Zeiss). Live and dead cells appear as green and red respectively. Validation of the protocol to detect dead cells was confirmed with the red stain observed in cells in aggregates that were treated with 0.1% (w/v) saponin (to induce permeabilization based cell death) for 30 min prior to the staining protocol.

Cell Cycle Analysis

Figure 12A:
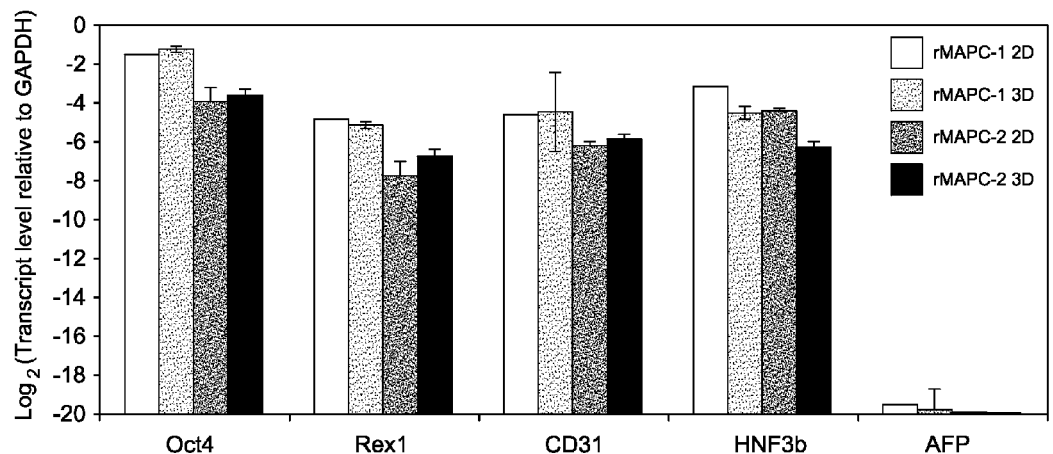
Figure 12B:
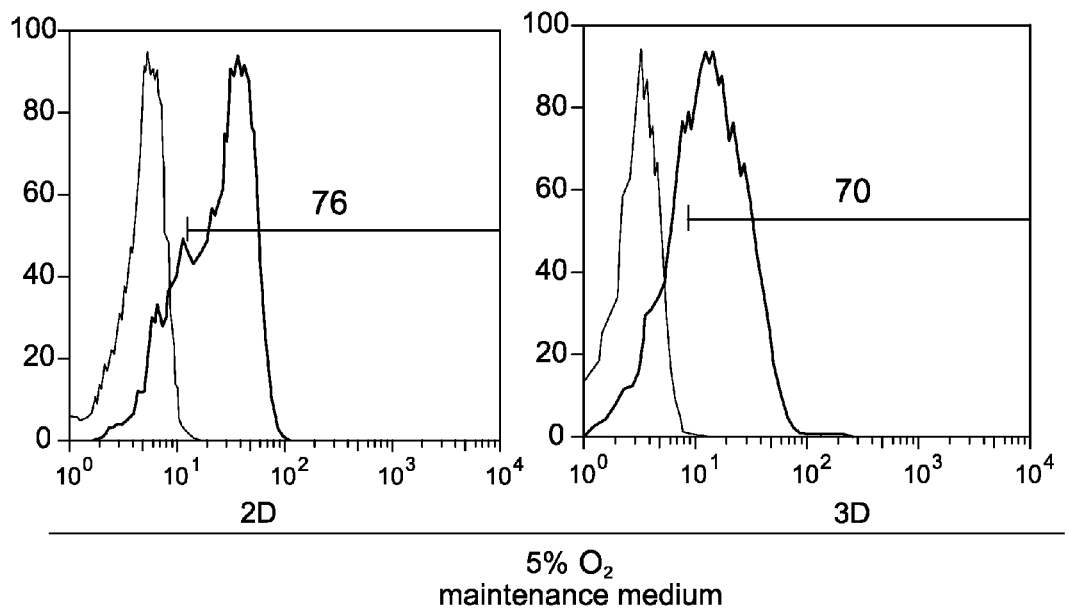
Figure 12C:
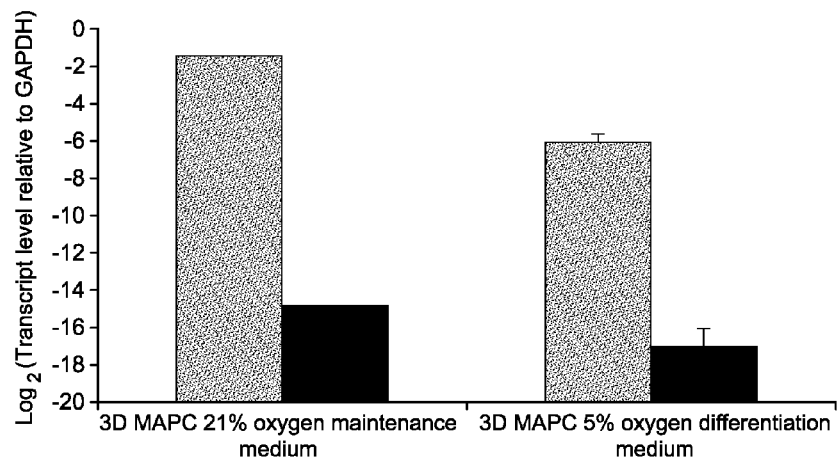
Figure 12D:
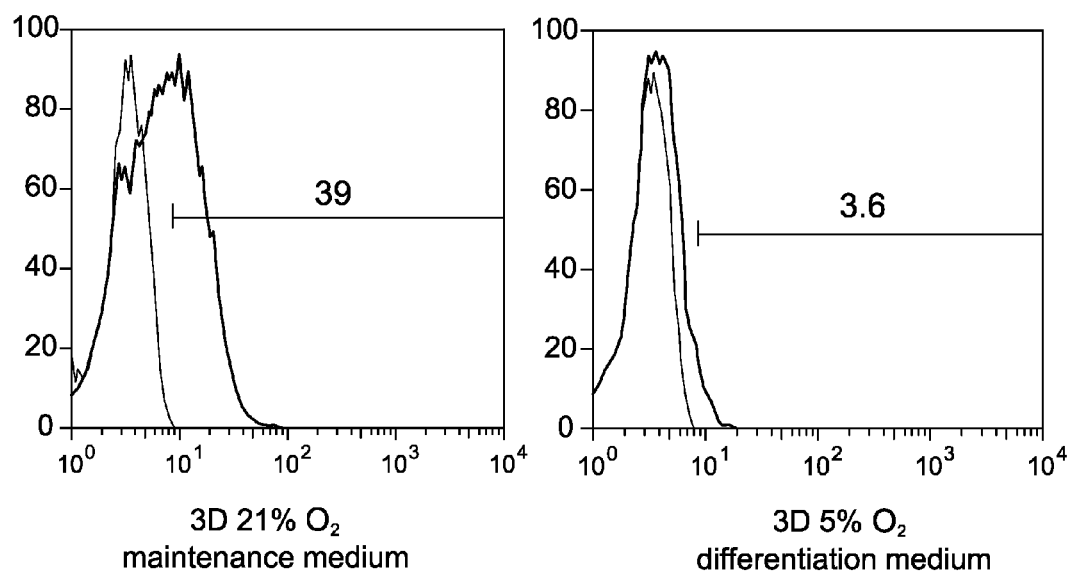

Cells were fixed in 80% ethanol and stored at −20° C. Fixed cells were washed twice with PBS and then stained in PBS with 50 µg/ml propidium iodide and 0.1 mg/ml RNAse overnight at 4° C. After washing cells were filtered and re-suspended in 500 µl PBS for flow cytometry analysis using FACS Calibur Results MAPC Self-Assemble into Cell Aggregates Aggregates were formed from single suspensions of MAPCs using two methods known as the hanging drop and the forced aggregation methods. rMAPC were inoculated at a starting cell concentration ranging from 3000-30,000 cells/ml (or 300 to 3000 cells per well or per drop) and single aggregate from each drop or well was readily formed. Aggregates were formed in complete MAPC medium or MAPC medium without LIF, PDGF and EGF (differentiation medium) in 5% or 21% oxygen. For all studies, two rat MAPC lines were tested at least in triplicates. Aggregates formed in complete MAPC medium with 5% oxygen, on day 4, expressed Oct4, Rex1, CD31 and HNF3b transcripts at levels comparable to the parent MAPC-line cultured on 2D surface (5% oxygen), but not Afp, a gene shown to be rapidly up-regulated when MAPC differentiate spontaneously (FIG. 12a). In addition, Oct4 protein expression was maintained in these aggregates as shown by flow cytometry (FIG. 12b). In contrast, aggregates formed in MAPC medium at 21% oxygen, were differentiating, as they expressed a 32 fold more Afp transcript (FIG. 12c) and the fraction of cells expressing Oct4 protein decreased by about 50% (FIG. 12d). Formation of aggregates in MAPC medium without LIF, PDGF and EGF even with a 5% oxygen resulted in a 21 fold decrease in Oct4 transcript (FIG. 12c) with only about 4% of the cells expressing Oct4 protein (FIG. 12d). Thus, both high ambient oxygen concentrations and removal of LIF, PDGF and EGF negatively affected the Oct4 expression during aggregate formation, and resulted in differentiation. Cells in MAPC aggregates formed under 5% $O_2$ in complete MAPC medium could also be trypsinized to single cell suspensions and re-cultivated on 2D surface exhibiting typical MAPC proliferation profiles and phenotype (FIG. 19).

Characterization of the MAPC Aggregates and Their Formation

Figure 13A:
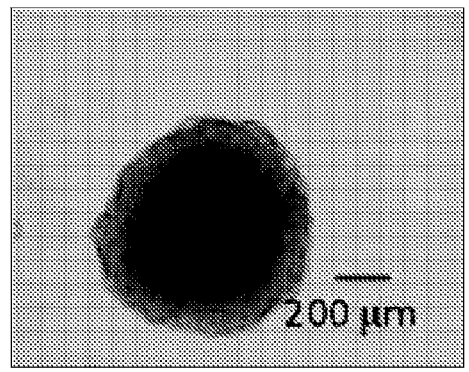
Figure 13B:
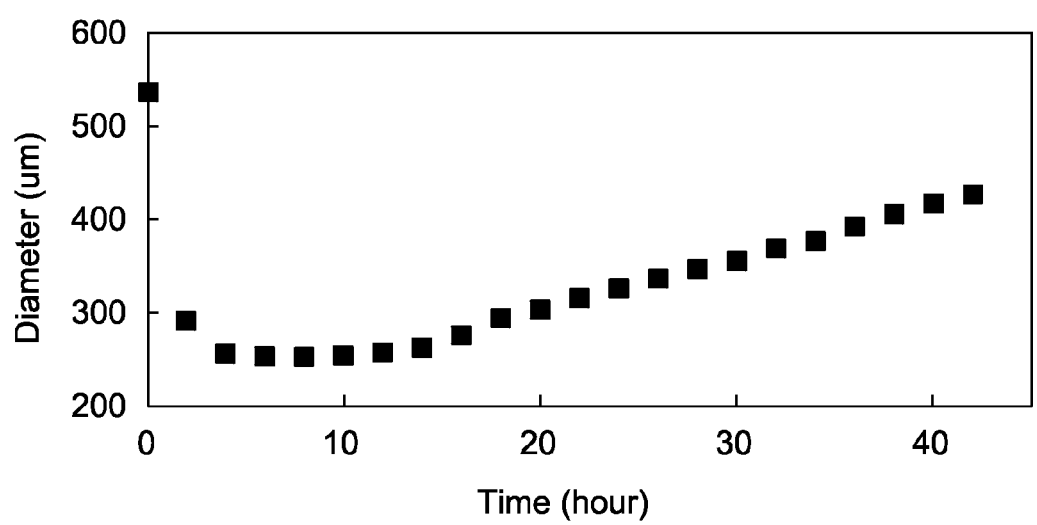
Figure 13C:
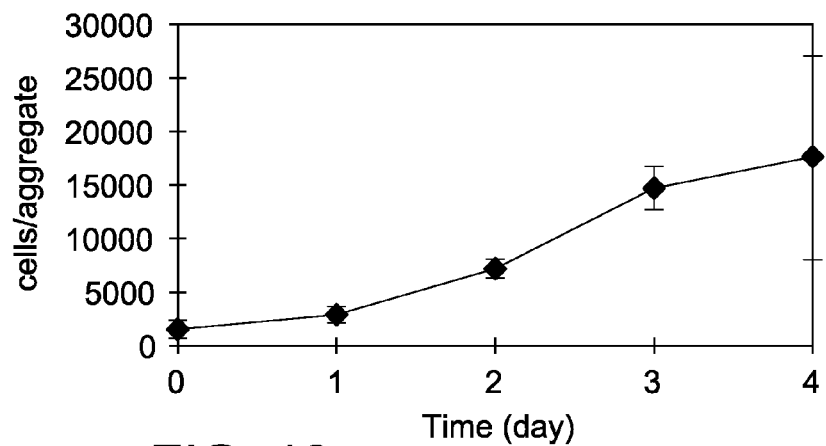

Four days after cell seeding, the MAPC aggregates had barely distinguishable cell-cell boundaries (FIG. 13a). Time-lapse microscopy was used to visualize the process of aggregate formation over a period of 48 hr. After the centrifugal settling to the bottom of a well, single cells clustered together to an average size of 540 µm. Subsequent compaction led to the cell aggregates of about 250 µm in size. The aggregate then increased in size to about 460 µm by 48 hr after the initial agglomeration (FIG. 13b). 10 aggregates were dissociated by trypsinization every day for cell counting. The average number of cells in each aggregate increased from 1000 to 17,758 cells per aggregate (668±19 µm, mean and SD of ten aggregates) in four days (FIG. 13c).

Figure 13D:
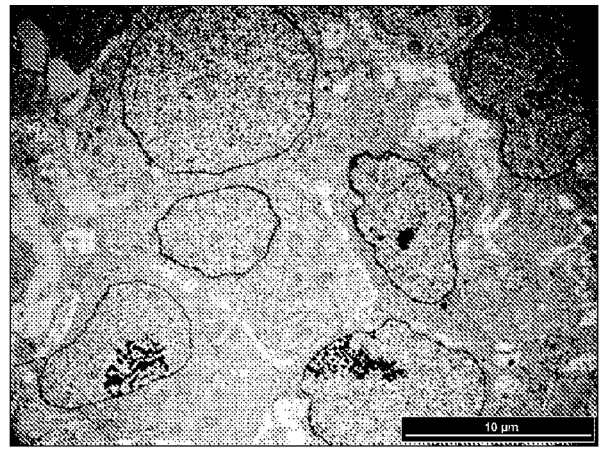
Figure 13E:
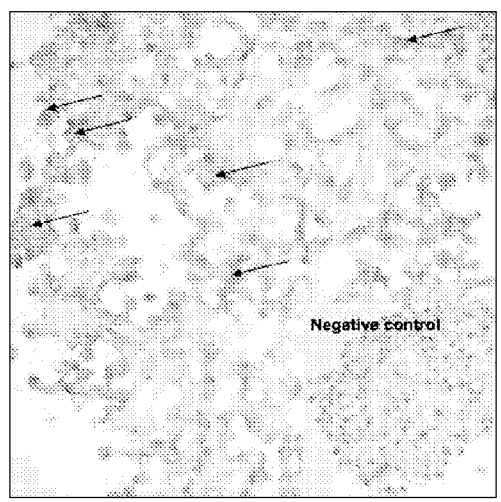

The population doubling time during the four days of formation was about 23 hr, slower than that seen when cultivated on a 2D surface (12-14 hr). The doubling time between Day 1 to 3 is approximately 12 hr. Between Day 3 and Day 4, a slow down in cell growth is observed (FIG. 13c). Cell cycle analysis done by flow cytometry indicated that a larger fraction (60%) of MAPC in aggregates (Day 4) were in G0/G1, in comparison to 2D surface culture (40%) (FIG. 20). TEM analysis of the aggregates showed tightly packed cells with high nucleus to cytoplasm ratio, a characteristic of MAPCs. Tight junctions were seen at cell-cell boundaries (FIG. 13d). Immunohistochemistry demonstrated that MAPC in aggregates expressed the cell membrane associated adhesion protein E-cadherin (FIG. 13e).

MAPC Aggregates Retain Differentiation Potential in Culture

Figure 14A:
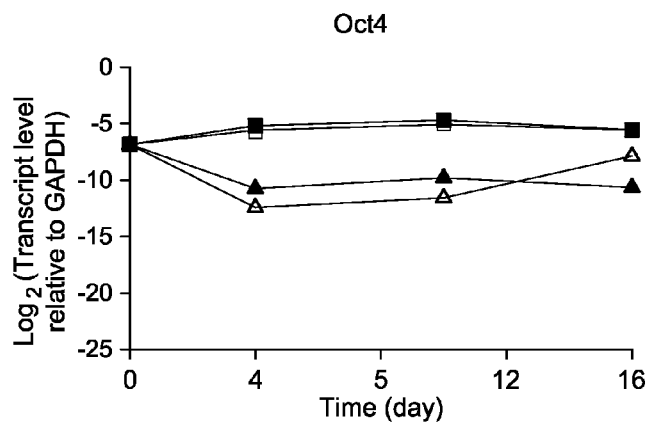
Figure 14B:
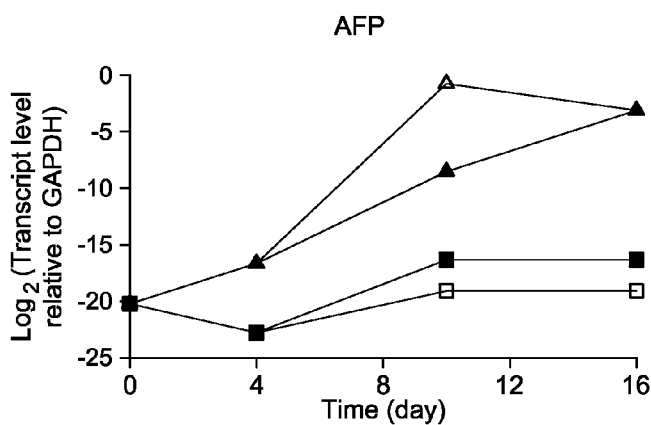

The inventors next examined whether MAPC aggregates could be maintained in culture for an extended periods of time without losing their characteristic phenotype. MAPC aggregates were allowed to form for four days and were subsequently kept for another sixteen days in complete MAPC culture medium or MAPC medium without LIF, PDGF and EGF with 50% medium change every two days. RT-qPCR for Oct4 and Afp transcript expression was used to evaluate the undifferentiated status of culture. MAPC aggregates maintained the level of Oct4 transcript without increase in Afp transcript level. However, for MAPC aggregates cultured in MAPC medium without LIF, PDGF and EGF (and with 21% oxygen), expression of Oct4 transcript decreased and the expression of Afp transcript progressively increased with time (FIG. 14a, 14b). During the sixteen days of culture in complete MAPC culture medium, cell proliferation occurred, as noted by the increase of the aggregates size or budding off of small groups of cells from the single MAPC aggregate to form smaller aggregate (FIG. 21).

Figure 14C:
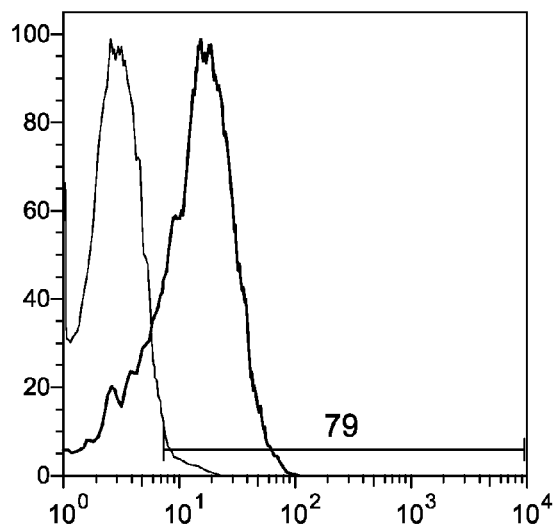
Figure 14D:
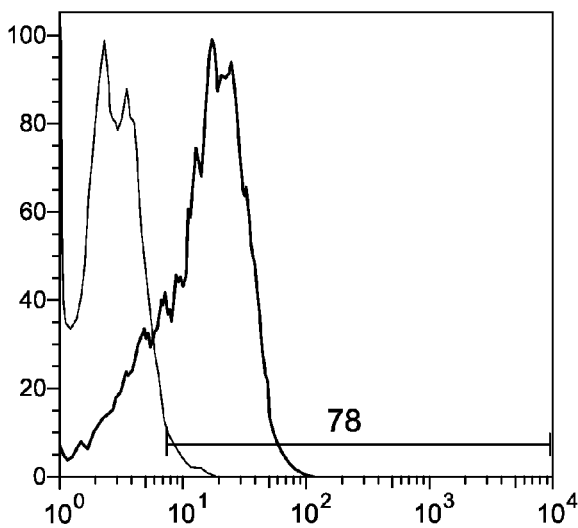
Figure 15A:
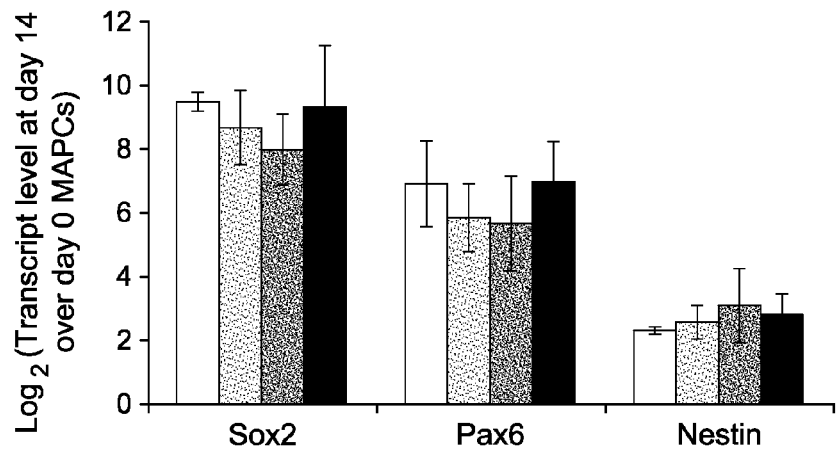
Figure 15B:
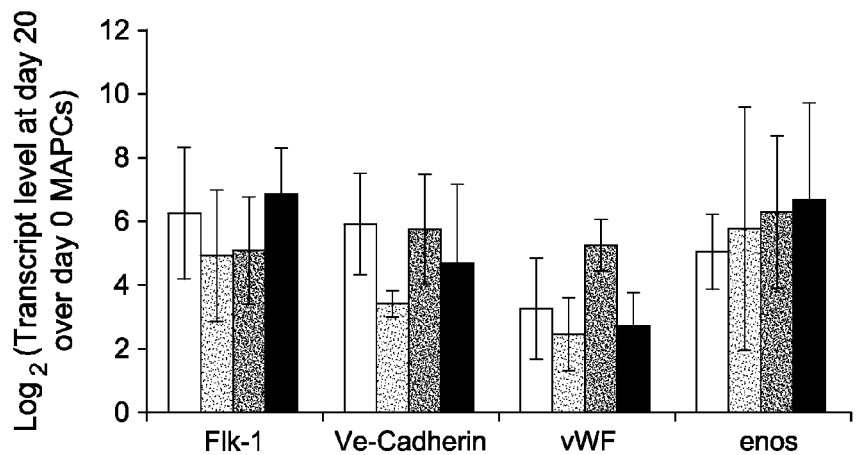
Figure 15C:
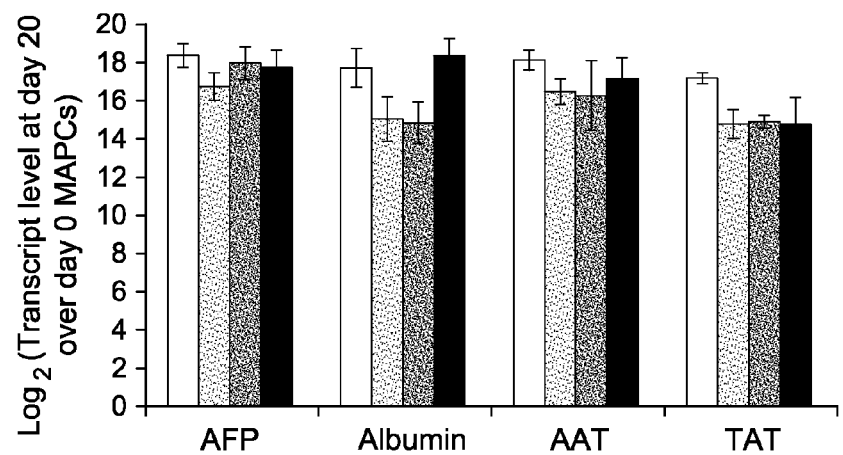

After sixteen days in culture, the MAPC aggregates were dissociated into single cells by trypsinization and the expression of Oct4 protein was evaluated by flow cytometry (FIG. 14c, 14d). The fraction of cells that continued to express Oct4 protein at the end of the sixteen-day culture (79% for one MAPC line and 78% for the other MAPC line) was similar to 2D monolayer cultures and MAPC aggregates on Day 0 (FIG. 12b). These cells were re-expanded and after two passages of expansion in 2D surface at low cell density, aggregate-derived cells were used for directed differentiation towards endothelial, hepatic and neural progenitor lineages and the differentiations were compared to that of MAPC maintained for the whole period at low cell density in 2D surface culture. As can be seen in FIG. 15, no significant differences in differentiation could be detected (student's t-test, with a p value cutoff of 0.05). During neural differentiation, similar increases in levels of expression of Sox2, Pax6 and Nestin transcripts were observed in both cells cultured as aggregates for sixteen days followed by 2D surface culture, as cells maintained in 2D surface culture for the whole time period (FIG. 15a) Similar results were observed in the endothelial differentiation as demonstrated by the increased expression of Flk-1, Ve-Cadherin, vWF, Enos transcripts (FIG. 15b), and in the hepatocyte lineage differentiation, shown by the increase in expression of Afp, Albumin, Aat and Tat transcripts (FIG. 15c). Thus, MAPC can be cultured as aggregates for at least sixteen days with differentiation potential for all three lineages.

Expansion of MAPC as Aggregates in Suspension Culture

Figure 16A:
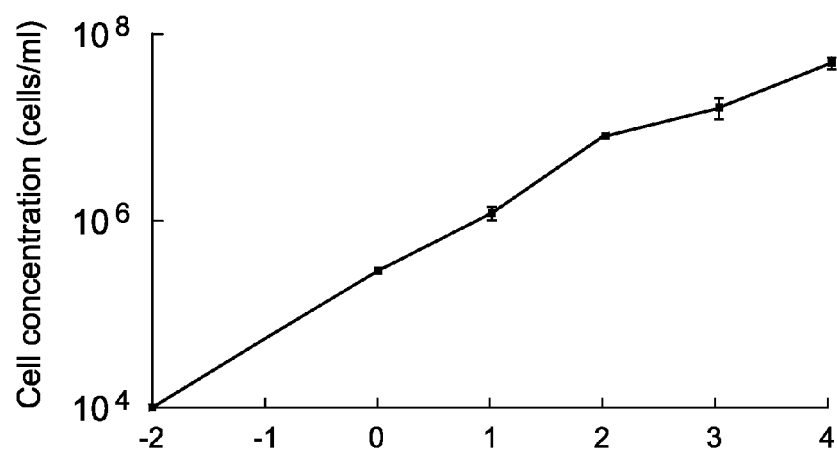
Figure 22A:
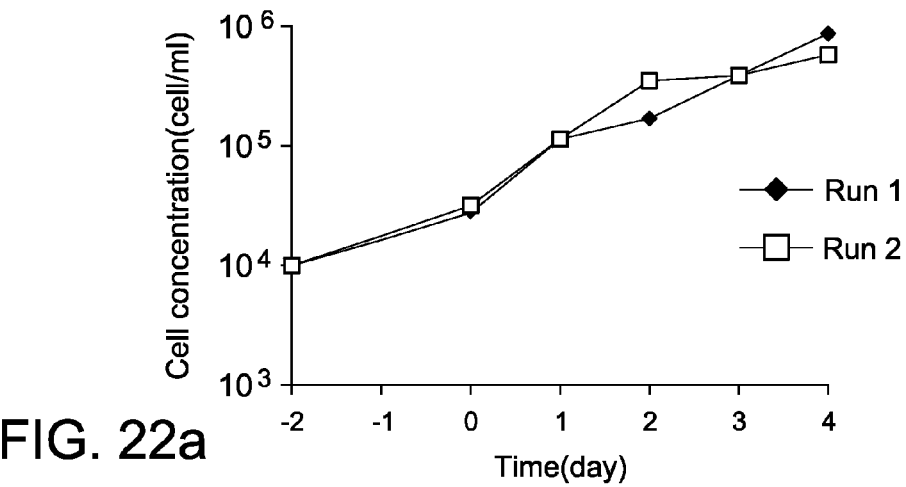

The inventors also determined if MAPC can be expanded as aggregates in suspension culture. The cultures were repeated three times with one MAPC cell line (FIG. 16) and twice with another MAPC line (FIG. 22). MAPC aggregates were formed under static culture conditions for two days and then seeded into a 250 ml spinner flask with a 100 ml working volume. During the first two days of static culture (day −2 to day 0) cell concentration grew from $10^4$ to $5 \times 10^4$ cells/ml. From day 0 to day 2 of suspension culture, an additional six-fold increase in cell number was seen. On day 2 of suspension culture, cell aggregates were harvested and the cell concentration in the flask was reduced to 50% and 50 ml of fresh medium was added. At the end of six days of culture, a final cell concentration of $7 \times 10^5$ cells/ml, equivalent to 70 fold expansion, was obtained for rMAPC-1 (FIG. 16a). Similar cell concentration was obtained on Day 4 of spinner expansion culture of the other rat MAPC line as well (FIG. 22a).

Figure 16B:
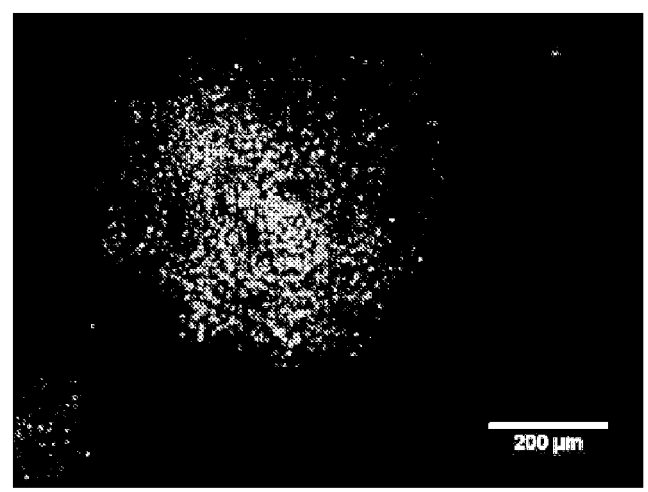
Figure 16C:
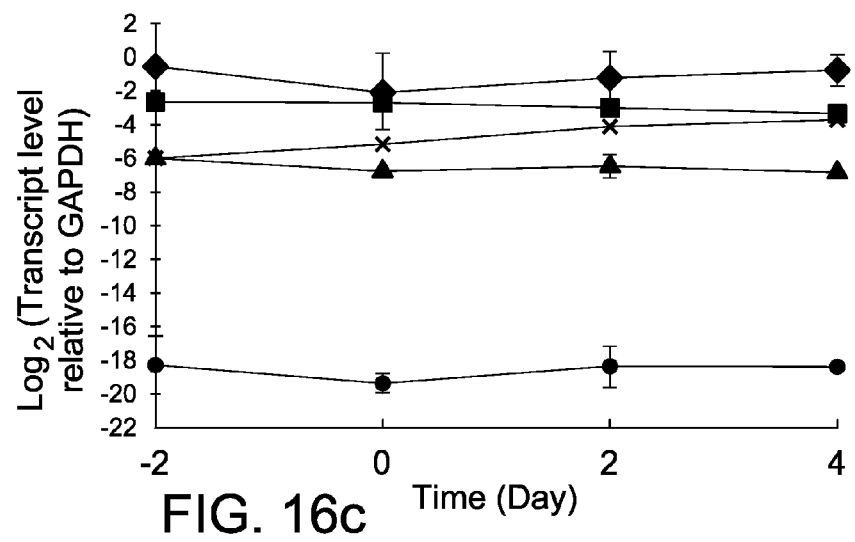
Figure 16D:
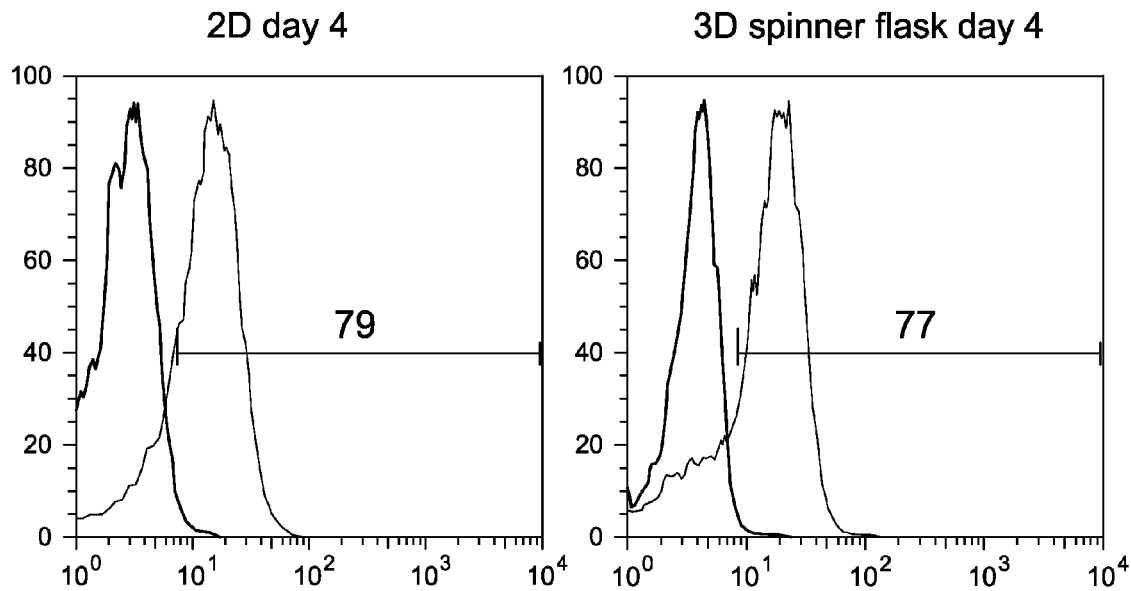
Figure 22B:
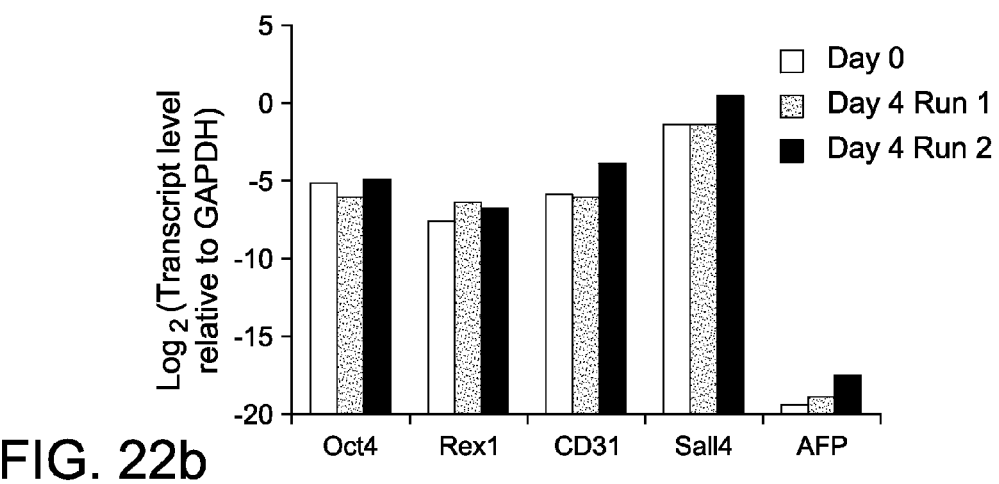
Figure 22C:
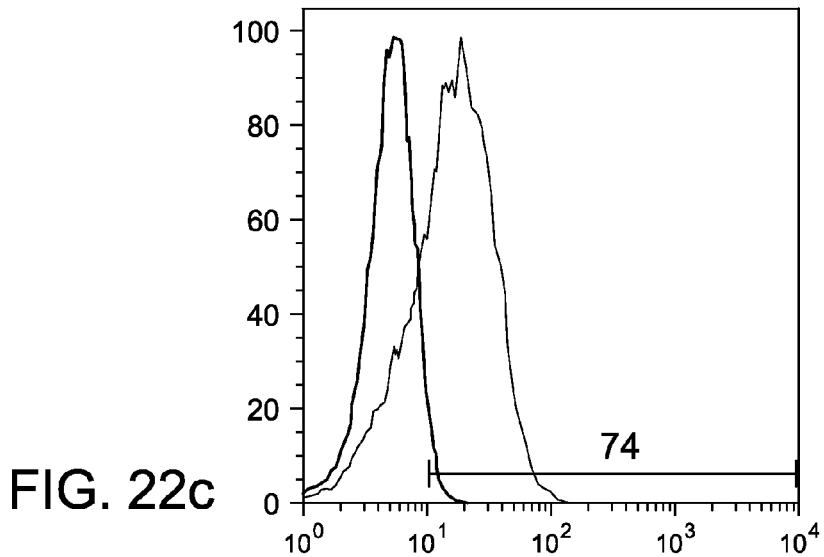

Staining with the LIVE/DEAD cytotoxicity kit (Molecular Probes) demonstrated that the cells within the aggregates (day 4) retained high viability (FIG. 16b). The transcript levels of key MAPC genes such as Oct4, Rex1, CD31, Sall4 and differentiation marker Afp of Day −2 (cells from 2D maintenance culture), Day 0 (cells after 48 h aggregation in wells) and Day 2 and 4 (aggregates in spinner cultures) were assessed by RT-qPCR. No differences in Oct4, Rex1, CD31 and Sall4 transcripts could be detected, and no increase in AFP expression was observed (FIG. 16c, FIG. 22b). In addition, the expression of Oct4 protein was also evaluated by flow cytometry. The fraction of cells that continued to express Oct4 protein at the end of spinner flask culture (day 4, 77% for one MAPC line and 74% for the other MAPC line) and the control 2D surface culture (day4, 79%) was similar (FIG. 16d, FIG. 22c). Thus, the cells in stirred suspension culture could be expanded without obvious signs of differentiation.

Figure 16E:
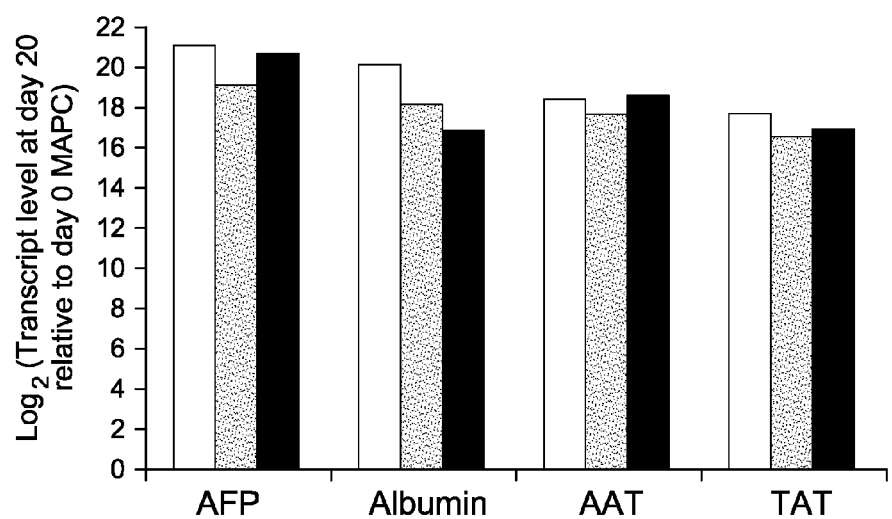

To evaluate whether MAPC aggregates cultivated in spinner continued to have similar differentiation potential, Day 0, 2 and 4 aggregates were subjected to hepatocyte differentiation as aggregates in static culture on 24 well ultra-low attachment plates. Differentiation towards the hepatocyte lineage was chosen because in vitro drug testing applications require large quantity of hepatocytes. The extent of up-regulation of hepatocyte-specific transcripts was evaluated by RT-qPCR at the end of twenty days of differentiation of cell aggregates collected at different points of spinner culture, over the expression levels in the starting cell aggregates, in each case. The MAPC aggregates (from Day 0, 2 and 4) were differentiated to 'hepatocyte-like' cells as shown by the up-regulation of hepatocyte specific transcripts Afp, Albumin, Aat and Tat (FIG. 16e). The level of up-regulation of these genes was similar for all starting cell populations. In addition, differentiated cells from each of the differentiations also secreted albumin at 0.7-0.8 pg/cell/day or about 10% of the level secreted by adult rat hepatocytes, and urea was secreted at 4-7 μg/day. Thus, the cells expanded in the spinner culture can also be used for generating large numbers of 'hepatocyte-like' cells.

Discussion

Stem cells offer great potential for regenerating and replacing dysfunctional tissues, and as tools for research on normal differentiation processes, models of disease, and for drug toxicity testing. Because of their importance in regenerative medicine and research, there is an increasing interest in the development of robust bioprocesses for generating large quantities of stem cells and their differentiated derivatives. Several bioreactor designs have been tested for cultivation of different stem cell types (reviewed extensively in (Kehoe et al. 2009; King and Miller 2007; Kirouac and Zandstra 2008). Among the different bioreactors, stirred tank based designs have been most widely used for the cultivation of mammalian cells because of the ease in maintaining homogeneous environment with online process monitoring and control. Furthermore, extensive experience and knowledge on their design and operation has accumulated in the past that will be useful in the scale up of stem cell bioprocesses.

REFERENCES

Abranches E, Bekman E, Henrique D, Cabral J M. 2007. Expansion of mouse embryonic stem cells on microcarriers. Biotechnol Bioeng 96(6):1211-21.

Anjos-Afonso F, Bonnet D. 2007. Nonhematopoietic/endothelial SSEA-1+ cells define the most primitive progenitors in the adult murine bone marrow mesenchymal compartment. Blood 109(3):1298-306.

Beltrami A P, Cesselli D, Bergamin N, Marcon P, Rigo S, Puppato E, D'Aurizio F, Verardo R, Piazza S, Pignatelli A and others. 2007. Multipotent cells can be generated in vitro from several adult human organs (heart, liver, and bone marrow). Blood 110(9):3438-46.

Breyer A, Estharabadi N, Oki M, Ulloa F, Nelson-Holte M, Lien L, Jiang Y. 2006. Multipotent adult progenitor cell isolation and culture procedures. Exp Hematol 34(11):1596-601.

Cameron C M, Hu W S, Kaufman D S. 2006. Improved development of human embryonic stem cell-derived embryoid bodies by stirred vessel cultivation. Biotechnol Bioeng 94(5):938-48.

Cormier J T, zur Nieden N I, Rancourt D E, Kallos M S. 2006. Expansion of undifferentiated murine embryonic stem cells as aggregates in suspension culture bioreactors. Tissue Eng 12(11):3233-45.

D'Ippolito G, Diabira S, Howard G A, Menei P, Roos B A, Schiller P C. 2004. Marrow-isolated adult multilineage inducible (MIAMI) cells, a unique population of postnatal young and old human cells with extensive expansion and differentiation potential. J Cell Sci 117(Pt 14):2971-81.

D'Ippolito G, Diabira S, Howard G A, Roos B A, Schiller P C. 2006. Low oxygen tension inhibits osteogenic differentiation and enhances stemness of human MIAMI cells. Bone 39(3):513-22.

Dang S M, Gerecht-Nir S, Chen J, Itskovitz-Eldor J, Zandstra P W. 2004. Controlled, scalable embryonic stem cell differentiation culture. Stem Cells 22(3):275-82.

Debeb B G, Galat V, Epple-Farmer J, Iannaccone S, Woodward W A, Bader M, Iannaccone P, Binas B. 2009. Isolation of Oct-4-expressing extraembryonic endoderm precursor cell lines. PLoS One 4(9):e7216.

Fok E Y, Zandstra P W. 2005. Shear-controlled single-step mouse embryonic stem cell expansion and embryoid body-based differentiation. Stem Cells 23(9):1333-42.

Frauenschuh S, Reichmann E, Ibold Y, Goetz P M, Sittinger M, Ringe J. 2007. A microcarrier-based cultivation system for expansion of primary mesenchymal stem cells. Biotechnol Prog 23(1):187-93.

Frith J E, Thomson B, Genever P. 2009. Dynamic three-dimensional culture methods enhance mesenchymal stem cell properties and increase therapeutic potential. Tissue Eng Part C Methods.

Galat V, Binas B, Iannaccone S, Postovit L M, Debeb B G, Iannaccone P. 2009. Developmental potential of rat extraembryonic stem cells. Stem Cells Dev 18(9):1309-18.

Gilbertson J A, Sen A, Behie L A, Kallos M S. 2006. Scaled-up production of mammalian neural precursor cell aggregates in computer-controlled suspension bioreactors. Biotechnol Bioeng 94(4):783-92.

Grayson W L, Zhao F, Izadpanah R, Bunnell B, Ma T. 2006. Effects of hypoxia on human mesenchymal stem cell expansion and plasticity in 3D constructs. J Cell Physiol 207(2):331-9.

Griffith L G, Swartz M A. 2006. Capturing complex 3D tissue physiology in vitro. Nat Rev Mol Cell Biol 7(3):211-24.

Guan K, Nayernia K, Maier L S, Wagner S, Dressel R, Lee J H, Nolte J, Wolf F, Li M, Engel W and others. 2006. Pluripotency of spermatogonial stem cells from adult mouse testis. Nature 440(7088):1199-203.

Gupta S, Verfullie C, Chmielewski D, Kren S, Eidman K, Connaire J, Heremans Y, Lund T, Blackstad M, Jiang Y and others. 2006. Isolation and characterization of kidney-derived stem cells. J Am Soc Nephrol 17(11):3028-40.

Hevehan D L, Papoutsakis E T, Miller W M. 2000. Physiologically significant effects of pH and oxygen tension on granulopoiesis. Exp Hematol 28(3):267-75.

Javazon E H, Beggs K J, Flake A W. 2004. Mesenchymal stem cells: paradoxes of passaging. Exp Hematol 32(5):414-25.

Jiang Y, Jahagirdar B N, Reinhardt R L, Schwartz R E, Keene C D, Ortiz-Gonzalez X R, Reyes M, Lenvik T, Lund T, Blackstad M and others. 2002. Pluripotency of mesenchymal stem cells derived from adult marrow. Nature 418 (6893):41-9.

Kehoe D E, Jing D, Lock L T, Tzanakakis E M. 2009. Scalable Stirred-suspension Bioreactor Culture of Human Pluripotent Stem Cells. Tissue Eng Part A.

Keller P J, Pampaloni F, Stelzer E H. 2006. Life sciences require the third dimension. Curr Opin Cell Biol 18(1): 117-24.

Kelm J M, Timmins N E, Brown C J, Fussenegger M, Nielsen L K. 2003. Method for generation of homogeneous multicellular tumor spheroids applicable to a wide variety of cell types. Biotechnol Bioeng 83(2):173-80.

King J A, Miller W M. 2007. Bioreactor development for stem cell expansion and controlled differentiation. Curr Opin Chem Biol 11(4):394-8.

Kirouac D C, Zandstra P W. 2008. The systematic production of cells for cell therapies. Cell Stem Cell 3(4):369-81.

Kogler G, Sensken S, Airey J A, Trapp T, Muschen M, Feldhahn N, Liedtke S, Sorg R V, Fischer J, Rosenbaum C and others. 2004. A new human somatic stem cell from placental cord blood with intrinsic pluripotent differentiation potential. J Exp Med 200(2):123-35.

Krawetz R, Taiani J T, Liu S, Meng G, Li X, Kallos M S, Rancourt D. 2009. Large-Scale Expansion of Pluripotent Human Embryonic Stem Cells in Stirred Suspension Bioreactors. Tissue Eng Part C Methods.

Kucia M, Reca R, Campbell F R, Zuba-Surma E, Majka M, Ratajczak J, Ratajczak M Z. 2006. A population of very small embryonic-like (VSEL) CXCR4(+)SSEA-1(+)Oct-4+ stem cells identified in adult bone marrow. Leukemia 20(5):857-69.

Kurosawa H. 2007. Methods for inducing embryoid body formation: in vitro differentiation system of embryonic stem cells. J Biosci Bioeng 103(5):389-98.

Kurosawa H, Imamura T, Koike M, Sasaki K, Amano Y. 2003. A simple method for forming embryoid body from mouse embryonic stem cells. J Biosci Bioeng 96(4):409-11.

Li Q, Liu Q, Cai H, Tan W S. 2006. A comparative gene-expression analysis of CD34+ hematopoietic stem and progenitor cells grown in static and stirred culture systems. Cell Mol Biol Lett 11(4):475-87.

Liu T, Zhang S, Chen X, Li G, Wang Y. 2009. Hepatic Differentiation of Mouse Embryonic Stem Cells in Three-dimensional Polymer Scaffolds. Tissue Eng Part A.

Lock L T, Tzanakakis E S. 2009. Expansion and differentiation of human embryonic stem cells to endoderm progeny in a microcarrier stirred-suspension culture. Tissue Eng Part A 15(8):2051-63.

Luttun A, Ross J J, Verfullie C, Aranguren X L, Prosper F. 2006. Differentiation of multipotent adult progenitor cells into functional endothelial and smooth muscle cells. Curr Protoc Immunol Chapter 22:Unit 22F 9.

Mostafa S S, Miller W M, Papoutsakis E T. 2000. Oxygen tension influences the differentiation, maturation and apoptosis of human megakaryocytes. Br J Haematol 111(3): 879-89.

Ng E S, Davis R P, Azzola L, Stanley E G, Elefanty A G. 2005. Forced aggregation of defined numbers of human embryonic stem cells into embryoid bodies fosters robust, reproducible hematopoietic differentiation. Blood 106(5):1601-3.

Niwa H. 2007. How is pluripotency determined and maintained? Development 134(4):635-46.

Oh S K, Chen A K, Mok Y, Chen X, Lim U M, Chin A, Choo A B, Reuveny S. 2009. Long-term microcarrier suspension cultures of human embryonic stem cells. Stem Cell Res.

Ong S M, Zhao Z, Arooz T, Zhao D, Zhang S, Du T, Wasser M, van Noort D, Yu H. 2009. Engineering a scaffold-free 3D tumor model for in vitro drug penetration studies. Biomaterials.

Pampaloni F, Reynaud E G, Stelzer E H. 2007. The third dimension bridges the gap between cell culture and live tissue. Nat Rev Mol Cell Biol 8(10):839-45.

Pochampally R R, Smith J R, Ylostalo J, Prockop D J. 2004. Serum deprivation of human marrow stromal cells (hMSCs) selects for a subpopulation of early progenitor cells with enhanced expression of OCT-4 and other embryonic genes. Blood 103(5):1647-52.

Potapova I A, Brink P R, Cohen I S, Doronin S V. 2008. Culturing of Human Mesenchymal Stem Cells as Three-dimensional Aggregates Induces Functional Expression of CXCR4That Regulates Adhesion to Endothelial Cells. J Biol Chem 283(19):13100-7.

Purpura K A, George S H, Dang S M, Choi K, Nagy A, Zandstra P W. 2008. Soluble Flt-1 regulates Flk-1 activation to control hematopoietic and endothelial development in an oxygen-responsive manner. Stem Cells 26(11):2832-42.

Ralston A, Rossant J. 2005. Genetic regulation of stem cell origins in the mouse embryo. Clin Genet. 68(2):106-12.

Ratajczak M Z, Zuba-Surma E K, Wysoczynski M, Ratajczak J, Kucia M. 2008. Very small embryonic-like stem cells: characterization, developmental origin, and biological significance. Exp Hematol 36(6):742-51.

Reyes M, Lund T, Lenvik T, Aguiar D, Koodie L, Verfullie C M. 2001. Purification and ex vivo expansion of postnatal human marrow mesodermal progenitor cells. Blood 98(9): 2615-25.

Rizzino A. 2009. Sox2 and Oct-3/4: A Versatile Pair of Master Regulators that Orchestrate the Self-renewal and Pluripotency of Embryonic Stem Cells by Functioning as Molecular Rheostats. Wiley Interdisc Rev Syst Biol Med 1(2): 228-236.

Sancho-Bru P, Najimi M, Caruso M, Pauwelyn K, Cantz T, Forbes S, Roskams T, Ott M, Gehling U, Sokal E and others. 2009. Stem and progenitor cells for liver repopulation: can we standardise the process from bench to bedside? Gut 58(4):594-603.

Schwartz R E, Reyes M, Koodie L, Jiang Y, Blackstad M, Lund T, Lenvik T, Johnson S, Hu W S, Verfullie C M. 2002. Multipotent adult progenitor cells from bone marrow differentiate into functional hepatocyte-like cells. J Clin Invest 109(10):1291-302.

Subramanian K, Geraerts M, Pauwelyn K A, Park Y, Owens D J, Muijtjens M, Ulloa-Montoya F, Jiang Y, Verfullie C M, Hu W S. Isolation procedure and characterization of multipotent adult progenitor cells from rat bone marrow. Methods Mol Biol 636:55-78.

Ulloa-Montoya F, Kidder B L, Pauwelyn K A, Chase L G, Luttun A, Crabbe A, Geraerts M, Sharov A A, Piao Y, Ko M S and others. 2007. Comparative transcriptome analysis of embryonic and adult stem cells with extended and limited differentiation capacity. Genome Biol 8(8):R163.

Yamada K M, Cukierman E. 2007. Modeling tissue morphogenesis and cancer in 3D. Cell 130(4):601-10.

Yoon Y S, Wecker A, Heyd L, Park J S, Tkebuchava T, Kusano K, Hanley A, Scadova H, Qin G, Cha DH and others. 2005. Clonally expanded novel multipotent stem cells from human bone marrow regenerate myocardium after myocardial infarction. J Clin Invest 115(2):326-38.

Yu Y, Li K, Bao C, Liu T, Jin Y, Ren H, Yun W. 2009. Ex vitro expansion of human placenta-derived mesenchymal stem cells in stirred bioreactor. Appl Biochem Biotechnol 159 (1):110-8.

Zhao F, Ma T. 2005. Perfusion bioreactor system for human mesenchymal stem cell tissue engineering: dynamic cell seeding and construct development. Biotechnol Bioeng 91(4):482-93.

zur Nieden N I, Cormier J T, Rancourt D E, Kallos M S. 2007. Embryonic stem cells remain highly pluripotent following long term expansion as aggregates in suspension bioreactors. J Biotechnol 129(3):421-32.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention.

What is claimed is:

1. A cell culture composition comprising aggregates of stem cells in non-static cell culture wherein the cell density ranges from about $5 \times 10^4$ cells/ml to about $10^8$ cells/ml, wherein the number of cells per aggregate is about 50,000 cells and the average diameter of each aggregate is about 1 mm.

2. A method for making the cell culture composition of claim 1, the method comprising inoculating a cell culture with stem cell aggregates and expanding the inoculated aggregates so that expansion produces a cell density of about $5\times10^4$ cells/ml to about $10^8$ cells/ml, wherein the number of cells per aggregate is about 50,000 cells and the average diameter of each aggregate is about 1 mm.

3. The cell culture composition of claim 1 wherein the aggregate of cells comprises cells that are not embryonic stem cells, embryonic germ cells, or germ cells and can differentiate into cell types of at least two of the endodermal, ectodermal and mesodermal embryonic lineages.

4. The cell culture composition of claim 1 wherein the aggregate of cells comprises cells that are isolated expanded non-embryonic stem, non-germ cells, the cells having undergone about 10-40 cell doublings in culture, wherein the cells express oct4, are not transformed, and have a normal karyotype.

5. The cell culture composition of claim 1 wherein the aggregate of cells comprises cells that are isolated expanded non-embryonic stem, non-germ cells that are obtained by culture of non-embryonic, non-germ tissue, the cells having undergone about 40 cell doublings in culture, wherein the cells are not transformed and have a normal karyotype.

6. The cell culture composition of claim 1 wherein the aggregate of cells comprises cells that are isolated expanded non-embryonic stem, non-germ cells, the cells having undergone about 10-40 cell doublings in culture, wherein the cells express telomerase, are not transformed, and have a normal karyotype.

7. The cell culture composition of claim 1 wherein the aggregate of cells comprises cells that are isolated expanded non-embryonic stem, non-germ cells that can differentiate into at least one cell type of at least two of the endodermal, ectodermal, and mesodermal embryonic lineages, said cells having undergone about 10-40 cell doublings in culture.

8. The cell culture composition of claim 1 wherein the aggregate of cells comprises cells that are positive for one or more of oct3/4, telomerase, rex-1, rox-1, nanog, GATA6 and sox-2.

* * * * *